US008187842B2

(12) United States Patent
D'Elia et al.

(10) Patent No.: US 8,187,842 B2
(45) Date of Patent: May 29, 2012

(54) ALTERED GLYOXYLATE SHUNT FOR IMPROVED PRODUCTION OF ASPARTATE-DERIVED AMINO ACIDS AND CHEMICALS

(75) Inventors: John N. D'Elia, Argenta, IL (US); Sean W. Jordan, Decatur, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 11/471,173

(22) Filed: Jun. 20, 2006

(65) Prior Publication Data

US 2007/0015261 A1 Jan. 18, 2007

Related U.S. Application Data

(60) Provisional application No. 60/692,341, filed on Jun. 20, 2005.

(51) Int. Cl.

| | |
|---|---|
| ***C12P 13/04*** | (2006.01) |
| ***C12P 13/08*** | (2006.01) |
| ***C12N 15/74*** | (2006.01) |
| ***C12N 1/21*** | (2006.01) |

(52) U.S. Cl. .................. 435/106; 435/252.33; 435/488; 435/115

(58) Field of Classification Search ........................ None
See application file for complete search history.

(56) References Cited

U.S. PATENT DOCUMENTS

| | | | | |
|---|---|---|---|---|
| 3,375,173 | A | 3/1968 | Nishimura et al. | |
| 3,580,810 | A | 5/1971 | Shiio et al. | |
| 4,321,325 | A | 3/1982 | Debabov et al. | |
| 4,347,318 | A | 8/1982 | Miwa et al. | |
| 4,368,266 | A | 1/1983 | Tosaka et al. | |
| 4,371,615 | A | 2/1983 | Miwa et al. | |
| 4,463,094 | A | 7/1984 | Chibata et al. | |
| 4,601,983 | A | 7/1986 | Nakamori et al. | |
| 4,757,009 | A | 7/1988 | Sano et al. | |
| 4,945,058 | A | 7/1990 | Yanai et al. | |
| 4,946,781 | A | 8/1990 | Nakamori et al. | |
| 4,980,285 | A | 12/1990 | Sano et al. | |
| 5,017,483 | A | 5/1991 | Furukawa et al. | |
| 5,077,207 | A | 12/1991 | Shiio et al. | |
| 5,087,566 | A | 2/1992 | Takano et al. | |
| 5,098,835 | A | 3/1992 | Yamada et al. | |
| 5,153,123 | A | 10/1992 | Terasawa et al. | |
| 5,164,307 | A | 11/1992 | Yoshihara et al. | |
| 5,169,768 | A | 12/1992 | Backman | |
| 5,175,107 | A | 12/1992 | Debabov et al. | |
| 5,236,831 | A | 8/1993 | Katsumata et al. | |
| 5,264,353 | A | 11/1993 | Yamada et al. | |
| 5,378,616 | A | 1/1995 | Tujimoto et al. | |
| 5,393,671 | A | 2/1995 | Tujimoto et al. | |
| 5,474,918 | A | 12/1995 | Kino et al. | |
| 5,939,307 | A | 8/1999 | Wang et al. | |
| 6,387,694 | B1 | 5/2002 | McKinney et al. | |
| 6,455,284 | B1 | 9/2002 | Gokarn et al. | |
| 6,630,332 | B2 | 10/2003 | Rieping et al. | |
| 2002/0106800 | A1 | 8/2002 | Liaw et al. | |
| 2003/0017556 | A1 | 1/2003 | Hermann | |
| 2003/0054503 | A1 | 3/2003 | Rieping et al. | |
| 2003/0059903 | A1 | 3/2003 | Rieping et al. | |
| 2003/0228678 | A1 | 12/2003 | Bathe et al. | |
| 2004/0132145 | A1 * | 7/2004 | Park et al. | 435/106 |
| 2004/0214294 | A1 | 10/2004 | Rieping | |
| 2004/0235122 | A1 | 11/2004 | Rieping et al. | |
| 2004/0241813 | A1 | 12/2004 | Rieping | |
| 2004/0241814 | A1 | 12/2004 | Rieping | |
| 2005/0032178 | A1 | 2/2005 | Rieping et al. | |
| 2005/0124047 | A1 | 6/2005 | Hermann | |
| 2005/0221448 | A1 | 10/2005 | Hermann | |

FOREIGN PATENT DOCUMENTS

| | | | |
|---|---|---|---|
| EP | 01408123 | A1 | 4/2004 |
| WO | 02/018722 | A2 | 10/2002 |
| WO | WO 02/081722 | A2 | 10/2002 |
| WO | 03/008604 | A2 | 1/2003 |
| WO | 03/008616 | A2 | 1/2003 |
| WO | WO 03/008603 | A2 | 1/2003 |
| WO | WO 03/008604 | A2 | 1/2003 |
| WO | WO 03/008607 | A2 | 1/2003 |
| WO | WO 03/008616 | A2 | 1/2003 |
| WO | WO 03/038106 | A2 | 5/2003 |
| WO | WO 03/076611 | A1 | 9/2003 |
| WO | 2004/033671 | A1 | 4/2004 |
| WO | WO 2004/087937 | A1 | 10/2004 |
| WO | WO 2005/103275 | A1 | 3/2005 |
| WO | WO 2005/054490 | A1 | 6/2005 |

OTHER PUBLICATIONS

Chung e tal. Glyoxylate Bypass operon of *Escherichia coli*: Cloning and Determination of the Functional Map. 1988 Journal of Bacteriology, Jan. 1988, p. 386-392.*

Smith et al. (Biochemical and Structural Studies of Malate Synthase from *Mycobacterium tuberculosis* J. Biol. Chem., vol. 278, Issue 3, 1735-1743, Jan. 17, 2003.*

(Continued)

*Primary Examiner* — Kagnew H Gebreyesus
(74) *Attorney, Agent, or Firm* — Mark W. Roberts

(57) ABSTRACT

The invention provides microbial strains possessing improved properties for production of aspartate-derived amino acids and chemicals. Methods of making such strains are provided. These methods include altering expression of the aceBAK operon, the glcB gene, or both. Alteration of expression may be accomplished through increased transcription, relief from native transcriptional control, and/or other means. Replacement of native promoters for these genes is also contemplated; for instance, their native promoters may be replaced by the tac promoter (Ptac).

15 Claims, 5 Drawing Sheets

OTHER PUBLICATIONS

Reincheild, et al. Characterization of the Isocitrate Lyase Gene from *Corynebacterium glutamicum* and Biochemical Analysis of the Enzyme. Journal of Bacteriology, 1994, p. 3474-3483.*
El-Mansi, et al.Molecular cloning and over-expression of the glyoxylate bypass operon from *Escherichia coli* ML308. Biochem. J. 1987, 242, pp. 661-665.*
Cozzon et al. Regulation of acetate Metabolism by protein phosphorylation in enteric bacteria. (Annu. Rev. Microbiology 1998, 52: 127-164).*
Smith et al. (Biochemical and Stuctural Studies of Malate Synthase from *Mycobacterium tuberculosis*, Journal of Biological Chemistry vol. 278, No. 3, pp. 1735-1743.*
Sharma et al. (Structure of isocitrate lyase, a persistence factor of *Mycobacterium tuberculosis* Nature Structural Biology 7, 663-668 (2000)).*
Falmagne et al (Purification and partial characterization of two malate synthases from *E. coli* Eur. J. Biochem. 37, 415-424 (1973.*
Pellicier et al Cross-induction of glc and ace Operons of *Escherichia coli* Attributable to Pathway Intersection, Journal of Biological Chemistry, 274, 1745-1752.*
Wendisch et al (Regulation of acetate metabolism in *Corynebacterium glutamicum*: transcriptional control of the isocytrate lyase and malate synthase genes Arch Microbiol (1997) 168: 262-269).*
Gui et al (1996) Autoregulation of icIR, the Gene Encoding the Repressor of the Glyoxylate Bypass Operon Journal of Bacteriology, Jan. 1996, p. 321-324.*
Paul Flamagne et al Purification et caracterisation partielle des deux malate synthases *d'Escherichia coli* Eur. J. Biochem. 37,415-424 (1973).*
Patek et al Promoters from *Corynebacterium glutamicum* : cloning. molecular analysis and search for a consensus motif Microbiology 1996, 142: 1297-1309.*
Cortay et al. Regulation of the acetate operon in *Escherichia coli*: purification and functional characterization of the IcIR repressor EMBO J 1991, vol. 10, No. 3, pp. 675-679.
Resnik et al. Integration Host Factor amplifies the induction of the aceBAK Operon of *Escherichia coli* by relieving IcIR repression Journal of Bacteriology May 1996 vol. 178, No. 9, pp. 2715-2717.
Boy, Emmanuelle, et al., "Multivalent Repression of Aspartic Semialdehyde Dehydrogenase in *Escherichia coli* K-12", Journal of Bacteriology, Oct. 1972, pp. 84-92.
Boy, Emmanuelle, "Role of Glucose-6-Phosphate in the Regulation of Aspartate Semialdehyde Dehydrogenase in *Escherichia coli*", FEMS Microbiology Letters 6(1979)189-192.
Haziza, Catherine, et al., "Nucleotide Sequence of the asd Gene of *Escherichia coli*: Absence of a Typical Attenutation Signal", EMBO Journal, vol. 1, No. 3, pp. 379-384, 1982.
Keseler, Ingrid M., et al., "EcoCyc: A Comprehensive Database Resource for *Escherichia coil*", Nucleic Acids Research, 2005, vol. 33, Database issue doi:10.1093/nar/gki108.
Haziza, Catherine, et al., "Identification of the promoter of the asd gene of *Escherichia coli* using in vitro fusion with the lac operon", Biochimie, 1982, 64, 227-230.
Oh, Min-Kyu et al., "Global Expression Profiling of Acetate-grown *Escherichia coli*", The Journal of Biological Chemistry, vol. 277, No. 15, Apr. 12, pp. 13175-13183, 2002.
Farmer, William R., et al. "Reduction of Aerobic Acetate Production by *Escherichia coli*", Applied Environmental Microbiology, Aug. 1997, p. 3205-3210, vol. 63, No. 8.
Ornston, L.N., et al., "Regulation of Glyoxylate Metabolism in *Escherichia coli* K-12", Journal of Bacteriology, Jun. 1969, p. 1098-1108, vol. 98, No. 3.
Resnik, Ernesto, et al., Integration Host Factor Amplifies the Induction of the aceBAK Operon of *Escherichia coli* by Relieving IcIR Repression, Journal of Bacteriology, May 1996.
Walsh, Kenneth, et al., "Determination of Flux Through the Branch Point of Two Metabolic Cycles", The Journal of Biological Chemistry, vol. 259, No. 15., Aug. 10, pp. 9646-9654, 1984.
Walsh, Kenneth, et al., "Branch Point Control by the Phosphorylation State of Isocitrate Dehydrogenase", The Journal of Biological Chemistry, vol. 260, No. 14, Jul. 15, pp. 1985.
Ochman, Howard, "Neutral Mutations and Neutral Substitutions in Bacterial Genomes", Mol. Biol. Evol. 20(12):2091-2096, vol. 20, No. 12, 2003.
Matsuoka et al., "Isolation, Hyperexpression, and Sequencing of the aceA Gene Encoding Isocitrate Lyase in *Escherichia coli*", Journal of Bacteriology, Oct. 1988, p. 4528-4536.
Bleicher et al., "Promoter Vectors with Restriction-Site Banks", Gene, 63 (1988) 135-139.
Joon et al., "Gene Amplification of aceA and aceB in Lysine-producing *Corynebacterium glutamicum* ssp. lactofermentum ATCC21799", Journal of Microbiology and Biotechnology, vol. 7, No. 5, 287-292, 1997.

* cited by examiner

Figure 4. Primers used in construction of strains of the invention aceBUS-kan4 (5'-GCA CAA CGA TCC TTC GTT CAC AGT GGG GAT AGA AGG CGG CGG TGG AAT- 3') (SEQ ID NO: 10)

tacaceB-kan3 (5'-CTG TTC AGT CAT CGT GCA GCT CCT CGT CAT GGC CAC ACA TTA TAC GAG CCG ATG ATT AAT TGT CAA AGG AAG CGG AAC ACG TAG AA-3') (SEQ ID NO: 11)

tac(2)aceB-kan3 (5'-GTT CAG TCA TCG TGC AGC TCC TCG TCA TGG ATC CAC ACA TTA TAC GAG CCG ATG ATT AAT TGT CAA AGG AAG CGG AAC ACG TAG AA-3') (SEQ ID NO: 12)

tac(3)aceB-kan3 (5'-CGT GCA GCT CCT CGT CAT GGA TCC GAA AAC TCC ACA CAT TAT ACG AGC CGA TGA TTA ATT GTC AAA GGA AGC GGA ACA CGT AGA A-3') (SEQ ID NO: 13)

tac4aceB (5'-AGC TCC TCG TCA TGG ATC CGA AAA CTT CCC CCA CAC ACA TTA TAC GAG CCG ATG A-3') (SEQ ID NO: 14)

tac5aceB (5'-CCT CGT CAT GGA TCC GAA AAC TTC CCC ACT CCA CAC ACA TTA TAC GAG CCG ATG A-3') (SEQ ID NO: 15)

aceB-tac\lacrev (5'-TTC ATC GGT TGT TGT TGC CTG TTC AGT CAT AGC TGT TTC CTG TGT GAA ATT GTT ATC CGC TCA CAA TTC CAC ACA CAT TAT ACG AGC CGA TGA-3') (SEQ ID NO: 16)

tac-glcB-spc1 (5'-TGG TTT GAC TCA TTG TTT ATC TCC TCG TTT TCC CAC ACA TTA TAC GAG CCG ATG ATT AAT TGT CAA TGA CCT GAT AGT TTG GCT GT3') (SEQ ID NO: 17)

glcBUS-spc2 (5'-AAA GCG GCA GCA GCG GTG TTG GCG AAT AAG CGT ACA GTC TAT GCC TCG GGC A-3') (SEQ ID NO: 18)

Figure 5

*Ptac* TTGACAATTAATCATCGGCTCGTATAATGTGTGG (SEQ ID NO: 9)

*Ptac-aceBAK*:
TTGACAATTAATCATCGGCTCGTATAATGTGTGGCCATGACGA GGAGCTGCACGATG (SEQ ID NO: 19)

*Ptac(2)-aceBAK*:
TTGACAATTAATCATCGGCTCGTATAATGTGTGGATCCATGAC GAGGAGCTGCACGATG (SEQ ID NO: 20)

*Ptac*(3)-aceBAK:
TTGACAATTAATCATCGGCTCGTATAATGTGTGGAGTTTTCGG ATCCATGACGAGGAGCTGCACGATG (SEQ ID NO: 21)

*Ptac(4)-aceBAK*:
TTGACAATTAATCATCGGCTCGTATAATGTGTGGGGAAGTTT TCGGATCCATGACGAGGAGCTGCACGATG (SEQ ID NO: 22)

*Ptac(5)-aceBAK*:
TTGACAATTAATCATCGGCTCGTATAATGTGTGGAGTGGGAA GTTTTCGGATCCATGACGAGGAGCTGCACGATG (SEQ ID NO: 23)

*Ptac\lac-aceBAK*:
TTGACAATTAATCATCGGCTCGTATAATGTGTGGAATTGTGAGC GGATAACAATTTCACACAGGAAACAGCTATG (SEQ ID NO: 24)

*Ptac-glcB*:
TTGACAATTAATCATCGGCTCGTATAATGTGTGGGAAAACGAG GACATAAACAATG (SEQ ID NO: 25)

SEQUENCE LISTING

```
<160> NUMBER OF SEQ ID NOS: 60

<210> SEQ ID NO 1
<211> LENGTH: 81
<212> TYPE: DNA
<213> ORGANISM: Escherichia coli

<400> SEQUENCE: 1

tatttttaat taaaatggaa attgtttttg attttgcatt ttaaatgagt agtcttagtt      60

gtgctgaacg aaaagagcac a                                                81


<210> SEQ ID NO 2
<211> LENGTH: 1305
<212> TYPE: DNA
<213> ORGANISM: Escherichia coli

<400> SEQUENCE: 2

atgaaaaccc gtacacaaca aattgaagaa ttacagaaag agtggactca accgcgttgg      60

gaaggcatta ctcgcccata cagtgcggaa gatgtggtga aattacgcgg ttcagtcaat     120

cctgaatgca cgctggcgca actgggcgca gcgaaaatgt ggcgtctgct gcacggtgag     180

tcgaaaaaag gctacatcaa cagcctcggc gcactgactg gcggtcaggc gctgcaacag     240

gcgaaagcgg gtattgaagc agtctatctg tcgggatggc aggtagcggc ggacgctaac     300

ctggcggcca gcatgtatcc ggatcagtcg ctctatccgg caaactcggt gccagctgtg     360

gtggagcgga tcaacaacac cttccgtcgt gccgatcaga tccaatggtc cgcgggcatt     420

gagccgggcg atccgcgcta tgtcgattac ttcctgccga tcgttgccga tgcggaagcc     480

ggttttggcg gtgtcctgaa tgcctttgaa ctgatgaaag cgatgattga agccggtgca     540

gcggcagttc acttcgaaga tcagctggcg tcagtgaaga aatgcggtca catgggcggc     600

aaagttttag tgccaactca ggaagctatt cagaaactgg tcgcggcgcg tctggcagct     660

gacgtgacgg gcgttccaac cctgctggtt gcccgtaccg atgctgatgc ggcggatctg     720

atcacctccg attgcgaccc gtatgacagc gaatttatta ccggcgagcg taccagtgaa     780

ggcttcttcc gtactcatgc gggcattgag caagcgatca gccgtggcct ggcgtatgcg     840

ccatatgctg acctggtctg gtgtgaaacc tccacgccgg atctggaact ggcgcgtcgc     900

tttgcacaag ctatccacgc gaaatatccg ggcaaactgc tggcttataa ctgctcgccg     960
```

-continued

```
tcgttcaact ggcagaaaaa cctcgacgac aaaactattg ccagcttcca gcagcagctg   1020

tcggatatgg gctacaagtt ccagttcatc accctggcag gtatccacag catgtggttc   1080

aacatgtttg acctggcaaa cgcctatgcc cagggcgagg gtatgaagca ctacgttgag   1140

aaagtgcagc agccggaatt tgccgccgcg aaagatggct ataccttcgt atctcaccag   1200

caggaagtgg gtacaggtta cttcgataaa gtgacgacta ttattcaggg cggcacgtct   1260

tcagtcaccg cgctgaccgg ctccactgaa gaatcgcagt tctaa                   1305


<210> SEQ ID NO 3
<211> LENGTH: 434
<212> TYPE: PRT
<213> ORGANISM: Escherichia coli

<400> SEQUENCE: 3

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320
```

```
Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe


<210> SEQ ID NO 4
<211> LENGTH: 1602
<212> TYPE: DNA
<213> ORGANISM: Escherichia coli

<400> SEQUENCE: 4

atgactgaac aggcaacaac aaccgatgaa ctggctttca caaggccgta tggcgagcag      60

gagaagcaaa ttcttactgc cgaagcggta gaatttctga ctgagctggt gacgcatttt     120

acgccacaac gcaataaact tctggcagcg cgcattcagc agcagcaaga tattgataac     180

ggaacgttgc ctgattttat ttcggaaaca gcttccattc gcgatgctga ttggaaaatt     240

cgcgggattc ctgcggactt agaagaccgc cgcgtagaga taactggccc ggtagagcgc     300

aagatggtga tcaacgcgct caacgccaat gtgaaagtct ttatggccga tttcgaagat     360

tcactggcac cagactggaa caaagtgatc gacgggcaaa ttaacctgcg tgatgcggtt     420

aacggcacca tcagttacac caatgaagca ggcaaaattt accagctcaa gcccaatcca     480

gcggttttga tttgtcgggt acgcggtctg cacttgccgg aaaaacatgt cacctggcgt     540

ggtgaggcaa tccccggcag cctgtttgat tttgcgctct atttcttcca caactatcag     600

gcactgttgg caaagggcag tggtccctat ttctatctgc cgaaaaccca gtcctggcag     660

gaagcggcct ggtggagcga agtcttcagc tatgcagaag atcgctttaa tctgccgcgc     720

ggcaccatca aggcgacgtt gctgattgaa acgctgcccg ccgtgttcca gatggatgaa     780

atccttcacg cgctgcgtga ccatattgtt ggtctgaact gcggtcgttg ggattacatc     840

ttcagctata tcaaaacgtt gaaaaactat cccgatcgcg tcctgccaga cagacaggca     900

gtgacgatgg ataaaccatt cctgaatgct tactcacgcc tgttgattaa aacctgccat     960

aaacgcggtg cttttgcgat gggcggcatg gcggcgttta ttccgagcaa agatgaagag    1020

cacaataacc aggtgctcaa caaagtaaaa gcggataaat cgctggaagc caataacggt    1080

cacgatggca catggatcgc tcacccaggc cttgcggaca cggcaatggc ggtattcaac    1140

gacattctcg gctcccgtaa aaatcagctt gaagtgatgc gcgaacaaga cgcgccgatt    1200

actgccgatc agctgctggc accttgtgat ggtgaacgca ccgaagaagg tatgcgcgcc    1260

aacattcgcg tggctgtgca gtacatcgaa gcgtggatct ctggcaacgg ctgtgtgccg    1320

atttatggcc tgatggaaga tgcggcgacg gctgaaattt cccgtacctc gatctggcag    1380

tggatccatc atcaaaaaac gttgagcaat ggcaaaccgg tgaccaaagc cttgttccgc    1440

cagatgctgg gcgaagagat gaaagtcatt gccagcgaac tgggcgaaga acgtttctcc    1500
```

-continued

```
caggggcgtt ttgacgatgc cgcacgcttg atggaacaga tcaccacttc cgatgagtta   1560

attgatttcc tgaccctgcc aggctaccgc ctgttagcgt aa                       1602


<210> SEQ ID NO 5
<211> LENGTH: 533
<212> TYPE: PRT
<213> ORGANISM: Escherichia coli

<400> SEQUENCE: 5

Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Gln Asp Ile Asp Asn Gly Thr Leu Pro
    50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Arg Val Glu Ile Thr Gly
                85                  90                  95

Pro Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Gln Ala Leu Leu Ala Lys Gly Ser Gly
        195                 200                 205

Pro Tyr Phe Tyr Leu Pro Lys Thr Gln Ser Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
    290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
```

```
        355                 360                 365

Pro Gly Leu Ala Asp Thr Ala Met Ala Val Phe Asn Asp Ile Leu Gly
    370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510

Gln Ile Thr Thr Ser Asp Glu Leu Ile Asp Phe Leu Thr Leu Pro Gly
        515                 520                 525

Tyr Arg Leu Leu Ala
    530


<210> SEQ ID NO 6
<211> LENGTH: 81
<212> TYPE: DNA
<213> ORGANISM: Escherichia coli

<400> SEQUENCE: 6

ggtctgaccg gtagctaaag agatagacga aaacgaaaag cccgcttaat aactgttcac      60

agaagcagcg cgcaaaaatc a                                                81


<210> SEQ ID NO 7
<211> LENGTH: 2172
<212> TYPE: DNA
<213> ORGANISM: Escherichia coli

<400> SEQUENCE: 7

atgagtcaaa ccataaccca gagccgttta cgcattgacg ccaattttaa acgttttgtg      60

gatgaagaag ttttaccggg aacagggctg gacgctgcgg cgttctggcg caattttgat     120

gagatcgttc atgatctggc accagaaaat cgtcagttgc tggcagaacg cgatcgcatt     180

caggcagcgc ttgatgagtg gcatcgcagc aatccggggc cggtaaaaga taaagcggcc     240

tataaatctt tcctgcgtga actgggctac ctggtgccgc aaccggagcg cgtgacggtg     300

gaaaccacgg gcattgacag cgaaatcacc agccaggcgg ggccgcagct ggtggttccg     360

gcaatgaacg cccgctacgc gctgaacgcg gcgaacgctc gctggggctc actgtacgat     420

gcgttatacg gcagcgacat catcccgcag gaaggggcga tggtcagcgg ctacgatccg     480

caacgcggtg agcaggttat cgcctgggtt cggcgtttcc tcgatgaatc tctaccgctg     540

gaaaacggca gctatcagga tgtggtggcg tttaaggtgg ttgataaaca attacgcatc     600

cagttgaaaa atggtaaaga aaccacgtta cgtactccag cacagtttgt cggttaccgt     660

ggcgatgccg ctgcgccgac ctgcattttg ctgaaaaata acggcctgca tattgagctg     720

caaatcgatg ccaatgggcg gattggcaaa gacgatccgg cgcacatcaa cgatgttatc     780
```

gtcgaagctg ctatcagtac cattctcgac tgcgaagatt cggtcgcggc ggttgatgcg 840
gaagataaaa tcctgctgta ccgcaacctg ctgggcctga tgcaggggac tctgcaagag 900
aaaatggaga aaaacggtcg gcaaatcgtg cgtaaactga atgacgatcg tcattacacc 960
gccgccgatg gctctgaaat ttctctgcac ggacgctcgc tgctgtttat ccgcaacgtg 1020
ggtcatttga tgaccattcc tgtgatttgg gacagcgaag gcaatgaaat cccggaaggc 1080
attcttgatg gcgtcatgac tggcgcgatt gccctctatg atttaaaagt gcagaaaaac 1140
tcgcgcactg gcagcgtcta tattgtgaaa ccgaaaatgc acggtccgca ggaagtggcg 1200
ttcgccaaca aactgtttac ccgcattgag acaatgctcg gtatggcacc gaataccctg 1260
aaaatgggca ttatggatga agaacgtcgg acctcgctga acttgcgtag ctgtatcgct 1320
caggcgcgca accgcgtggc gttcatcaat accggtttcc tcgaccgtac cggcgatgaa 1380
atgcattcgg tgatggaagc tggcccgatg ctgcgtaaaa atcagatgaa atcgacgcct 1440
tggatcaaag cctacgagcg taataacgtg ctttccggtc tgttctgtgg gctgcgcggt 1500
aaagcgcaaa ttggtaaagg catgtgggca atgccggacc tgatggcaga catgtacagc 1560
cagaagggcg accaactgcg tgccggggca aacacagcct gggttccgtc accaaccgct 1620
gctacgctcc atgcgctgca ctaccaccaa accaacgtac agagcgtaca agccaacatt 1680
gcccagaccg agttcaatgc tgaatttgaa ccgctgctgg acgatctgct gactattccg 1740
gttgctgaaa acgctaactg gtcggcgcaa gagatccaac aagagctgga taacaacgtg 1800
caggggattc tggggtacgt ggtgcgctgg gtggagcagg ggattggttg ttcaaaagtg 1860
ccggatattc acaatgtggc gttgatggaa gaccgcgcaa cgctgcgtat ctccagccag 1920
catatcgcca actggttacg tcacggtatt ctgaccaaag aacaggtgca ggcgtcgctg 1980
gagaatatgg cgaaagtggt tgatcagcaa aacgctggcg atccggctta tcgtccgatg 2040
gcggggaatt tcgctaactc gtgtgctttt aaagctgcca gcgatttaat cttcctcggc 2100
gtgaaacagc caaacggcta taccgaaccg ttattacacg cctggcgttt acgcgaaaaa 2160
gaaagtcatt aa 2172

<210> SEQ ID NO 8
<211> LENGTH: 723
<212> TYPE: PRT
<213> ORGANISM: Escherichia coli

<400> SEQUENCE: 8

Met Ser Gln Thr Ile Thr Gln Ser Arg Leu Arg Ile Asp Ala Asn Phe
1 5 10 15

Lys Arg Phe Val Asp Glu Glu Val Leu Pro Gly Thr Gly Leu Asp Ala
20 25 30

Ala Ala Phe Trp Arg Asn Phe Asp Glu Ile Val His Asp Leu Ala Pro
35 40 45

Glu Asn Arg Gln Leu Leu Ala Glu Arg Asp Arg Ile Gln Ala Ala Leu
50 55 60

Asp Glu Trp His Arg Ser Asn Pro Gly Pro Val Lys Asp Lys Ala Ala
65 70 75 80

Tyr Lys Ser Phe Leu Arg Glu Leu Gly Tyr Leu Val Pro Gln Pro Glu
85 90 95

Arg Val Thr Val Glu Thr Thr Gly Ile Asp Ser Glu Ile Thr Ser Gln
100 105 110

Ala Gly Pro Gln Leu Val Val Pro Ala Met Asn Ala Arg Tyr Ala Leu
115 120 125

-continued

```
Asn Ala Ala Asn Ala Arg Trp Gly Ser Leu Tyr Asp Ala Leu Tyr Gly
    130                 135                 140

Ser Asp Ile Ile Pro Gln Glu Gly Ala Met Val Ser Gly Tyr Asp Pro
145                 150                 155                 160

Gln Arg Gly Glu Gln Val Ile Ala Trp Val Arg Arg Phe Leu Asp Glu
                165                 170                 175

Ser Leu Pro Leu Glu Asn Gly Ser Tyr Gln Asp Val Val Ala Phe Lys
            180                 185                 190

Val Val Asp Lys Gln Leu Arg Ile Gln Leu Lys Asn Gly Lys Glu Thr
        195                 200                 205

Thr Leu Arg Thr Pro Ala Gln Phe Val Gly Tyr Arg Gly Asp Ala Ala
    210                 215                 220

Ala Pro Thr Cys Ile Leu Leu Lys Asn Asn Gly Leu His Ile Glu Leu
225                 230                 235                 240

Gln Ile Asp Ala Asn Gly Arg Ile Gly Lys Asp Asp Pro Ala His Ile
                245                 250                 255

Asn Asp Val Ile Val Glu Ala Ala Ile Ser Thr Ile Leu Asp Cys Glu
            260                 265                 270

Asp Ser Val Ala Ala Val Asp Ala Glu Asp Lys Ile Leu Leu Tyr Arg
        275                 280                 285

Asn Leu Leu Gly Leu Met Gln Gly Thr Leu Gln Glu Lys Met Glu Lys
    290                 295                 300

Asn Gly Arg Gln Ile Val Arg Lys Leu Asn Asp Asp Arg His Tyr Thr
305                 310                 315                 320

Ala Ala Asp Gly Ser Glu Ile Ser Leu His Gly Arg Ser Leu Leu Phe
                325                 330                 335

Ile Arg Asn Val Gly His Leu Met Thr Ile Pro Val Ile Trp Asp Ser
            340                 345                 350

Glu Gly Asn Glu Ile Pro Glu Gly Ile Leu Asp Gly Val Met Thr Gly
        355                 360                 365

Ala Ile Ala Leu Tyr Asp Leu Lys Val Gln Lys Asn Ser Arg Thr Gly
    370                 375                 380

Ser Val Tyr Ile Val Lys Pro Lys Met His Gly Pro Gln Glu Val Ala
385                 390                 395                 400

Phe Ala Asn Lys Leu Phe Thr Arg Ile Glu Thr Met Leu Gly Met Ala
                405                 410                 415

Pro Asn Thr Leu Lys Met Gly Ile Met Asp Glu Glu Arg Arg Thr Ser
            420                 425                 430

Leu Asn Leu Arg Ser Cys Ile Ala Gln Ala Arg Asn Arg Val Ala Phe
        435                 440                 445

Ile Asn Thr Gly Phe Leu Asp Arg Thr Gly Asp Glu Met His Ser Val
    450                 455                 460

Met Glu Ala Gly Pro Met Leu Arg Lys Asn Gln Met Lys Ser Thr Pro
465                 470                 475                 480

Trp Ile Lys Ala Tyr Glu Arg Asn Asn Val Leu Ser Gly Leu Phe Cys
                485                 490                 495

Gly Leu Arg Gly Lys Ala Gln Ile Gly Lys Gly Met Trp Ala Met Pro
            500                 505                 510

Asp Leu Met Ala Asp Met Tyr Ser Gln Lys Gly Asp Gln Leu Arg Ala
        515                 520                 525

Gly Ala Asn Thr Ala Trp Val Pro Ser Pro Thr Ala Ala Thr Leu His
    530                 535                 540

Ala Leu His Tyr His Gln Thr Asn Val Gln Ser Val Gln Ala Asn Ile
```

-continued

```
545                 550                 555                 560

Ala Gln Thr Glu Phe Asn Ala Glu Phe Glu Pro Leu Leu Asp Asp Leu
                565                 570                 575

Leu Thr Ile Pro Val Ala Glu Asn Ala Asn Trp Ser Ala Gln Glu Ile
            580                 585                 590

Gln Gln Glu Leu Asp Asn Asn Val Gln Gly Ile Leu Gly Tyr Val Val
        595                 600                 605

Arg Trp Val Glu Gln Gly Ile Gly Cys Ser Lys Val Pro Asp Ile His
    610                 615                 620

Asn Val Ala Leu Met Glu Asp Arg Ala Thr Leu Arg Ile Ser Ser Gln
625                 630                 635                 640

His Ile Ala Asn Trp Leu Arg His Gly Ile Leu Thr Lys Glu Gln Val
                645                 650                 655

Gln Ala Ser Leu Glu Asn Met Ala Lys Val Val Asp Gln Gln Asn Ala
            660                 665                 670

Gly Asp Pro Ala Tyr Arg Pro Met Ala Gly Asn Phe Ala Asn Ser Cys
        675                 680                 685

Ala Phe Lys Ala Ala Ser Asp Leu Ile Phe Leu Gly Val Lys Gln Pro
    690                 695                 700

Asn Gly Tyr Thr Glu Pro Leu Leu His Ala Trp Arg Leu Arg Glu Lys
705                 710                 715                 720

Glu Ser His


<210> SEQ ID NO 9
<211> LENGTH: 34
<212> TYPE: DNA
<213> ORGANISM: Artificial Sequence
<220> FEATURE:
<223> OTHER INFORMATION: Synthetic Promoter

<400> SEQUENCE: 9

ttgacaatta atcatcggct cgtataatgt gtgg                                34


<210> SEQ ID NO 10
<211> LENGTH: 48
<212> TYPE: DNA
<213> ORGANISM: Artificial Sequence
<220> FEATURE:
<223> OTHER INFORMATION: PCR Primer

<400> SEQUENCE: 10

gcacaacgat ccttcgttca cagtggggat agaaggcggc ggtggaat                  48


<210> SEQ ID NO 11
<211> LENGTH: 86
<212> TYPE: DNA
<213> ORGANISM: Artificial Sequence
<220> FEATURE:
<223> OTHER INFORMATION: PCR Primer

<400> SEQUENCE: 11

ctgttcagtc atcgtgcagc tcctcgtcat ggccacacat tatacgagcc gatgattaat     60

tgtcaaagga agcggaacac gtagaa                                          86


<210> SEQ ID NO 12
<211> LENGTH: 86
<212> TYPE: DNA
<213> ORGANISM: Artificial Sequence
<220> FEATURE:
<223> OTHER INFORMATION: PCR Primer
```

<400> SEQUENCE: 12
gttcagtcat cgtgcagctc ctcgtcatgg atccacacat tatacgagcc gatgattaat 60
tgtcaaagga agcggaacac gtagaa 86

<210> SEQ ID NO 13
<211> LENGTH: 85
<212> TYPE: DNA
<213> ORGANISM: Artificial Sequence
<220> FEATURE:
<223> OTHER INFORMATION: PCR Primer

<400> SEQUENCE: 13
cgtgcagctc ctcgtcatgg atccgaaaac tccacacatt atacgagccg atgattaatt 60
gtcaaaggaa gcggaacacg tagaa 85

<210> SEQ ID NO 14
<211> LENGTH: 55
<212> TYPE: DNA
<213> ORGANISM: Artificial Sequence
<220> FEATURE:
<223> OTHER INFORMATION: PCR Primer

<400> SEQUENCE: 14
agctcctcgt catggatccg aaaacttccc ccacacacat tatacgagcc gatga 55

<210> SEQ ID NO 15
<211> LENGTH: 55
<212> TYPE: DNA
<213> ORGANISM: Artificial Sequence
<220> FEATURE:
<223> OTHER INFORMATION: PCR Primer

<400> SEQUENCE: 15
cctcgtcatg gatccgaaaa cttccccact ccacacacat tatacgagcc gatga 55

<210> SEQ ID NO 16
<211> LENGTH: 93
<212> TYPE: DNA
<213> ORGANISM: Artificial Sequence
<220> FEATURE:
<223> OTHER INFORMATION: PCR Primer

<400> SEQUENCE: 16
ttcatcggtt gttgttgcct gttcagtcat agctgtttcc tgtgtgaaat tgttatccgc 60
tcacaattcc acacacatta tacgagccga tga 93

<210> SEQ ID NO 17
<211> LENGTH: 86
<212> TYPE: DNA
<213> ORGANISM: Artificial Sequence
<220> FEATURE:
<223> OTHER INFORMATION: PCR Primer

<400> SEQUENCE: 17
tggtttgact cattgtttat ctcctcgttt tcccacacat tatacgagcc gatgattaat 60
tgtcaatgac ctgatagttt ggctct 86

<210> SEQ ID NO 18
<211> LENGTH: 52
<212> TYPE: DNA
<213> ORGANISM: Artificial Sequence
<220> FEATURE:
<223> OTHER INFORMATION: PCR Primer -continued

<400> SEQUENCE: 18
aaagcggcag cagcggtgtt ggcgaataag cgtacagtct atgcctcggg ca 52

<210> SEQ ID NO 19
<211> LENGTH: 57
<212> TYPE: DNA
<213> ORGANISM: Artificial Sequence
<220> FEATURE:
<223> OTHER INFORMATION: Fusion

<400> SEQUENCE: 19
ttgacaatta atcatcggct cgtataatgt gtggccatga cgaggagctg cacgatg 57

<210> SEQ ID NO 20
<211> LENGTH: 59
<212> TYPE: DNA
<213> ORGANISM: Artificial Sequence
<220> FEATURE:
<223> OTHER INFORMATION: Fusion

<400> SEQUENCE: 20
ttgacaatta atcatcggct cgtataatgt gtggatccat gacgaggagc tgcacgatg 59

<210> SEQ ID NO 21
<211> LENGTH: 68
<212> TYPE: DNA
<213> ORGANISM: Artificial Sequence
<220> FEATURE:
<223> OTHER INFORMATION: Fusion

<400> SEQUENCE: 21
ttgacaatta atcatcggct cgtataatgt gtggagtttt cggatccatg acgaggagct 60
gcacgatg 68

<210> SEQ ID NO 22
<211> LENGTH: 72
<212> TYPE: DNA
<213> ORGANISM: Artificial Sequence
<220> FEATURE:
<223> OTHER INFORMATION: Fusion

<400> SEQUENCE: 22
ttgacaatta atcatcggct cgtataatgt gtgggggaag ttttcggatc catgacgagg 60
agctgcacga tg 72

<210> SEQ ID NO 23
<211> LENGTH: 76
<212> TYPE: DNA
<213> ORGANISM: Artificial Sequence
<220> FEATURE:
<223> OTHER INFORMATION: Fusion

<400> SEQUENCE: 23
ttgacaatta atcatcggct cgtataatgt gtggagtggg gaagttttcg gatccatgac 60
gaggagctgc acgatg 76

<210> SEQ ID NO 24
<211> LENGTH: 75
<212> TYPE: DNA
<213> ORGANISM: Artificial Sequence
<220> FEATURE:
<223> OTHER INFORMATION: Fusion

<400> SEQUENCE: 24

-continued

```
ttgacaatta atcatcggct cgtataatgt gtggaattgt gagcggataa caatttcaca     60

caggaaacag ctatg                                                      75
```

<210> SEQ ID NO 25
<211> LENGTH: 56
<212> TYPE: DNA
<213> ORGANISM: Artificial Sequence
<220> FEATURE:
<223> OTHER INFORMATION: Fusion

<400> SEQUENCE: 25

```
ttgacaatta atcatcggct cgtataatgt gtgggaaaac gaggacataa acaatg         56
```

<210> SEQ ID NO 26
<211> LENGTH: 2220
<212> TYPE: DNA
<213> ORGANISM: Corynebacterium glutamicum

<400> SEQUENCE: 26

```
atgactgaac aggaactgtt gtctgctcag actgccgaca acgctggaac tgacagcacc     60

gaacgcgttg acgcgggcgg aatgcaggtt gcaaaagttc tctacgactt tgtaaccgaa    120

gcggtactcc ctcgcgtggg tgtggatgcg gaaaagttct ggtccggatt cgccgccatc    180

gcccgggacc tcaccccacg caaccgcgag ctgcttgctc gccgcgatga actgcagatg    240

cttatcgacg actaccaccg caacaactcc ggcaccatcg accaagaggc gtacgaggat    300

ttcctcaaag aaatcggata cttggttgag gagccagaag ctgcagaaat ccgtacccaa    360

aacgtcgata cggaaatctc cagcaccgca ggacctcagc tggttgttcc aattctgaac    420

gcacgcttcg cgctgaacgc tgccaatgct cgctggggtt ccctctacga tgcgttgtac    480

ggcaccaacg ccatcccaga aactgatggc gctgaaaagg gcaaggagta caacccggtc    540

cgcggccaga aggtcatcga gtggggtcgt gaattcctcg acagcgttgt cccactggac    600

ggtgcttcgc atgccgatgt tgagaagtac aacatcaccg atggaaagct tgcagcccac    660

attggagata gcgtctaccg actgaaaaac cgtgaatcct accgtggctt caccggcaac    720

ttccttgatc cagaagcaat cctgctggaa accaacggcc tgcacatcga gctgcagatc    780

gatcctgtcc acccaatcgg caaggcagac aagactggtc tcaaagacat cgttttggaa    840

tctgcgatca ccacgatcat ggacttcgaa gactccgttg cagctgttga tgctgaagac    900

aagaccttag gttactctaa ctggttcgga ctcaacaccg gcgaactgaa agaagagatg    960

tccaagaacg gacgcatctt cacccgtgag ctcaacaagg accgcgtcta cattggccgc   1020

aatggtaccg agctggttct gcacggtcgt tccctgctgt tcgtccgcaa cgttggtcac   1080

ctcatgcaaa acccatccat cttgattgat ggcgaggaga tcttcgaagg catcatggat   1140

gctgtcttga ccactgtttg tgccatccca ggaattgctc cgcagaacaa gatgcgcaat   1200

tcccgcaagg gctccatcta catcgtgaag cctaagcagc acggccctga agaagtcgcg   1260

ttcaccaacg agctcttcgg ccgcgttgag gatctgcttg atctgccacg ccacaccttg   1320

aaggttggtg ttatggatga ggagcgtcgc acgtccgtga acctggatgc cagcatcatg   1380

gaagttgctg accgcttggc attcatcaac actggcttcc tggaccgcac cggcgatgaa   1440

atccacacct ccatggaagc aggcgccatg gtgcgcaagg ctgatatgca gaccgcaccg   1500

tggaagcagg cctacgagaa caacaacgtt gatgcaggta ttcagcgtgg tcttcctggc   1560

aaggctcaga tcggtaaggg catgtgggcg atgactgaac tcatggcaga aatgctggag   1620

aagaagatcg gccagccacg cgaaggcgcc aacactgcat gggttccttc accaactggt   1680
```

-continued gcgacgctgc acgcaacgca ctaccacttg gttgatgtgt tcaaggttca agacgaactg 1740
cgtgctgccg gccgccgcga cagcctgcgc aacattctca ccattccaac cgcaccaaac 1800
accaattggt ctgaggaaga gaagaaggaa gagatggaca acaactgcca gtccatcctc 1860
ggatacgttg tgcgctgggt tgagcacggt gttggttgct ccaaggttcc agacatccat 1920
gacatcgacc tcatggaaga ccgcgcaacg ctgcgtattt cctcgcagat gctggccaac 1980
tggatccgcc atgatgttgt ctcgaaggag caggtcttgg agtcactgga acgaatggca 2040
gtggtcgtcg acaagcaaaa tgcgggcgac gaggcctacc gcgatatggc gccgaactac 2100
gacgcctccc tcgccttcca ggcggctaag gacttgattt tcgaaggcac caagtcccca 2160
tcgggctaca ccgagcccat cttgcacgca cgccgccgcg agttcaaagc aaaaaactaa 2220

<210> SEQ ID NO 27
<211> LENGTH: 1299
<212> TYPE: DNA
<213> ORGANISM: Corynebacterium glutamicum

<400> SEQUENCE: 27
atgtcaaacg ttggaaagcc acgtaccgca caggaaatcc agcaggattg ggacaccaac 60
cctcgttgga acggcatcac ccgcgactac accgcagacc aggtagctga tctgcagggt 120
tccgtcatcg aggagcacac tcttgctcgc cgcggctcag agatcctctg ggacgcagtc 180
acccaggaag gtgacggata catcaacgcg cttggcgcac tcaccggtaa ccaggctgtt 240
cagcaggttc gtgcaggcct gaaggctgtc tacctgtccg gttggcaggt cgcaggtgac 300
gccaacctct ccggccacac ctaccctgac cagtccctct acccagcgaa ctccgttcca 360
agcgtcgttc gtcgcatcaa caacgcactg ctgcgttccg atgaaatcgc acgcaccgaa 420
ggcgacacct ccgttgacaa ctgggttgtc ccaatcgtcg cggacggcga agctggcttc 480
ggtggagcac tcaacgtcta cgaactccag aaggcaatga tcgcagctgg cgctgcaggc 540
acccactggg aagaccagct cgcttctgaa aagaagtgtg gccacctcgg cggcaaggtt 600
ctgatcccaa cccagcagca catccgcacc ctgaactctg cccgccttgc agcagacgtt 660
gcaaacaccc caactgttgt tatcgcacgt accgacgctg aggcagcaac cctgatcacc 720
tctgacgttg atgagcgcga ccaaccattc atcaccggtg agcgcaccgc agaaggctac 780
taccacgtca agaatggtct cgagccatgt atcgcacgtg caaagtccta cgcaccatac 840
gcagatatga tctggatgga gaccggcacc cctgacctgg agctcgctaa gaagttcgct 900
gaaggcgttc gctctgagtt cccagaccag ctgctgtcct acaactgctc cccatccttc 960
aactggtctg cacacctcga ggcagatgag atcgctaagt tccagaagga actcggcgca 1020
atgggcttca agttccagtt catcaccctc gcaggcttcc actccctcaa ctacggcatg 1080
ttcgacctgg cttacggata cgctcgcgaa ggcatgacct ccttcgttga cctgcagaac 1140
cgtgagttca aggcagctga agagcgtggc ttcaccgctg ttaagcacca gcgtgaggtt 1200
ggcgcaggct acttcgacca gatcgcaacc accgttgacc cgaactcttc taccaccgct 1260
ttgaagggtt ccactgaaga aggccagttc cacaactag 1299

<210> SEQ ID NO 28
<211> LENGTH: 434
<212> TYPE: PRT
<213> ORGANISM: Escherichia coli

<400> SEQUENCE: 28

Met Lys Thr Arg Thr Gln Gln Ile Glu Glu Leu Gln Lys Glu Trp Thr
1 5 10 15

-continued

```
Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe
```

<210> SEQ ID NO 29
<211> LENGTH: 434
<212> TYPE: PRT
<213> ORGANISM: Shigella flexneri

<400> SEQUENCE: 29

```
Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Asn Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Val Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Gln Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380
```

```
Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe


<210> SEQ ID NO 30
<211> LENGTH: 434
<212> TYPE: PRT
<213> ORGANISM: Escherichia coli o157:h7

<400> SEQUENCE: 30

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Asp Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ser Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Val Tyr Leu Ser Gly Trp Gln Val Ala
                85                  90                  95

Ala Asp Ala Asn Leu Ala Ala Ser Met Tyr Pro Asp Gln Ser Leu Tyr
            100                 105                 110

Pro Ala Asn Ser Val Pro Ala Val Val Glu Arg Ile Asn Asn Thr Phe
        115                 120                 125

Arg Arg Ala Asp Gln Ile Gln Trp Ser Ala Gly Ile Glu Pro Gly Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ala Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Thr Gly
    210                 215                 220

Val Pro Thr Leu Leu Val Ala Arg Thr Asp Ala Asp Ala Ala Asp Leu
225                 230                 235                 240

Ile Thr Ser Asp Cys Asp Pro Tyr Asp Ser Glu Phe Ile Thr Gly Glu
                245                 250                 255

Arg Thr Ser Glu Gly Phe Phe Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Glu Ala
    290                 295                 300

Ile His Ala Lys Tyr Pro Gly Lys Leu Leu Ala Tyr Asn Cys Ser Pro
305                 310                 315                 320
```

-continued

```
Ser Phe Asn Trp Gln Lys Asn Leu Asp Asp Asn Thr Ile Ala Ser Phe
                325                 330                 335

Gln Gln Gln Leu Ser Asp Met Gly Tyr Lys Phe Gln Phe Ile Thr Leu
            340                 345                 350

Ala Gly Ile His Ser Met Trp Phe Asn Met Phe Asp Leu Ala Asn Ala
        355                 360                 365

Tyr Ala Gln Gly Glu Gly Met Lys His Tyr Val Glu Lys Val Gln Gln
    370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Thr Ser Ser Val Thr Ala Leu Thr Gly Ser Thr Glu Glu Ser
            420                 425                 430

Gln Phe


<210> SEQ ID NO 31
<211> LENGTH: 434
<212> TYPE: PRT
<213> ORGANISM: Salmonella paratyphi-a

<400> SEQUENCE: 31

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Glu Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ala Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Ile Tyr Leu Ser Gly Trp Gln Val Ala
                85                  90                  95

Ala Asp Ala Asn Leu Ala Ser Ser Met Tyr Pro Asp Gln Ser Leu Tyr
            100                 105                 110

Pro Ala Asn Ser Val Pro Ala Val Val Asp Arg Ile Asn Asn Thr Phe
        115                 120                 125

Arg Arg Ala Asp Gln Ile Gln Trp Ala Ser Gly Ile Glu Pro Asn Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ser Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Met Gly
    210                 215                 220

Val Pro Thr Leu Val Ile Ala Arg Thr Asp Ala Asp Ala Ala Asp Leu
225                 230                 235                 240

Ile Thr Ser Asp Cys Asp Pro Tyr Asp Ser Gly Phe Ile Thr Gly Glu
                245                 250                 255

Arg Thr Ser Glu Gly Phe Tyr Arg Thr His Ala Gly Ile Glu Gln Ala
```

260 265 270

Ile Ser Arg Gly Leu Ala Tyr Ala Pro Tyr Ala Asp Leu Val Trp Cys
275 280 285

Glu Thr Ser Thr Pro Asp Leu Glu Leu Ala Arg Arg Phe Ala Asp Ala
290 295 300

Ile His Ala Lys Tyr Pro Gly Lys Leu Leu Ala Tyr Asn Cys Ser Pro
305 310 315 320

Ser Phe Asn Trp Gln Lys Asn Leu Asp Asp Lys Thr Ile Ala Ser Phe
325 330 335

Gln Gln Gln Leu Ser Asp Met Gly Tyr Lys Tyr Gln Phe Ile Thr Leu
340 345 350

Ala Gly Ile His Ser Met Trp Phe Asn Met Phe Asp Leu Ala His Ala
355 360 365

Tyr Ala Gln Gly Glu Gly Met Lys His Tyr Val Glu Lys Val Gln Gln
370 375 380

Pro Glu Phe Ala Ala Ala Lys Asp Gly Tyr Thr Phe Val Ser His Gln
385 390 395 400

Gln Glu Val Gly Thr Gly Tyr Phe Asp Lys Val Thr Thr Ile Ile Gln
405 410 415

Gly Gly Ala Ser Ser Val Thr Ala Leu Thr Gly Ser Thr Glu Glu Ser
420 425 430

Gln Phe

<210> SEQ ID NO 32
<211> LENGTH: 434
<212> TYPE: PRT
<213> ORGANISM: Salmonella choleraesuis

<400> SEQUENCE: 32

Met Lys Thr Arg Thr Gln Gln Ile Glu Glu Leu Gln Lys Glu Trp Thr
1 5 10 15

Gln Pro Arg Trp Glu Gly Ile Thr Arg Pro Tyr Ser Ala Glu Glu Val
20 25 30

Val Lys Leu Arg Gly Ser Val Asn Pro Glu Cys Thr Leu Ala Gln Leu
35 40 45

Gly Ala Ala Lys Met Trp Arg Leu Leu His Gly Glu Ala Lys Lys Gly
50 55 60

Tyr Ile Asn Ser Leu Gly Ala Leu Thr Gly Gly Gln Ala Leu Gln Gln
65 70 75 80

Ala Lys Ala Gly Ile Glu Ala Ile Tyr Leu Ser Gly Trp Gln Val Ala
85 90 95

Ala Asp Ala Asn Leu Ala Ser Ser Met Tyr Pro Asp Gln Ser Leu Tyr
100 105 110

Pro Ala Asn Ser Val Pro Ala Val Val Asp Arg Ile Asn Asn Thr Phe
115 120 125

Arg Arg Ala Asp Gln Ile Gln Trp Ala Ser Gly Ile Glu Pro Asn Asp
130 135 140

Pro Arg Tyr Val Asp Tyr Phe Leu Pro Ile Val Ala Asp Ala Glu Ala
145 150 155 160

Gly Phe Gly Gly Val Leu Asn Ala Phe Glu Leu Met Lys Ser Met Ile
165 170 175

Glu Ala Gly Ala Ala Ala Val His Phe Glu Asp Gln Leu Ala Ser Val
180 185 190

Lys Lys Cys Gly His Met Gly Gly Lys Val Leu Val Pro Thr Gln Glu
195 200 205

```
Ala Ile Gln Lys Leu Val Ala Ala Arg Leu Ala Ala Asp Val Met Gly
    210                 215                 220

Val Pro Thr Leu Val Ile Ala Arg Thr Asp Ala Asp Ala Ala Asp Leu
225                 230                 235                 240

Ile Thr Ser Asn Cys Asp Pro Tyr Asp Ser Ser Phe Ile Thr Gly Glu
                245                 250                 255

Arg Thr Ser Glu Gly Phe Tyr Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Asp Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Tyr Gln Phe Ile Thr Leu
            340                 345                 350

Ala Gly Ile His Ser Met Trp Phe Asn Met Phe Asp Leu Ala His Ala
        355                 360                 365

Tyr Ala Gln Gly Glu Gly Met Lys His Tyr Val Glu Lys Val Gln Gln
    370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Ala Ser Ser Val Thr Ala Leu Thr Gly Ser Thr Glu Glu Ser
            420                 425                 430

Gln Phe


<210> SEQ ID NO 33
<211> LENGTH: 434
<212> TYPE: PRT
<213> ORGANISM: Salmonella typhimurium

<400> SEQUENCE: 33

Met Lys Thr Arg Thr Gln Gln Ile Glu Glu Leu Gln Lys Glu Trp Thr
1               5                   10                  15

Gln Pro Arg Trp Glu Gly Ile Thr Arg Pro Tyr Ser Ala Glu Glu Val
            20                  25                  30

Val Lys Leu Arg Gly Ser Val Asn Pro Glu Cys Thr Leu Ala Gln Leu
        35                  40                  45

Gly Ala Ala Lys Met Trp Arg Leu Leu His Gly Glu Ala Lys Lys Gly
    50                  55                  60

Tyr Ile Asn Ser Leu Gly Ala Leu Thr Gly Gly Gln Ala Leu Gln Gln
65                  70                  75                  80

Ala Lys Ala Gly Ile Glu Ala Ile Tyr Leu Ser Gly Trp Gln Val Ala
                85                  90                  95

Ala Asp Ala Asn Leu Ala Ser Ser Met Tyr Pro Asp Gln Ser Leu Tyr
            100                 105                 110

Pro Ala Asn Ser Val Pro Ala Val Val Asp Arg Ile Asn Asn Thr Phe
        115                 120                 125

Arg Arg Ala Asp Gln Ile Gln Trp Ala Ser Gly Ile Glu Pro Asn Asp
    130                 135                 140
```

-continued

Pro Arg Tyr Val Asp Tyr Phe Leu Pro Ile Val Ala Asp Ala Glu Ala
145 150 155 160

Gly Phe Gly Gly Val Leu Asn Ala Phe Glu Leu Met Lys Ser Met Ile
165 170 175

Glu Ala Gly Ala Ala Ala Val His Phe Glu Asp Gln Leu Ala Ser Val
180 185 190

Lys Lys Cys Gly His Met Gly Gly Lys Val Leu Val Pro Thr Gln Glu
195 200 205

Ala Ile Gln Lys Leu Val Ala Ala Arg Leu Ala Ala Asp Val Met Gly
210 215 220

Val Pro Thr Leu Val Ile Ala Arg Thr Asp Ala Asp Ala Ala Asp Leu
225 230 235 240

Ile Thr Ser Asp Cys Asp Pro Tyr Asp Ser Gly Phe Ile Thr Gly Glu
245 250 255

Arg Thr Ser Glu Gly Phe Tyr Arg Thr His Ala Gly Ile Glu Gln Ala
260 265 270

Ile Ser Arg Gly Leu Ala Tyr Ala Pro Tyr Ala Asp Leu Val Trp Cys
275 280 285

Glu Thr Ser Thr Pro Asp Leu Glu Leu Ala Arg Arg Phe Ala Asp Ala
290 295 300

Ile His Ala Lys Tyr Pro Gly Lys Leu Leu Ala Tyr Asn Cys Ser Pro
305 310 315 320

Ser Phe Asn Trp Gln Lys Asn Leu Asp Asp Lys Thr Ile Ala Ser Phe
325 330 335

Gln Gln Gln Leu Ser Asp Met Gly Tyr Lys Tyr Gln Phe Ile Thr Leu
340 345 350

Ala Gly Ile His Ser Met Trp Phe Asn Met Phe Asp Leu Ala His Ala
355 360 365

Tyr Ala Gln Gly Glu Gly Met Lys His Tyr Val Glu Lys Val Gln Gln
370 375 380

Pro Glu Phe Ala Ala Ala Lys Asp Gly Tyr Thr Phe Val Ser His Gln
385 390 395 400

Gln Glu Val Gly Thr Gly Tyr Phe Asp Lys Val Thr Thr Ile Ile Gln
405 410 415

Gly Gly Ala Ser Ser Val Thr Ala Leu Thr Gly Ser Thr Glu Glu Ala
420 425 430

Gln Phe

<210> SEQ ID NO 34
<211> LENGTH: 434
<212> TYPE: PRT
<213> ORGANISM: Salmonella typhi

<400> SEQUENCE: 34

Met Lys Thr Arg Thr Gln Gln Ile Glu Glu Leu Gln Lys Glu Trp Thr
1 5 10 15

Gln Pro Arg Trp Glu Gly Ile Thr Arg Pro Tyr Ser Ala Glu Glu Val
20 25 30

Val Lys Leu Arg Gly Ser Val Asn Pro Glu Cys Thr Leu Ala Gln Leu
35 40 45

Gly Ala Ala Lys Met Trp Arg Leu Leu His Gly Glu Ala Lys Lys Gly
50 55 60

Tyr Ile Asn Ser Leu Gly Ala Leu Thr Gly Gly Gln Ala Leu Gln Gln
65 70 75 80

Ala Lys Ala Gly Ile Glu Ala Ile Tyr Leu Ser Gly Trp Gln Val Val

-continued

```
                85                  90                  95

Ala Asp Ala Asn Leu Ala Ser Ser Met Tyr Pro Asp Gln Ser Leu Tyr
            100                 105                 110

Pro Ala Asn Ser Val Pro Ala Val Val Asp Arg Ile Asn Asn Thr Phe
        115                 120                 125

Arg Arg Ala Asp Gln Ile Gln Trp Ala Ser Gly Ile Glu Pro Asn Asp
    130                 135                 140

Pro Arg Tyr Val Asp Tyr Phe Leu Pro Ile Val Ala Asp Ala Glu Ala
145                 150                 155                 160

Gly Phe Gly Gly Val Leu Asn Ala Phe Glu Leu Met Lys Ser Met Ile
                165                 170                 175

Glu Ala Gly Ala Ala Ala Val His Phe Glu Asp Gln Leu Ala Ser Val
            180                 185                 190

Lys Lys Cys Gly His Met Gly Gly Lys Val Leu Val Pro Thr Gln Glu
        195                 200                 205

Ala Ile Gln Lys Leu Val Ala Ala Arg Leu Ala Ala Asp Val Met Gly
    210                 215                 220

Val Pro Thr Leu Val Ile Ala Arg Thr Asp Ala Asp Ala Ala Asp Leu
225                 230                 235                 240

Ile Thr Ser Asp Cys Asp Pro Tyr Asp Ser Gly Phe Ile Thr Gly Glu
                245                 250                 255

Arg Thr Ser Glu Gly Phe Tyr Arg Thr His Ala Gly Ile Glu Gln Ala
            260                 265                 270

Ile Ser Arg Gly Leu Ala Tyr Ala Pro Tyr Ala Asp Leu Val Trp Cys
        275                 280                 285

Glu Thr Ser Thr Pro Asp Leu Glu Leu Ala Arg Arg Phe Ala Asp Ala
    290                 295                 300

Ile His Ala Lys Tyr Pro Gly Lys Leu Leu Ala Tyr Asn Cys Ser Pro
305                 310                 315                 320

Ser Phe Asn Trp Gln Lys Asn Leu Asp Asp Lys Thr Ile Ala Ser Phe
                325                 330                 335

Gln Gln Gln Leu Ser Asp Met Gly Tyr Lys Tyr Gln Phe Ile Thr Leu
            340                 345                 350

Ala Gly Ile His Ser Met Trp Phe Asn Met Phe Asp Leu Ala His Ala
        355                 360                 365

Tyr Ala Gln Gly Glu Gly Met Lys His Tyr Val Glu Lys Val Gln Gln
    370                 375                 380

Pro Glu Phe Ala Ala Ala Lys Asp Gly Tyr Thr Phe Val Ser His Gln
385                 390                 395                 400

Gln Glu Val Gly Thr Gly Tyr Phe Asp Lys Val Thr Thr Ile Ile Gln
                405                 410                 415

Gly Gly Ala Ser Ser Val Thr Ala Leu Thr Gly Ser Thr Glu Glu Ser
            420                 425                 430

Gln Phe


<210> SEQ ID NO 35
<211> LENGTH: 435
<212> TYPE: PRT
<213> ORGANISM: Erwina carotovora subsp. atroseptica

<400> SEQUENCE: 35

Met Thr Thr Ser Arg Thr Gln Gln Val Gln His Ile Glu Lys Glu Trp
1               5                   10                  15

Lys Thr Ala Arg Trp Glu Gly Ile Thr Arg Pro Tyr Ser Ala Glu Asp
            20                  25                  30
```

-continued

```
Val Ile Asn Leu Arg Gly Ser Val Asn Pro Glu Cys Thr Leu Ala Gln
        35                  40                  45

Leu Gly Ala Ala Arg Leu Trp Ser Leu Leu His Gly Glu Ala Arg Lys
    50                  55                  60

Gly Tyr Val Asn Cys Leu Gly Ala Leu Thr Gly Gly Gln Ala Leu Gln
65                  70                  75                  80

Gln Ala Lys Ala Gly Ile Glu Ala Ile Tyr Leu Ser Gly Trp Gln Val
                85                  90                  95

Ala Ala Asp Ala Asn Leu Ala Ser Ser Met Tyr Pro Asp Gln Ser Leu
            100                 105                 110

Tyr Pro Ala Asn Ser Val Pro Ala Val Ile Glu Arg Ile Asn Asn Thr
        115                 120                 125

Phe Arg Arg Ala Asp Gln Ile Gln Trp Ala Asn His Ile Glu Pro Gly
    130                 135                 140

Asp Lys Arg His Thr Asp Tyr Phe Leu Pro Ile Val Ala Asp Ala Glu
145                 150                 155                 160

Ala Gly Phe Gly Gly Val Leu Asn Ala Phe Glu Leu Met Lys Ser Met
                165                 170                 175

Ile Glu Ala Gly Ala Ala Ala Val His Phe Glu Asp Gln Leu Ala Ser
            180                 185                 190

Ala Lys Lys Cys Gly His Met Gly Gly Lys Val Leu Val Pro Thr Gln
        195                 200                 205

Glu Ala Val Gln Lys Leu Val Ala Ala Arg Leu Ala Ala Asp Val Met
    210                 215                 220

Gly Val Pro Thr Leu Val Val Ala Arg Thr Asp Ala Asp Ala Ala Asp
225                 230                 235                 240

Leu Met Thr Ser Asp Cys Asp Glu Tyr Asp Arg Asp Phe Ile Thr Gly
                245                 250                 255

Glu Arg Thr Val Glu Gly Phe Tyr Arg Thr Arg Ala Gly Ile Glu Gln
            260                 265                 270

Ala Ile Ser Arg Gly Leu Ala Tyr Ala Pro Tyr Ala Asp Leu Val Trp
        275                 280                 285

Cys Glu Thr Ser Thr Pro Asp Leu Ser Leu Ala Arg Arg Phe Ala Glu
    290                 295                 300

Ala Ile His Ala Lys Phe Pro Gly Lys Leu Leu Ala Tyr Asn Cys Ser
305                 310                 315                 320

Pro Ser Phe Asn Trp Lys Lys Asn Leu Asp Asp Ser Thr Ile Ala Arg
                325                 330                 335

Phe Gln Asp Glu Leu Ser Ala Met Gly Tyr Lys Tyr Gln Phe Ile Thr
            340                 345                 350

Leu Ala Gly Ile His Ser Met Trp Phe Asn Met Phe Asp Leu Ala His
        355                 360                 365

Ala Tyr Ala Gln Gly Glu Gly Met Arg His Tyr Val Glu Lys Val Gln
    370                 375                 380

Gln Pro Glu Phe Glu Ala Ile Lys Asp Gly Tyr Thr Phe Ser Ser His
385                 390                 395                 400

Gln Gln Glu Val Gly Thr Gly Tyr Phe Asp Lys Val Thr Asn Ile Ile
                405                 410                 415

Gln Gly Gly Gln Ser Ser Val Thr Ala Leu Thr Gly Ser Thr Glu Glu
            420                 425                 430

Gln Gln Phe
        435
```

<210> SEQ ID NO 36
<211> LENGTH: 1306
<212> TYPE: DNA
<213> ORGANISM: Artificial Sequence
<220> FEATURE:
<223> OTHER INFORMATION: Patent No. WO9218635

<400> SEQUENCE: 36
atgaaaaccc gtacacaaca aattgaagaa ttacagaaag agtggactca accgcgttgg 60
gaaggcatta ctcgcccata cagtgcggaa gatgtggtga aattacgcgg ttcagtcaat 120
cctgaatgca cgctggcgca actgggcgca gcgaaaatgt ggcgtctgct gcacggtgag 180
tcgaaaaaag gctacatcaa cagcctcggc gcactgactg gcggtcaggc gctgcaacag 240
gcgaaagcgg gtattgaagc agtctatctg tcgggatggc aggtagcggc ggacgctaac 300
ctggcggcca gcatgtatcc ggatcagtcg ctctatccgg caaactcggt gccagctgtg 360
gtggagcgga tcaacaacac cttccgtcgt gccgatcaga tccaatggtc cgcgggcatt 420
gagccgggcg atccgcgcta tgtcgattac ttcctgccga tcgttgccga tgcggaagcc 480
ggttttggcg gtgtcctgaa tgcctttgaa ctgatgaaag cgatgattga agccggtgca 540
gcggcagttc acttcgaaga tcagctggcg tcagtgaaga aatgcggtca catgggcggc 600
aaagttttag tgccaactca ggaagctatt cagaaactgg tcgcggcgcg tctggcagct 660
gacgtgacgg gcgttccaac cctgctggtt gcccgtaccg atgctgatgc ggcggatctg 720
atcacctccg attgcgaccc gtatgacagc gaatttatta ccggcgagcg taccagtgaa 780
ggcttcttcc gtactcatgc gggcattgag caagcgatca gccgtggcct ggcgtatgcg 840
ccatatgctg acctggtctg gtgtgaaacc tccacgccgg atctggaact ggcgcgtcgc 900
tttgcacaag ctatccacgc gaaatatccg ggcaaactgc tggcttataa ctgctcgccg 960
tcgttcaact ggcagaaaaa cctcgacgac aaaactattg ccagcttcca gcagcagctg 1020
tcggatatgg gctacaagtt ccagttcatc accctggcag gtatccacag catgtggttc 1080
aacatgtttg acctggcaaa cgcctatgcc cagggcgagg gtatgaagca ctacgttgag 1140
aaagtgcagc agccggaatt tgccgccgcg aaagatggct ataccttcgt atctcaccag 1200
caggaagtgg gtacaggtta cttcgataaa gtgacgacta ttattcaggg cggcgacgtc 1260
ttcagtcacc gcgctgaccg gctccactga agaatcgcag ttctaa 1306

<210> SEQ ID NO 37
<211> LENGTH: 1306
<212> TYPE: DNA
<213> ORGANISM: Escherichia coli

<400> SEQUENCE: 37
atgaaaaccc gtacacaaca aattgaagaa ttacagaaag agtggactca accgcgttgg 60
gaaggcatta ctcgcccata cagtgcggaa gatgtggtga aattacgcgg ttcagtcaat 120
cctgaatgca cgctggcgca actgggcgca gcgaaaatgt ggcgtctgct gcacggtgag 180
tcgaaaaaag gctacatcaa cagcctcggc gcactgactg gcggtcaggc gctgcaacag 240
gcgaaagcgg gtattgaagc agtctatctg tcgggatggc aggtagcggc ggacgctaac 300
ctggcggcca gcatgtatcc ggatcagtcg ctctatccgg caaactcggt gccagctgtg 360
gtggagcgga tcaacaacac cttccgtcgt gccgatcaga tccaatggtc cgcgggcatt 420
gagccgggcg atccgcgcta tgtcgattac ttcctgccga tcgttgccga tgcggaagcc 480
ggttttggcg gtgtcctgaa tgcctttgaa ctgatgaaag cgatgattga agccggtgca 540
gcggcagttc acttcgaaga tcagctggcg tcagtgaaga aatgcggtca catgggcggc 600

-continued

```
aaagttttag tgccaactca ggaagctatt cagaaactgg tcgcggcgcg tctggcagct    660

gacgtgacgg gcgttccaac cctgctggtt gcccgtaccg atgctgatgc ggcggatctg    720

atcacctccg attgcgaccc gtatgacagc gaatttatta ccggcgagcg taccagtgaa    780

ggcttcttcc gtactcatgc gggcattgag caagcgatca gccgtggcct ggcgtatgcg    840

ccatatgctg acctggtctg gtgtgaaacc tccacgccgg atctggaact ggcgcgtcgc    900

tttgcacaag ctatccacgc gaaatatccg ggcaaactgc tggcttataa ctgctcgccg    960

tcgttcaact ggcagaaaaa cctcgacgac aaaactattg ccagcttcca gcagcagctg   1020

tcggatatgg gctacaagtt ccagttcatc accctggcag gtatccacag catgtggttc   1080

aacatgtttg acctggcaaa cgcctatgcc cagggcgagg gtatgaagca ctacgttgag   1140

aaagtgcagc agccggaatt tgccgccgcg aaagatggct ataccttcgt atctcaccag   1200

caggaagtgg gtacaggtta cttcgataaa gtgacgacta ttattcaggg cggcgacgtc   1260

ttcagtcacc gcgctgaccg gctccactga agaatcgcag ttctaa                  1306
```

<210> SEQ ID NO 38
<211> LENGTH: 1305
<212> TYPE: DNA
<213> ORGANISM: Shigella flexneri

<400> SEQUENCE: 38

```
atgaaaaccc gtacacaaca aattgaagaa ttacagaaag agtggactca accgcgttgg     60

gaaggcatta ctcgcccata cagtgcggaa gatgtggtga aattacgcgg ttcagtcaat    120

cctgaatgca cgctggcgca actgggcgca gcgaaaatgt ggcgtctgct gcacggtgag    180

tcgaaaaaag gctacatcaa caacctcggt gcactgactg gcggtcaggc gctgcaacag    240

gcgaaagcgg gtattgaagc agtctatctg tcgggatggc aggtagcggc ggacgctaac    300

ctggcggcca gcatgtatcc ggatcagtcg ctctatccgg caaactcggt gccagctgtg    360

gtggagcgga tcaacaacac cttccgtcgt gccgatcaga tccaatggtc cgtgggcatt    420

gagccgggcg atccgcgcta tgtcgattac ttcctgccga tcgttgccga tgcggaagcc    480

ggttttggcg gtgtcctgaa tgcctttgaa ctgatgaaag cgatgattga agccggtgct    540

gcggcagttc acttcgaaga tcagctggcg tcagtgaaga aatgcggtca catgggcggc    600

aaagttttag tgccaactca ggaagctatt cagaaactgg tcgcggcgcg tctggcagct    660

gacgtgacgg gcgttccaac cctgctggtt gcacgtaccg atgctgatgc ggcggatctg    720

atcacctcag attgcgaccc gtatgacagc gaatttatta ccggcgagcg taccagtgaa    780

ggcttcttcc gtactcatgc gggcattgag caagcgatca gccgtggcct ggcgtatgcg    840

ccatatgctg acctggtctg gtgtgaaacc tccacgccgg atctggaact ggcgcgtcgc    900

tttgcacaag ctatccacgc gaaatatccg ggcaaactgc tggcttataa ctgctcgccg    960

tcgttcaact ggcagaaaaa cctcgacgac aaaactattg ccagcttcca gcagcagctg   1020

tcggatatgg gctacaagtt ccagttcatc accctagcag gtatccacag catgtggttt   1080

aacatgttcg acctggcaaa cgcttatgcg cagggcgaag gtatgaagca ctatgttgag   1140

aaagtgcagc agccggaatt tgccgccgcg aaagatggct ataccttcgt atctcaccag   1200

caggaagtgg gtacaggtta cttcgataaa gtgacgacta ttattcaggg cggcacgtct   1260

tcagtcaccg cgctgactgg ctccactgaa gaatcgcagt tctaa                   1305
```

<210> SEQ ID NO 39
<211> LENGTH: 1305

<212> TYPE: DNA
<213> ORGANISM: Shigella dysenteriae Sd197

<400> SEQUENCE: 39
atgaaaaccc gtacacaaca aattgaagaa ttacagaaag agtggactca accgcgttgg 60
gaaggcatta ctcgcccata cagcgcggaa gatgtggtga aattacgcgg ttcagtcaat 120
cctgaatgca cgctggcgca actgggcgcg gcgaaaatgt ggcgtctgct gcatggcgag 180
tcgaaaaaag gctacatcaa cagcctcggt gcactgactg gcggtcaggc gctgcaacag 240
gcgaaagcgg gtattgaagc agtctatctg tcgggatggc aggtagcggc ggacgctaac 300
ctggcggcca gcatgtatcc ggatcagtcg ctctacccgg cgaactcggt gccagcggtg 360
gtggagcgga tcaacaatac tttccgccgt gcggatcaga tccaatggtc cgcgggcatt 420
gagccgggcg atccgcgcta tgtcgattac ttcctgccga tcgttgccga tgcggaagcc 480
ggttttggcg gtgtcctgaa tgcctttgaa ctgatgaaag cgatgattga agccggtgca 540
gcggcagttc acttcgaaga tcagctggcg tcagtgaaga aatgcggtca catgggcggc 600
aaagttttgg tgccaactca agaagctatt cagaaactgg tcgcggcgcg tctggcagct 660
gacgtgacgg gcgttccaac cctactggtt gctcgaaccg atgccgatgc ggcggatctg 720
attacctccg attgcgaccc gtatgacagc gaatttatta ccggcgagcg taccagtgaa 780
ggcttcttcc gtactcatgc gggcattgag caagcgatca gccgtggcct ggcgtatgcg 840
ccatatgctg acctggtatg gtgtgaaacc tccacgccag acctggaact ggcgcgtcgc 900
tttgcacaag ctatccacgc gaaatatccg ggcaaactgc tggcttataa ctgctcgccg 960
tcgttcaact ggcagaaaaa cctcgacgac aaaactattg ctagcttcca gcagcagctg 1020
tcggatatgg gctacaagtt ccagttcatc accctggcag gtatccacag catgtggttc 1080
aacatgtttg acctggcaaa cgcctatgcc cagggcgagg gtatgaagca ctatgttgag 1140
aaagtgcagc agccggaatt tgccgccgcg aaagatggct ataccttcgt atctcaccag 1200
caggaagtgg gtacaggtta cttcgataaa gtgacgacta ttattcaggg cggcacgtct 1260
tcagtcaccg cgctgaccgg ctccactgaa gaatcgcagt tctaa 1305

<210> SEQ ID NO 40
<211> LENGTH: 1298
<212> TYPE: DNA
<213> ORGANISM: Shigella boydii Sb227

<400> SEQUENCE: 40
atgaaaaccc gtacacaaca aattgaagaa ttacagaaag agtggactca accgcgttgg 60
gaaggcatta ctcgcccata cagcgcggaa gatgtggtga aattacgcga ttcagtcaat 120
cctgaatgca ccctggcgca actgggcgcg gcgagaatgt ggcgtctgct gcatggcgag 180
tcgaaaaaag ctacatcaac agcctcggtg cactgactgg cggtcaggcg ctgcaacagg 240
cgaaagcggg tattgaagca gtctatctgt cgggatggca ggtagcggcg gacgctaacc 300
tggcggccag catgtatccg gatcagtcgc tctatccggc aaactcggtg ccagctgtgg 360
tggagcggat caacaatact ttccgccgtg cggatcagat ccaatggtcc gcgggcattg 420
agccgggcga tccgcgctat gtcgattact tcctgccgat cgttgccgat gcggaagccg 480
gttttggcgg tgtcctgaat gcctttgaac tgatgaaagc gatgattgaa gccggtgcag 540
cggcagttca cttcgaagat cagctggcgt cagtgaagaa atgcggtcac atgggcggca 600
aagttttagt gccaactcaa gaagctattc agaaactggt cgcggcgcgt ctggcagctg 660
acgtgacggg cgttccaacc ctactggttg ctcgtaccga tgccgcggat ctgatcacct 720
ccgattgcga cccgtatgac agcgaattta ttaccggcga gcgtaccagt gaaggcttct 780
tccgtactca tgcgggcatt gagcaagcga tcagccgtgg cctggcgtat gcgccatatg 840
ctgacctggt ctggtgtgaa acctccacgc cggatctgga actggcgcgt cgctttgcac 900
aagctatcca cgcgaaatat ccgggcaaac tgctggctta taactgctcg ccgtcgttca 960
actggcagaa aaacctcgac gacaaaacta ttgccagctt ccagcagcag ctgtcggata 1020
tgggctacaa gttccagttc atcaccctgg caggtatcca cagcatgtgg ttcaacatgt 1080
ttgacctggc aaacgcctat gaccagggcg agggtatgaa gcactacgtt gagaaagtgc 1140
agcagccgga atttgccgcc gcgaaagatg gctatacctt cgtatctcac cagcaggaag 1200
tgggtacagg ttacttcgat aaagtgacga ctattattca gggcggcacg tcttcagtca 1260
ccgcgctgac cggctccact gaagaatcgc agttctaa 1298

<210> SEQ ID NO 41
<211> LENGTH: 1305
<212> TYPE: DNA
<213> ORGANISM: Escherichia coli 0157:H7

<400> SEQUENCE: 41
atgaaaaccc gtacacaaca aattgaagaa ttacagaaag agtggactca accgcgttgg 60
gaaggaatta ctcgcccata cagcgcggaa gatgtggtga aattacgcgg ttcagtcaat 120
cctgaatgca cgctggcgca actgggcgcg gcgaaaatgt ggcgtctgct gcatggcgag 180
tcgaaaaaag gctacatcaa cagcctcggt gcactgactg gcggtcaggc gctgcaacag 240
gcgaaagcgg gtattgaagc ggtctatctg tcgggatggc aggtagcggc ggacgctaac 300
ctggcggcca gcatgtatcc ggatcagtcg ctctatccgg caaactcggt gccagctgtg 360
gtggagcgga tcaacaacac tttccgccgt gcggatcaga tccaatggtc cgcgggcatt 420
gagccgggcg atccgcgcta tgtcgattac ttcctgccga tcgttgccga cgcggaagcc 480
ggttttggcg gtgtcctgaa tgcctttgaa ctgatgaaag cgatgattga agccggtgca 540
gcggcagttc acttcgaaga tcagctggcg tcagtgaaga aatgcggtca catgggcggc 600
aaagttttgg tgccaactca ggaagctatt cagaaactgg tcgcggcgcg tctggcagct 660
gacgtgacgg gcgttccaac cctgctggtt gcacgtaccg atgctgatgc ggcggatctg 720
atcacctccg attgcgaccc gtatgacagc gaatttatta ccggcgagcg taccagtgaa 780
ggcttcttcc gtactcatgc gggcattgag caagcgatca gccgtggcct ggcgtatgcg 840
ccatatgctg acctggtatg gtgtgaaacc tccacgccgg atctggaact ggcgcgtcgc 900
tttgcggaag ctatccacgc gaaatatccg ggcaaactgc tggcttataa ctgctcgccg 960
tcgttcaact ggcagaaaaa cctcgacgac aacactattg ccagcttcca gcagcagctg 1020
tcggatatgg gctacaagtt ccagttcatc accctggcag gtatccacag catgtggttc 1080
aacatgtttg atctggcaaa cgcctatgcc cagggcgagg gtatgaagca ctatgttgag 1140
aaagtgcagc agccggaatt cgccgccgcg aaagatggct acaccttcgt atctcaccag 1200
caggaagtgg gtacaggtta cttcgataaa gtgacgacca ttattcaggg cggcacgtcg 1260
tcggttaccg cgctgactgg ctccaccgaa gaatcgcagt tctaa 1305

<210> SEQ ID NO 42
<211> LENGTH: 533
<212> TYPE: PRT
<213> ORGANISM: Escherichia coli

<400> SEQUENCE: 42

```
Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Gln Asp Ile Asp Asn Gly Thr Leu Pro
    50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Arg Val Glu Ile Thr Gly
                85                  90                  95

Pro Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Gln Ala Leu Leu Ala Lys Gly Ser Gly
        195                 200                 205

Pro Tyr Phe Tyr Leu Pro Lys Thr Gln Ser Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
    290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
        355                 360                 365

Pro Gly Leu Ala Asp Thr Ala Met Ala Val Phe Asn Asp Ile Leu Gly
    370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
```

```
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510

Gln Ile Thr Thr Ser Asp Glu Leu Ile Asp Phe Leu Thr Leu Pro Gly
        515                 520                 525

Tyr Arg Leu Leu Ala
    530


<210> SEQ ID NO 43
<211> LENGTH: 533
<212> TYPE: PRT
<213> ORGANISM: Escherichia coli o157:h7

<400> SEQUENCE: 43

Met Thr Glu Gln Ala Thr Thr Thr Asp Glu Leu Ala Phe Ile Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Gln Asp Ile Asp Asn Gly Thr Leu Pro
    50                  55                  60

Asp Phe Ile Ser Glu Thr Ala Ser Ile Arg Asp Ala Asp Trp Lys Ile
65                  70                  75                  80

Arg Gly Ile Pro Ala Asp Leu Glu Asp Arg Arg Val Glu Ile Thr Gly
                85                  90                  95

Ser Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Gln Ala Leu Leu Ala Lys Gly Ser Gly
        195                 200                 205

Pro Tyr Phe Tyr Leu Pro Lys Thr Gln Ser Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
```

```
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
    290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
        355                 360                 365

Pro Gly Leu Ala Asp Thr Ala Met Ala Val Phe Asn Asp Ile Leu Gly
    370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Gln Lys Thr Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Asp Asp Ala Ala Arg Leu Met Glu
            500                 505                 510

Gln Ile Thr Thr Ser Asp Glu Leu Ile Asp Phe Leu Thr Leu Pro Gly
        515                 520                 525

Tyr Arg Leu Leu Ala
    530


<210> SEQ ID NO 44
<211> LENGTH: 533
<212> TYPE: PRT
<213> ORGANISM: Shigella boydii

<400> SEQUENCE: 44

Met Thr Glu Gln Ala Thr Thr Thr Asp Glu Leu Ala Phe Thr Arg Pro
1               5                   10                  15

Tyr Gly Glu Gln Glu Lys Gln Ile Leu Thr Ala Glu Ala Val Glu Phe
            20                  25                  30

Leu Thr Glu Leu Val Thr His Phe Thr Pro Gln Arg Asn Lys Leu Leu
        35                  40                  45

Ala Ala Arg Ile Gln Gln Gln Gln Asp Ile Asp Asn Gly Thr Leu Pro
    50                  55                  60

Asp Phe Ile Ser Glu Thr Ala Ser Ile Cys Asp Ala Asp Trp Lys Ile
65                  70                  75                  80

Arg Gly Ile Pro Ala Asp Leu Glu Asp Arg Arg Val Glu Ile Thr Gly
                85                  90                  95

Pro Val Glu Arg Lys Met Val Ile Asn Ala Leu Asn Ala Asn Val Lys
```

-continued

```
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asn Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Gln Ala Leu Leu Ala Lys Gly Ser Gly
        195                 200                 205

Pro Tyr Phe Tyr Leu Pro Lys Thr Gln Ser Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn Tyr Pro Asp Arg Val Leu Pro Asp Arg Gln Ala Val Thr Met Asp
    290                 295                 300

Lys Pro Phe Leu Asn Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Glu Glu His Asn Asn Gln Val Leu Asn Lys Val Lys Ala Asp
            340                 345                 350

Lys Ser Leu Glu Ala Asn Asn Gly His Asp Gly Thr Trp Ile Ala His
        355                 360                 365

Pro Gly Leu Ala Asp Thr Ala Met Ala Val Phe Asn Asp Ile Leu Gly
    370                 375                 380

Ser Arg Lys Asn Gln Leu Glu Val Met Arg Glu Gln Asp Ala Pro Ile
385                 390                 395                 400

Thr Ala Asp Gln Leu Leu Ala Pro Cys Asp Gly Glu Arg Thr Glu Glu
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Gln Lys Met Leu Ser Asn Gly Lys Pro Val Thr Lys Ala Leu Phe Arg
465                 470                 475                 480

Gln Met Leu Gly Glu Glu Met Lys Val Ile Ala Ser Glu Leu Gly Glu
                485                 490                 495

Glu Arg Phe Ser Gln Gly Arg Phe Gly Asp Ala Ala Arg Leu Met Glu
            500                 505                 510

Gln Ile Thr Thr Ser Asp Glu Leu Ile Asp Phe Leu Thr Leu Pro Gly
        515                 520                 525
```

```
Tyr Cys Leu Leu Ala
    530


<210> SEQ ID NO 45
<211> LENGTH: 539
<212> TYPE: PRT
<213> ORGANISM: Escherichia coli (4.1.3.2)

<400> SEQUENCE: 45

Met Thr Arg Ser Cys Thr Met Thr Glu Gln Ala Thr Thr Ile Asp Glu
1               5                   10                  15

Leu Ala Phe Thr Arg Pro Tyr Gly Glu Gln Glu Lys Gln Ile Leu Thr
            20                  25                  30

Ala Glu Ala Val Glu Phe Leu Thr Glu Leu Val Thr His Phe Thr Pro
        35                  40                  45

Gln Arg Asn Lys Leu Leu Ala Ala Arg Ile Gln Gln Gln Gln Asp Ile
    50                  55                  60

Asp Asn Gly Met Leu Pro Asp Phe Ile Ser Glu Thr Ala Ser Ile Arg
65                  70                  75                  80

Tyr Ala Asp Trp Lys Ile Arg Gly Ile Pro Ser Asp Leu Glu Asp Arg
                85                  90                  95

Arg Val Glu Ile Thr Gly Pro Val Glu Arg Lys Met Val Ile Asn Ala
            100                 105                 110

Leu Asn Ala Asn Val Lys Val Phe Met Ala Asp Phe Glu Asp Ser Leu
        115                 120                 125

Ala Pro Asp Trp Asn Lys Val Ile Asp Gly Gln Ile Asn Leu Arg Asp
    130                 135                 140

Ala Val Asn Gly Thr Ile Ser Tyr Ser Asn Glu Ala Gly Lys Ile Tyr
145                 150                 155                 160

Gln Leu Lys Pro Asn Pro Ala Val Leu Ile Cys Arg Val Arg Gly Leu
                165                 170                 175

His Leu Pro Glu Lys His Val Thr Trp Arg Gly Glu Thr Ile Pro Gly
            180                 185                 190

Ser Leu Phe Asp Phe Ala Leu Tyr Phe Phe His Asn Tyr Gln Ala Leu
        195                 200                 205

Leu Ala Lys Gly Ser Gly Pro Tyr Phe Tyr Leu Pro Lys Thr Gln Ser
    210                 215                 220

Trp Gln Glu Ala Ala Trp Trp Ser Glu Val Phe Ser Tyr Ala Glu Asp
225                 230                 235                 240

Arg Phe Asn Leu Pro Arg Gly Thr Ile Lys Ala Thr Leu Leu Ile Glu
                245                 250                 255

Thr Leu Pro Ala Val Phe Gln Met Asp Glu Ile Leu His Ala Leu Arg
            260                 265                 270

Asp His Ile Val Gly Leu Asn Cys Gly Arg Trp Asp Tyr Ile Phe Ser
        275                 280                 285

Tyr Ile Lys Thr Leu Lys Asn Tyr Pro Asp Arg Val Leu Pro Asp Arg
    290                 295                 300

Gln Ala Val Thr Met Asp Lys Pro Phe Leu Asn Ala Tyr Ser Arg Leu
305                 310                 315                 320

Leu Ile Lys Thr Cys His Lys Arg Gly Ala Phe Ala Met Gly Gly Met
                325                 330                 335

Ala Ala Phe Ile Pro Ser Lys Asp Glu Glu Arg Asn Asn Gln Val Leu
            340                 345                 350

Asp Lys Val Lys Ala Asp Lys Ser Leu Glu Ala Asn Asn Gly His Asp
        355                 360                 365
```

-continued

```
Gly Thr Trp Ile Ala His Pro Gly Leu Ala Asp Thr Ala Met Ala Val
    370                 375                 380

Phe Asn Asp Ile Leu Gly Ser Arg Lys Asn Gln Leu Glu Val Met Arg
385                 390                 395                 400

Glu Gln Asp Ala Pro Ile Thr Ala Asp Gln Leu Leu Ala Pro Cys Ala
                405                 410                 415

Gly Glu Arg Thr Glu Glu Gly Met Arg Ala Asn Ile Arg Val Ala Val
            420                 425                 430

Gln Tyr Ile Glu Ala Trp Ile Ser Gly Asn Gly Cys Val Pro Ile Tyr
        435                 440                 445

Gly Leu Met Glu Asp Ala Ala Thr Ala Glu Ile Ser Ser Thr Ser Ile
    450                 455                 460

Trp Gln Trp Ile His His Gln Lys Thr Leu Ser Asn Gly Lys Pro Val
465                 470                 475                 480

Thr Lys Ala Leu Phe Arg Gln Met Leu Gly Glu Glu Met Lys Val Ile
                485                 490                 495

Ala Ser Glu Leu Gly Glu Glu Arg Phe Ser His Gly Arg Phe Asp Asp
            500                 505                 510

Ala Ala Arg Leu Met Glu Gln Ile Thr Thr Ser Asp Glu Leu Ile Asp
        515                 520                 525

Phe Leu Thr Leu Pro Gly Tyr Arg Leu Leu Ala
    530                 535


<210> SEQ ID NO 46
<211> LENGTH: 533
<212> TYPE: PRT
<213> ORGANISM: Salmonella typhimurium

<400> SEQUENCE: 46

Met Asn Pro Gln Ala Thr Thr Thr Asp Glu Leu Thr Phe Thr Arg Pro
1               5                   10                  15

Gln Gly Glu Leu Glu Lys Gln Val Leu Thr Ala Glu Ala Val Glu Phe
            20                  25                  30

Leu Thr Glu Leu Val Thr Arg Phe Thr Pro Lys Arg Asn Lys Leu Leu
        35                  40                  45

Ala Ala Arg Ile Gln Gln Gln Gln Asp Ile Asp Asn Gly Lys Leu Pro
    50                  55                  60

Asp Phe Ile Ser Glu Thr Thr Ser Ile Arg Glu Ser Asn Trp Gln Ile
65                  70                  75                  80

Arg Gly Ile Pro Ala Asp Leu Gln Asp Arg Arg Val Glu Ile Thr Gly
                85                  90                  95

Pro Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asp Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Lys Ala Leu Leu Ala Lys Gly Ser Gly
        195                 200                 205
```

-continued

Pro Tyr Phe Tyr Leu Pro Lys Thr Gln Ala Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn His Pro Asp Arg Val Leu Pro Asp Arg Gln Val Val Thr Met Asp
    290                 295                 300

Lys Pro Phe Leu Ser Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Val Glu Arg Asn Asn Gln Val Leu Ala Lys Val Lys Ala Asp
            340                 345                 350

Lys Ala Leu Glu Ala Asn Asn Gly His Asp Gly Thr Trp Ile Ala His
        355                 360                 365

Pro Gly Leu Ala Asp Thr Ala Met Ala Val Phe Asn Glu Val Leu Gly
    370                 375                 380

Glu His Lys Asn Gln Leu Phe Ile Thr Arg Asp Glu Asp Ala Pro Ile
385                 390                 395                 400

Thr Ala Glu Gln Leu Leu Glu Pro Cys Glu Gly Glu Arg Thr Glu Ala
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Glu Lys Thr Leu Ser Asn Gly Lys Pro Val Thr Lys Thr Leu Phe Arg
465                 470                 475                 480

Glu Met Leu Ala Glu Glu Met Arg Val Ile Gln Asp Glu Leu Gly Glu
                485                 490                 495

His Arg Tyr Ser Ser Gly Arg Phe Asp Asp Ala Ala Arg Leu Met Glu
            500                 505                 510

Gln Ile Thr Thr Ser Asp Asp Leu Ile Asp Phe Leu Thr Leu Pro Gly
        515                 520                 525

Tyr Arg Leu Leu Ala
    530

<210> SEQ ID NO 47
<211> LENGTH: 533
<212> TYPE: PRT
<213> ORGANISM: Salmonella choleraesuis

<400> SEQUENCE: 47

Met Asn Pro Gln Ala Thr Thr Thr Asp Glu Leu Thr Phe Thr Arg Pro
1               5                   10                  15

Gln Gly Glu Leu Glu Lys Gln Val Leu Thr Ala Glu Ala Val Glu Phe
            20                  25                  30

Leu Thr Glu Leu Val Thr Arg Phe Thr Pro Lys Arg Asn Lys Leu Leu
        35                  40                  45

-continued

```
Ala Ala Arg Ile Gln Gln Gln Gln Asp Ile Asp Asn Gly Lys Leu Pro
    50                  55                  60

Asp Phe Ile Ser Glu Thr Thr Ser Ser Arg Glu Ser Asn Trp Gln Ile
65                  70                  75                  80

Arg Gly Ile Pro Ala Asp Leu Gln Asp Arg Arg Val Glu Ile Thr Gly
                85                  90                  95

Pro Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Ile Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asp Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Lys Ala Leu Leu Ala Lys Gly Ser Gly
        195                 200                 205

Pro Tyr Phe Tyr Leu Pro Lys Thr Gln Ala Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Gly Leu
            260                 265                 270

Asn Cys Gly Arg Trp Asp Tyr Ile Phe Ser Tyr Ile Lys Thr Leu Lys
        275                 280                 285

Asn His Pro Asp Arg Val Leu Pro Asp Arg Gln Val Val Thr Met Asp
    290                 295                 300

Lys Pro Phe Leu Ser Ala Tyr Ser Arg Leu Leu Ile Lys Thr Cys His
305                 310                 315                 320

Lys Arg Gly Ala Phe Ala Met Gly Gly Met Ala Ala Phe Ile Pro Ser
                325                 330                 335

Lys Asp Val Glu Arg Asn Asn Gln Val Leu Ala Lys Val Lys Ala Asp
            340                 345                 350

Lys Ala Leu Glu Ala Asn Asn Gly His Asp Gly Thr Trp Ile Ala His
        355                 360                 365

Pro Gly Leu Ala Asp Thr Ala Met Ala Val Phe Asn Glu Val Leu Gly
    370                 375                 380

Glu His Lys Asn Gln Leu Phe Ile Thr Arg Asp Glu Asp Ala Pro Ile
385                 390                 395                 400

Thr Ala Glu Gln Leu Leu Glu Pro Cys Glu Gly Glu Arg Thr Glu Ala
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Glu Lys Thr Leu Ser Asn Gly Lys Pro Val Thr Lys Thr Leu Phe Arg
465                 470                 475                 480
```

```
Glu Met Leu Ala Glu Glu Met Arg Val Ile Gln Asp Glu Leu Gly Glu
                485                 490                 495

His Arg Tyr Ser Ser Gly Arg Phe Asp Asp Ala Ala Arg Leu Met Glu
            500                 505                 510

Gln Ile Thr Thr Ser Asp Asp Leu Ile Asp Phe Leu Thr Leu Pro Gly
        515                 520                 525

Tyr Arg Leu Leu Ala
    530


<210> SEQ ID NO 48
<211> LENGTH: 533
<212> TYPE: PRT
<213> ORGANISM: Salmonella paratyphi-a

<400> SEQUENCE: 48

Met Asn Pro Gln Ala Thr Thr Thr Asp Glu Leu Thr Phe Thr Arg Pro
1               5                   10                  15

Gln Gly Glu Leu Glu Lys Gln Val Leu Thr Ala Glu Ala Val Glu Phe
            20                  25                  30

Leu Thr Glu Leu Val Thr Arg Phe Thr Pro Lys Arg Asn Lys Leu Leu
        35                  40                  45

Ala Ala Arg Ile Gln Gln Gln Gln Asp Ile Asp Asn Gly Lys Leu Pro
    50                  55                  60

Asp Phe Ile Ser Glu Thr Thr Ser Ile Arg Glu Ser Asn Trp Gln Ile
65                  70                  75                  80

Arg Gly Ile Pro Ala Asp Leu Gln Asp Arg Arg Val Glu Ile Thr Gly
                85                  90                  95

Pro Val Glu Arg Lys Met Val Ile Asn Ala Leu Asn Ala Asn Val Lys
            100                 105                 110

Val Phe Met Ala Asp Phe Glu Asp Ser Leu Ala Pro Asp Trp Asn Lys
        115                 120                 125

Val Met Asp Gly Gln Ile Asn Leu Arg Asp Ala Val Asn Gly Thr Ile
    130                 135                 140

Ser Tyr Thr Asn Glu Ala Gly Lys Ile Tyr Gln Leu Lys Pro Asp Pro
145                 150                 155                 160

Ala Val Leu Ile Cys Arg Val Arg Gly Leu His Leu Pro Glu Lys His
                165                 170                 175

Val Thr Trp Arg Gly Glu Ala Ile Pro Gly Ser Leu Phe Asp Phe Ala
            180                 185                 190

Leu Tyr Phe Phe His Asn Tyr Lys Ala Leu Leu Ala Lys Gly Ser Gly
        195                 200                 205

Pro Tyr Phe Tyr Leu Pro Lys Thr Gln Ala Trp Gln Glu Ala Ala Trp
    210                 215                 220

Trp Ser Glu Val Phe Ser Tyr Ala Glu Asp Arg Phe Asn Leu Pro Arg
225                 230                 235                 240

Gly Thr Ile Lys Ala Thr Leu Leu Ile Glu Thr Leu Pro Ala Val Phe
                245                 250                 255

Gln Met Asp Glu Ile Leu His Ala Leu Arg Asp His Ile Val Ser Leu
            260                 265                 270

Asn Cys Gly Arg Trp Asp Tyr Ile Phe Ser Tyr Ile Lys Thr Leu Lys
        275                 280                 285

Asn His Pro Asp Arg Val Leu Pro Asp Arg Gln Val Val Thr Met Asp
    290                 295                 300

Lys Pro Phe Leu Ser Ala Tyr Ser Arg Leu Leu Ile Lys Ala Cys His
305                 310                 315                 320
```

```
Lys Arg Gly Ala Phe Ala Met Gly Gly Met Ala Ala Phe Ile Pro Ser
                325                 330                 335

Lys Asp Val Glu Arg Asn Asn Gln Val Leu Ala Lys Val Lys Ala Asp
            340                 345                 350

Lys Ala Leu Glu Ala Asn Asn Gly His Asp Gly Thr Trp Ile Ala His
        355                 360                 365

Pro Gly Leu Ala Asp Thr Ala Met Ala Val Phe Asn Glu Val Leu Gly
    370                 375                 380

Glu His Lys Asn Gln Leu Phe Ile Thr Arg Asp Glu Asp Ala Pro Ile
385                 390                 395                 400

Thr Ala Glu Gln Leu Leu Glu Pro Cys Glu Gly Glu Arg Thr Glu Ala
                405                 410                 415

Gly Met Arg Ala Asn Ile Arg Val Ala Val Gln Tyr Ile Glu Ala Trp
            420                 425                 430

Ile Ser Gly Asn Gly Cys Val Pro Ile Tyr Gly Leu Met Glu Asp Ala
        435                 440                 445

Ala Thr Ala Glu Ile Ser Arg Thr Ser Ile Trp Gln Trp Ile His His
    450                 455                 460

Glu Lys Thr Leu Ser Asn Gly Lys Pro Val Thr Lys Ala Leu Phe Arg
465                 470                 475                 480

Glu Met Leu Ala Glu Glu Met Arg Val Ile Gln Asp Glu Leu Gly Glu
                485                 490                 495

His Arg Tyr Ser Ser Gly Arg Phe Asp Asp Ala Ala Arg Leu Met Glu
            500                 505                 510

Gln Ile Thr Thr Ser Asp Asp Leu Ile Asp Phe Leu Thr Leu Pro Gly
        515                 520                 525

Tyr Arg Leu Leu Ala
    530
```

<210> SEQ ID NO 49
<211> LENGTH: 1602
<212> TYPE: DNA
<213> ORGANISM: Escherichia coli 0157:h7

<400> SEQUENCE: 49

```
atgactgaac aggcaacaac aaccgatgaa ctggctttca taaggccgta tggcgagcag     60

gagaagcaaa ttcttactgc cgaagcggta gaatttctga ctgagctggt gacgcatttt    120

acgccacaac gcaataaact tctggcagcg cgcattcagc agcagcaaga tattgataac    180

ggaacgttgc ctgattttat ttcggaaaca gcttccattc gtgatgctga ctggaaaatt    240

cgcgggattc ctgcggactt agaagatcgc cgcgtagaga ttaccggatc cgtagagcgc    300

aagatggtga tcaacgcgct caacgccaat gtgaaagtct ttatggccga tttcgaagat    360

tcactggcac cagactggaa caaagtgatc gacgggcaaa ttaacctgcg tgatgcggtt    420

aacggcacca tcagttacac caatgaagca ggcaaaattt accagctcaa gcccaatcca    480

gcggttttga tttgtcgggt acgcggtctg cacttgccgg aaaaacatgt cacctggcgt    540

ggtgaggcaa tccccggcag cctgtttgat tttgcgctct atttcttcca caactatcag    600

gcactgttgg caaagggcag tggtccctat ttctatctgc cgaaaaccca gtcctggcag    660

gaagcggcct ggtggagcga agtcttcagc tatgcagaag atcgctttaa tctgccgcgc    720

ggcaccatca aggcgacgtt gctgattgaa acgctgcccg ccgtgttcca gatggatgaa    780

atccttcacg cgctgcgtga ccatattgtt ggtctgaact gcggtcgttg ggattacatc    840

ttcagctata tcaaaacgtt gaaaaactat cccgatcgcg tcctgccaga cagacaggca    900
```

gtaacgatgg ataaaccatt cctgaatgct tactcacgcc tgttgattaa aacctgccat 960
aaacgcggtg cttttgcgat gggcggcatg gcggcgttta ttccgagcaa agatgaagag 1020
cacaataacc aggtgctcaa caaagtaaaa gcggataaat cgctggaagc caataacggt 1080
cacgatggca catggatcgc tcacccaggc cttgcggaca cggcaatggc ggtattcaac 1140
gacattctcg gctcccgtaa aaatcagctt gaagtgatgc gcgaacaaga cgcgccgatt 1200
actgccgatc agctgctggc accttgtgat ggtgaacgca ccgaagaagg tatgcgcgcc 1260
aacattcgcg tggctgtgca gtacatcgaa gcatggatct ccggcaacgg ctgcgtgccg 1320
atttatggcc tgatggaaga tgcggcgacg gctgaaattt cccgtacctc aatctggcag 1380
tggatccatc atcaaaaaac gttgagcaat ggcaaaccgg taactaaagc cttgttccgc 1440
cagatgctgg gcgaagagat gaaagtcatt gccagcgaac tgggcgaaga acgtttctcc 1500
caggggcgtt ttgacgatgc cgcacgcttg atggaacaga tcaccacttc cgatgagtta 1560
attgatttcc tgaccctgcc aggctaccgc ctgttagcgt aa 1602

<210> SEQ ID NO 50
<211> LENGTH: 1602
<212> TYPE: DNA
<213> ORGANISM: Shigella boydii Sb227

<400> SEQUENCE: 50
atgactgaac aggcaacaac aaccgatgaa ctggctttca caaggccgta tggcgagcag 60
gagaagcaaa ttcttactgc cgaagcggta gaatttctga ctgagctggt gacgcatttt 120
acgccacaac gaaataaact tctggcagcg cgcattcagc agcagcaaga tattgataac 180
ggaacgttgc ctgattttat ttcggaaaca gcttccattt gcgatgctga ttggaaaatt 240
cgcgggattc ctgcggactt agaagaccgc cgcgtagaga taactggccc ggtagagcgc 300
aagatggtga tcaacgcgct caacgccaat gtgaaagtct ttatggccga tttcgaagat 360
tcactggccc cggactggaa caaagtgatc gacgggcaaa ttaacctgcg tgatgcagtt 420
aacggtacca tcagctatac caatgaagca ggcaaaattt accagctcaa gcccaatcca 480
gcggttttga tttgtcgggt acgcggtctg cacttgccgg aaaaacatgt cacctggcgt 540
ggtgaggcaa tccccggcag cctgtttgat tttgcgctct atttcttcca caactatcag 600
gctctgttgg caaagggcag tggtccctat ttctatctgc cgaaaaccca gtcctggcag 660
gaagcggcct ggtggagcga agtcttcagc tatgcagaag atcgctttaa tctgccgcgc 720
ggcaccatca aggcgacgtt gctgattgaa acgctgcccg ccgtgttcca gatggatgaa 780
atccttcacg cgctgcgtga ccatattgtt ggtctgaact gcggtcgttg ggattacatc 840
ttcagctata tcaaaacgtt gaaaaactat cccgatcgcg tcctgccaga cagacaggca 900
gtgacgatgg ataaaccatt cctgaatgct tactcacgcc tgttgattaa aacctgccat 960
aaacgcggtg cttttgcgat gggcggcatg gcggcgttta ttccgagcaa agatgaagag 1020
cacaataacc aggtgctcaa caaagtaaaa gcggataaat cgctggaagc caataacggt 1080
cacgatggca catggatcgc tcacccaggc cttgcggata cggcaatggc ggtattcaac 1140
gacattctcg gctcccgtaa aaatcagctt gaagtgatgc gcgaacaaga cgcgccgatt 1200
actgccgatc agctactggc accttgtgac ggtgaacgca ccgaagaagg tatgcgcgca 1260
aatattcgcg tagccgtgca gtacatcgaa gcgtggatct ctggcaacgg ctgtgtgccg 1320
atttatggcc tgatggaaga tgcggcgacg gctgaaattt cccgtacctc aatctggcag 1380
tggatccatc atcaaaaaat gttgagcaat ggcaaaccgg taactaaagc cttgttccgc 1440

-continued

```
cagatgctgg gcgaagagat gaaagtcatt gccagcgaac tgggcgaaga acgtttctcc   1500

caggggcgtt ttggcgatgc cgcacgcttg atggaacaga tcaccacttc cgatgagtta   1560

attgatttcc tgaccctgcc aggctactgc ctgttagcgt aa                       1602


<210> SEQ ID NO 51
<211> LENGTH: 1602
<212> TYPE: DNA
<213> ORGANISM: Shigella flexneri

<400> SEQUENCE: 51

atgactgaac aggcaacaac aaccgatgaa ctggctttca caaggccgta tggcgagcag     60

gagaagcaaa ttcttactgc cgaagcggta gaatttctga ctgagctggt gacgcatttt    120

acgccacaac gcaataaact tctggcagcg cgcattcagc agcagcaaga tattgataac    180

ggaacgttgc ctgattttat ttcggaaacg gcttccattc gcgatgctga ttggaaaatt    240

cgcgggattc ctgcggactt agaagaccgc cgcgtagaga taactggccc ggtagagcgc    300

aagatggtga tcaacgcact gaacgccaat gtgaaagtct ttatggccga tttcgaagat    360

tcactggcac cagactggaa caaagtgatc gacgggcaaa ttaacctgcg cgatgcggtt    420

aacggtacca tcagctatac caatgaagca ggcaaaattt atcagctcaa gcccaatcca    480

gcggttttga tttgtcgggt acgcggtctg cacttgccgg aaaaacatgt cacctggcgt    540

ggtgaggcaa tccccggtag cctgtttgat tttgcgctct atttcttcca caactatcag    600

gcactgttgg caaagggcag cggtccctat ttctatctgc cgaaaaccca gtcctagcag    660

gaagcggcct ggtggagcga agtcttcagc tatgcagaag atcgctttaa tctgccgcgc    720

ggcaccatca aggcgacgtt gctgattgaa acgctgcccg ccgtgttcca gatggacgaa    780

atccttcacg cgctgcgcga ccatattgtt ggtctgaact gcggtcgctg ggattacatc    840

ttcagctata tcaaaacgtt gaaaaactat cccgatcgtg tcctgccaga cagacaggcc    900

gtgacgatgg ataaaccatt cctgaatgct tactcacgcc tgctgattaa aacctgccat    960

aaacgcggtg cttttgcgat gggcggcatg gccgcgttta ttccgagcaa agatgaagag   1020

cgtaataacc aggtgctcaa caaagtaaaa gcggataaag cgctggaagc caataacggt   1080

cacgatggca catggatcgc tcacccaggc cttgcggaca cggcaatggc ggtattcaac   1140

gacattctcg gctcccgtaa aaatcagctt gaagtattgc gcgaacaaga cgcgccgatt   1200

actgccgatc agctgctggc accttgtgat ggtgaacgca ccgaagaagg tatgcgcgct   1260

aacattcgcg tggctgtgca gtacatcgaa gcgtggatct ccggcaacgg ctgcgtgccg   1320

atttatggcc tgatggaaga tgcggcgacg gctgaaattt cccgtacctc gatctggcag   1380

tggatccatc atcaaaaaac gttgagcaat ggcaaaccgg tgaccaaagc cttgttccgc   1440

cagatgctgg gcgaagagat gaaagtcatt gccagcgaac tgggcgaaga acgtttctcc   1500

cagggccgtt ttgacgatgc cgcacgcttg atggaacaga tcaccacttc cgatgagtta   1560

attgatttcc tgaccctgcc aggctaccgc ctgttagcgt aa                       1602


<210> SEQ ID NO 52
<211> LENGTH: 1602
<212> TYPE: DNA
<213> ORGANISM: Shigella sonnei

<400> SEQUENCE: 52

atgactgaac aggcaacaac aaccgatgaa ctggctttca caaggccgta tggcgagcag     60

gagaagcaaa ttcttactgc cgaagcggta gaatttctga ctgagctggt gacgcatttt    120
```

acgccacaac gcaataaact tctggcagcg cgcattcagc agcagcaaga tattgataac 180
ggaacgttgc ctgattttat ttcggaaaca gcttccattc gcgatgctga ttggaaaatt 240
cgcgggattc ctgcggactt agaagaccgc cgcgtagaga taactggccc ggtagagcgc 300
aagatggtga tcaacgcgct caacgccaat gtgaaagtct ttatggccga tttcgaagat 360
tcactggccc cggactggaa caaagtgatc gacgggcaaa ttaacctgcg tgatgcagtt 420
aacggcacca tcagctatac caatgaagca ggcaaaattt atcagctcaa gcccaatcca 480
gcggttttga tttgtcgggt acgcggtcta cacttgccgg aaaaacatgt cacctggcgt 540
ggtgaggcaa tccccggtag cctgtttgat tttgcgctct atttcttcca caactatcag 600
gcactgttgg caaagggcag cggtccctat ttctatctgc cgaaaaccca gtcctggcag 660
gaagcggcct ggtggagcga agtcttcagc tatgcagaag atcgctttaa tctgccgcgc 720
ggcgccatca aggcgacgtt gctgattgaa acgctgcccg ccgtgttcca gatggacgaa 780
atccttcacg cgctgcgcga ccatattgtt ggtctgaact gcggtcgctg ggattacatc 840
ttcagctata tcaaaacgtt gaaaaactat cccgatcgtg tcctgccaga cagacaggcc 900
gtgacgatgg ataaaccatt cctgaatgct tactcacgcc tgctgattaa aacctgccat 960
aaacgcggtg cttttgcgat gggcggcatg gcagcgttta ttccgagcaa agatgaagag 1020
cgtaataacc aggtgctcaa caaagtaaaa gcggataaag cgctggaagt caataacggt 1080
cacgatggca catggatcgc tcacccaggc cttgcggaca cggcaatggc ggtattcaac 1140
gacattctcg gctcccgtaa aaatcagctt gaagtattgc gcgaacaaga cgcgccgatt 1200
actgccgatc agctgctggc accttgtgac ggtgaacgca ccgaagaagg tatgcgcgcc 1260
aacattcgcg tggctgtgca gtacatcgaa gcgtggatct ccggcaacgg ctgcgtgccg 1320
atttatggcc tgatggaaga tgcggcgacg gctgaaattt cccgtacctc gatctggcag 1380
tggatccatc atcaaaaaac gttgagcaat ggcaaaccgg tgaccaaagc cttgttccgc 1440
tagatgctgg gcgaagagat gaaagtcatt gccagcgaac tgggcgaaga acgtttctcc 1500
cagggccgtt ttgacgatgc cgcacgcttg atggaacaga tcaccacttc cgatgagtta 1560
attgatttcc tgaccctgcc aggctaccgc ctgttagcgt aa 1602

<210> SEQ ID NO 53
<211> LENGTH: 1602
<212> TYPE: DNA
<213> ORGANISM: Escherichia coli CFT073

<400> SEQUENCE: 53
atgactgaac aggcaacaac aatcgatgaa ctggctttta caaggccgta tggcgagcag 60
gagaagcaaa ttcttactgc cgaagcggta gaatttctga ctgagctggt gacgcatttt 120
acgccacaac gcaataaact tctggcagcg cgtattcagc agcagcagga tatcgataac 180
ggaatgttgc ctgattttat ttcggaaaca gcttccattc gttatgctga ctggaaaatt 240
cgcgggattc cttcggactt agaagatcgt cgcgtagaga ttaccggacc tgtagagcgc 300
aagatggtga tcaacgcgct caacgccaat gtgaaagtct ttatggccga tttcgaagat 360
tcactggcac cagactggaa caaagtgatc gatgggcaaa ttaacctgcg cgatgcggtt 420
aacggcacca tcagctatag caatgaagca ggcaaaattt atcagctcaa gcccaatcca 480
gcggttttga tttgtcgggt acgcggtctg cacttgccgg aaaaacatgt cacctggcgt 540
ggtgagacaa tccccggtag cctgtttgat tttgcgctct atttcttcca caactatcag 600
gcactgttgg caaagggcag cggtccctat ttctatctgc cgaaaaccca gtcctggcag 660

```
gaagcggcct ggtggagcga agtcttcagc tatgcagaag atcgctttaa tctgccgcgc    720

ggcaccatca aggcgacgtt gctgattgaa acgctgcccg ccgtgttcca gatggatgaa    780

atccttcacg cgctgcgtga ccatattgtt ggtctgaact gcggtcgttg ggattacatc    840

ttcagttata tcaaaacatt gaaaaactat cccgatcgcg tcctgccaga cagacaggca    900

gtgacgatgg ataaaccctt cctgaatgct tactcacgcc tgttgattaa aacctgccat    960

aaacgcggtg cttttgcgat gggcggcatg gcggcgttta ttccgagcaa agatgaagag   1020

cgcaataacc aggtgctcga caaagtaaaa gcggataaat cgctggaagc caataacggt   1080

cacgatggca catggatcgc tcacccgggc cttgctgata cggcaatggc ggtattcaac   1140

gatattctcg gctcccgcaa aaaccagctt gaggtgatgc gcgaacaaga cgcgccgatt   1200

actgccgatc agctgctggc accttgtgct ggtgaacgca ccgaagaagg tatgcgcgcc   1260

aacattcgcg tggctgtgca gtacatcgaa gcgtggatct ctggcaatgg ctgtgtgccg   1320

atttatggcc tgatggaaga tgcggcgacg gctgaaattt ccagtacctc aatctggcag   1380

tggatccatc atcaaaaaac gttgagcaat ggcaaaccgg tgactaaagc cttgttccgc   1440

cagatgctgg gcgaagagat gaaagtcatt gccagcgaac tgggcgaaga acgtttctcc   1500

catgggcgtt ttgacgatgc cgcacgcttg atggaacaga tcaccacttc cgatgagtta   1560

attgatttcc tgaccctgcc aggctaccgc ctgttagcgt aa                      1602
```

<210> SEQ ID NO 54
<211> LENGTH: 722
<212> TYPE: PRT
<213> ORGANISM: Escherichia coli

<400> SEQUENCE: 54

```
Ser Gln Thr Ile Thr Gln Ser Arg Leu Arg Ile Asp Ala Asn Phe Lys
1               5                   10                  15

Arg Phe Val Asp Glu Glu Val Leu Pro Gly Thr Gly Leu Asp Ala Ala
            20                  25                  30

Ala Phe Trp Arg Asn Phe Asp Glu Ile Val His Asp Leu Ala Pro Glu
        35                  40                  45

Asn Arg Gln Leu Leu Ala Glu Arg Asp Arg Ile Gln Ala Ala Leu Asp
    50                  55                  60

Glu Trp His Arg Ser Asn Pro Gly Pro Val Lys Asp Lys Ala Ala Tyr
65                  70                  75                  80

Lys Ser Phe Leu Arg Glu Leu Gly Tyr Leu Val Pro Gln Pro Glu Arg
                85                  90                  95

Val Thr Val Glu Thr Thr Gly Ile Asp Ser Glu Ile Thr Ser Gln Ala
            100                 105                 110

Gly Pro Gln Leu Val Val Pro Ala Met Asn Ala Arg Tyr Ala Leu Asn
        115                 120                 125

Ala Ala Asn Ala Arg Trp Gly Ser Leu Tyr Asp Ala Leu Tyr Gly Ser
    130                 135                 140

Asp Ile Ile Pro Gln Glu Gly Ala Met Val Ser Gly Tyr Asp Pro Gln
145                 150                 155                 160

Arg Gly Glu Gln Val Ile Ala Trp Val Arg Arg Phe Leu Asp Glu Ser
                165                 170                 175

Leu Pro Leu Glu Asn Gly Ser Tyr Gln Asp Val Val Ala Phe Lys Val
            180                 185                 190

Val Asp Lys Gln Leu Arg Ile Gln Leu Lys Asn Gly Lys Glu Thr Thr
        195                 200                 205
```

-continued

```
Leu Arg Thr Pro Ala Gln Phe Val Gly Tyr Arg Gly Asp Ala Ala Ala
    210                 215                 220

Pro Thr Cys Ile Leu Leu Lys Asn Asn Gly Leu His Ile Glu Leu Gln
225                 230                 235                 240

Ile Asp Ala Asn Gly Arg Ile Gly Lys Asp Asp Pro Ala His Ile Asn
                245                 250                 255

Asp Val Ile Val Glu Ala Ala Ile Ser Thr Ile Leu Asp Cys Glu Asp
            260                 265                 270

Ser Val Ala Ala Val Asp Ala Glu Asp Lys Ile Leu Leu Tyr Arg Asn
        275                 280                 285

Leu Leu Gly Leu Met Gln Gly Thr Leu Gln Glu Lys Met Glu Lys Asn
    290                 295                 300

Gly Arg Gln Ile Val Arg Lys Leu Asn Asp Asp Arg His Tyr Thr Ala
305                 310                 315                 320

Ala Asp Gly Ser Glu Ile Ser Leu His Gly Arg Ser Leu Leu Phe Ile
                325                 330                 335

Arg Asn Val Gly His Leu Met Thr Ile Pro Val Ile Trp Asp Ser Glu
            340                 345                 350

Gly Asn Glu Ile Pro Glu Gly Ile Leu Asp Gly Val Met Thr Gly Ala
        355                 360                 365

Ile Ala Leu Tyr Asp Leu Lys Val Gln Lys Asn Ser Arg Thr Gly Ser
    370                 375                 380

Val Tyr Ile Val Lys Pro Lys Met His Gly Pro Gln Glu Val Ala Phe
385                 390                 395                 400

Ala Asn Lys Leu Phe Thr Arg Ile Glu Thr Met Leu Gly Met Ala Pro
                405                 410                 415

Asn Thr Leu Lys Met Gly Ile Met Asp Glu Glu Arg Arg Thr Ser Leu
            420                 425                 430

Asn Leu Arg Ser Cys Ile Ala Gln Ala Arg Asn Arg Val Ala Phe Ile
        435                 440                 445

Asn Thr Gly Phe Leu Asp Arg Thr Gly Asp Glu Met His Ser Val Met
    450                 455                 460

Glu Ala Gly Pro Met Leu Arg Lys Asn Gln Met Lys Ser Thr Pro Trp
465                 470                 475                 480

Ile Lys Ala Tyr Glu Arg Asn Asn Val Leu Ser Gly Leu Phe Cys Gly
                485                 490                 495

Leu Arg Gly Lys Ala Gln Ile Gly Lys Gly Met Trp Ala Met Pro Asp
            500                 505                 510

Leu Met Ala Asp Met Tyr Ser Gln Lys Gly Asp Gln Leu Arg Ala Gly
        515                 520                 525

Ala Asn Thr Ala Trp Val Pro Ser Pro Thr Ala Ala Thr Leu His Ala
    530                 535                 540

Leu His Tyr His Gln Thr Asn Val Gln Ser Val Gln Ala Asn Ile Ala
545                 550                 555                 560

Gln Thr Glu Phe Asn Ala Glu Phe Glu Pro Leu Leu Asp Asp Leu Leu
                565                 570                 575

Thr Ile Pro Val Ala Glu Asn Ala Asn Trp Ser Ala Gln Glu Ile Gln
            580                 585                 590

Gln Glu Leu Asp Asn Asn Val Gln Gly Ile Leu Gly Tyr Val Val Arg
        595                 600                 605

Trp Val Glu Gln Gly Ile Gly Cys Ser Lys Val Pro Asp Ile His Asn
    610                 615                 620

Val Ala Leu Met Glu Asp Arg Ala Thr Leu Arg Ile Ser Ser Gln His
625                 630                 635                 640
```

Ile Ala Asn Trp Leu Arg His Gly Ile Leu Thr Lys Glu Gln Val Gln
645 650 655

Ala Ser Leu Glu Asn Met Ala Lys Val Val Asp Gln Gln Asn Ala Gly
660 665 670

Asp Pro Ala Tyr Arg Pro Met Ala Gly Asn Phe Ala Asn Ser Cys Ala
675 680 685

Phe Lys Ala Ala Ser Asp Leu Ile Phe Leu Gly Val Lys Gln Pro Asn
690 695 700

Gly Tyr Thr Glu Pro Leu Leu His Ala Trp Arg Leu Arg Glu Lys Glu
705 710 715 720

Ser His

<210> SEQ ID NO 55
<211> LENGTH: 723
<212> TYPE: PRT
<213> ORGANISM: Escherichia coli

<400> SEQUENCE: 55

Met Ser Gln Thr Ile Thr Gln Gly Arg Leu Arg Ile Asn Ala Asn Phe
1 5 10 15

Lys Arg Phe Val Asp Glu Glu Val Leu Pro Gly Thr Gly Leu Asp Thr
20 25 30

Ala Ala Phe Trp Arg Asn Phe Asp Glu Ile Val His Asp Leu Ala Pro
35 40 45

Glu Asn Arg Gln Leu Leu Ala Glu Arg Asp Arg Ile Gln Ala Ala Leu
50 55 60

Asp Glu Trp His Arg Ser Asn Pro Gly Pro Val Lys Asp Lys Ala Ala
65 70 75 80

Tyr Lys Ser Phe Leu Arg Glu Leu Gly Tyr Leu Val Pro Gln Pro Glu
85 90 95

Arg Val Thr Val Glu Thr Thr Gly Ile Asp Ser Glu Ile Thr Ser Gln
100 105 110

Ala Gly Pro Gln Leu Val Val Pro Ala Met Asn Ala Arg Tyr Ala Leu
115 120 125

Asn Ala Ala Asn Ala Arg Trp Gly Ser Leu Tyr Asp Ala Leu Tyr Gly
130 135 140

Ser Asp Ile Ile Pro Gln Glu Gly Ala Met Val Ser Gly Tyr Asp Pro
145 150 155 160

Gln Arg Gly Glu Gln Val Ile Ala Trp Val Arg Arg Phe Leu Asp Glu
165 170 175

Ser Leu Pro Leu Glu Asn Gly Ser Tyr Gln Asp Val Val Ala Phe Lys
180 185 190

Val Val Asp Lys Gln Leu Arg Ile Gln Leu Lys Asn Gly Lys Glu Thr
195 200 205

Thr Leu Arg Thr Pro Ala Gln Phe Val Gly Tyr Arg Gly Asp Ala Ala
210 215 220

Ala Pro Thr Cys Ile Leu Leu Lys Asn Asn Gly Leu His Ile Glu Leu
225 230 235 240

Gln Ile Asp Ala Asn Gly Arg Ile Gly Lys Asp Asp Pro Thr His Ile
245 250 255

Asn Asp Val Ile Val Glu Ala Ala Ile Ser Thr Ile Leu Asp Cys Glu
260 265 270

Asp Ser Val Ala Ala Val Asp Ala Glu Asp Lys Ile Leu Leu Tyr Arg
275 280 285

-continued

```
Asn Leu Leu Gly Leu Met Gln Gly Thr Leu Gln Glu Lys Met Glu Lys
    290                 295                 300

Asn Gly Arg Gln Ile Val Arg Lys Leu Asn Asp Asp Arg His Tyr Thr
305                 310                 315                 320

Ala Ala Asp Gly Ser Glu Ile Ser Leu His Gly Arg Ser Leu Leu Phe
                325                 330                 335

Ile Arg Asn Val Gly His Leu Met Thr Ile Pro Val Ile Trp Asp Ser
            340                 345                 350

Glu Gly Asn Glu Ile Pro Glu Gly Ile Leu Asp Gly Val Met Thr Gly
        355                 360                 365

Ala Ile Ala Leu Tyr Asp Leu Lys Val Gln Lys Asn Ser Arg Thr Gly
    370                 375                 380

Ser Val Tyr Ile Val Lys Pro Lys Met His Gly Pro Gln Glu Val Ala
385                 390                 395                 400

Phe Ala Asn Lys Leu Phe Thr Arg Ile Glu Thr Met Leu Gly Met Ala
                405                 410                 415

Pro Asn Thr Leu Lys Met Gly Ile Met Asp Glu Glu Arg Arg Thr Ser
            420                 425                 430

Leu Asn Leu Arg Ser Cys Ile Ala Gln Ala Arg Asn Arg Val Ala Phe
        435                 440                 445

Ile Asn Thr Gly Phe Leu Asp Arg Thr Gly Asp Glu Met His Ser Val
    450                 455                 460

Met Glu Ala Gly Pro Met Leu Arg Lys Asn Gln Met Lys Ser Thr Pro
465                 470                 475                 480

Trp Ile Lys Ala Tyr Glu Arg Asn Asn Val Leu Ser Gly Leu Phe Cys
                485                 490                 495

Gly Leu Arg Gly Lys Ala Gln Ile Gly Lys Gly Met Trp Ala Met Pro
            500                 505                 510

Asp Leu Met Ala Asp Met Tyr Ser Gln Lys Gly Asp Gln Leu Arg Ala
        515                 520                 525

Gly Ala Asn Thr Ala Trp Val Pro Ser Pro Thr Ala Ala Thr Leu His
    530                 535                 540

Ala Leu His Tyr His Gln Thr Asn Val Gln Ser Val Gln Ala Asn Ile
545                 550                 555                 560

Ala Gln Ser Glu Phe Asn Ala Glu Phe Glu Pro Leu Leu Asp Asp Leu
                565                 570                 575

Leu Thr Ile Pro Val Ala Glu Asn Ala Asn Trp Ser Ala Gln Glu Ile
            580                 585                 590

Gln Gln Glu Leu Asp Asn Asn Val Gln Gly Ile Leu Gly Tyr Val Val
        595                 600                 605

Arg Trp Val Glu Gln Gly Ile Gly Cys Ser Lys Val Pro Asp Ile His
    610                 615                 620

Asn Val Ala Leu Met Glu Asp Arg Ala Thr Leu Arg Ile Ser Ser Gln
625                 630                 635                 640

His Ile Ala Asn Trp Leu Arg His Gly Ile Leu Thr Lys Glu Gln Val
                645                 650                 655

Gln Ala Ser Leu Glu Asn Met Ala Lys Val Val Asp Gln Gln Asn Ala
            660                 665                 670

Gly Asp Pro Ala Tyr Arg Pro Met Ala Gly Asn Phe Ala Asn Ser Cys
        675                 680                 685

Ala Phe Lys Ala Ala Ser Asp Leu Ile Phe Leu Gly Val Lys Gln Pro
    690                 695                 700

Asn Gly Tyr Thr Glu Pro Leu Leu His Ala Trp Arg Leu Arg Glu Lys
705                 710                 715                 720
```

Glu Ser His

<210> SEQ ID NO 56
<211> LENGTH: 722
<212> TYPE: PRT
<213> ORGANISM: Shigella flexneri

<400> SEQUENCE: 56

Ser Gln Thr Ile Thr Gln Gly Arg Leu Arg Ile Asp Ala Asn Phe Lys
1               5                   10                  15

Arg Phe Val Asp Gly Glu Val Leu Pro Gly Val Glu Leu Asp Ala Ala
            20                  25                  30

Ala Phe Trp His Asn Val Asp Glu Ile Val His Asp Leu Ala Pro Glu
        35                  40                  45

Asn Arg Gln Leu Leu Ala Glu Arg Asp Arg Ile Gln Ala Ala Leu Asp
    50                  55                  60

Glu Trp His Arg Ser Asn Pro Gly Pro Val Lys Asp Lys Ala Ala Tyr
65                  70                  75                  80

Lys Ser Phe Leu Arg Glu Leu Gly Tyr Leu Val Pro Gln Pro Glu Arg
                85                  90                  95

Val Thr Val Glu Thr Thr Gly Ile Asp Ser Glu Ile Thr Ser Gln Ala
            100                 105                 110

Gly Pro Gln Leu Val Val Pro Ala Met Asn Ala Arg Tyr Ala Leu Asn
        115                 120                 125

Ala Ala Asn Ala Arg Trp Gly Ser Leu Tyr Asp Ala Leu Tyr Gly Ser
    130                 135                 140

Asp Ile Ile Pro Gln Glu Gly Ala Met Val Ser Gly Tyr Asp Pro Gln
145                 150                 155                 160

Arg Gly Glu Gln Val Ile Ala Trp Val Arg Arg Phe Leu Asp Glu Ser
                165                 170                 175

Leu Pro Leu Glu Asn Gly Ser Tyr Gln Asp Val Val Ala Phe Lys Val
            180                 185                 190

Val Asp Lys Gln Leu Arg Ile Gln Leu Lys Asn Gly Lys Glu Thr Thr
        195                 200                 205

Leu Arg Thr Pro Ala Gln Phe Val Gly Tyr Arg Gly Asp Ala Ala Ala
    210                 215                 220

Pro Thr Cys Ile Leu Leu Lys Asn Asn Gly Leu His Ile Glu Leu Gln
225                 230                 235                 240

Ile Asp Ala Asn Gly Arg Ile Gly Lys Asp Asp Pro Ala His Ile Asn
                245                 250                 255

Asp Val Ile Val Glu Ala Ala Ile Ser Thr Ile Leu Asp Cys Glu Asp
            260                 265                 270

Ser Val Ala Ala Val Asp Ala Glu Asp Lys Ile Leu Leu Tyr Arg Asn
        275                 280                 285

Leu Leu Gly Leu Met Gln Gly Thr Leu Gln Glu Lys Met Glu Lys Asn
    290                 295                 300

Gly Arg Gln Ile Val Arg Lys Leu Asn Asp Asp Arg Gln Tyr Thr Ala
305                 310                 315                 320

Ala Asp Gly Ser Glu Ile Ser Leu His Gly Arg Ser Leu Leu Phe Ile
                325                 330                 335

Arg Asn Val Gly His Leu Met Thr Ile Pro Val Ile Trp Asp Ser Glu
            340                 345                 350

Gly Asn Glu Ile Pro Glu Gly Ile Leu Asp Gly Val Met Thr Gly Ala
        355                 360                 365

Ile Ala Leu Tyr Asp Leu Lys Val Gln Lys Asn Ser Arg Thr Gly Ser
    370                 375                 380

Val Tyr Ile Val Lys Pro Lys Met His Gly Pro Gln Glu Val Ala Phe
385                 390                 395                 400

Ala Asn Lys Leu Phe Thr Arg Ile Glu Thr Met Leu Gly Met Ala Pro
                405                 410                 415

Asn Thr Leu Lys Met Gly Ile Met Asp Glu Glu Arg Arg Thr Ser Leu
            420                 425                 430

Asn Leu Arg Ser Cys Ile Ala Gln Ala Arg Asn Arg Val Ala Phe Ile
        435                 440                 445

Asn Thr Gly Phe Leu Asp Arg Thr Gly Asp Glu Met His Ser Val Met
    450                 455                 460

Glu Ala Gly Pro Met Leu Arg Lys Asn Gln Met Lys Ser Thr Pro Trp
465                 470                 475                 480

Ile Lys Ala Tyr Glu Arg Asn Asn Val Leu Ser Gly Leu Phe Cys Gly
                485                 490                 495

Leu Arg Gly Lys Ala Gln Ile Gly Lys Gly Met Trp Ala Met Pro Asp
            500                 505                 510

Leu Met Ala Asp Met Tyr Ser Gln Lys Gly Asp Gln Leu Arg Ala Gly
        515                 520                 525

Ala Asn Thr Ala Trp Val Pro Ser Pro Thr Ala Ala Thr Leu His Ala
    530                 535                 540

Leu His Tyr His His Thr Asn Val Gln Ser Val Gln Ala Asn Ile Ala
545                 550                 555                 560

Gln Thr Glu Phe Ser Ala Glu Phe Glu Pro Leu Leu Asp Asp Leu Leu
                565                 570                 575

Thr Ile Pro Val Ala Glu Asn Ala Asn Trp Ser Ala Gln Glu Ile Gln
            580                 585                 590

Gln Glu Leu Asp Asn Asn Val Gln Gly Ile Leu Gly Tyr Val Val Arg
        595                 600                 605

Trp Val Glu Gln Gly Ile Gly Cys Ser Lys Val Pro Asp Ile His Asn
    610                 615                 620

Val Ala Leu Met Glu Asp Arg Ala Thr Leu Arg Ile Ser Ser Gln His
625                 630                 635                 640

Ile Ala Asn Trp Leu Arg His Gly Ile Leu Thr Lys Glu Gln Val Gln
                645                 650                 655

Ala Ser Leu Glu Asn Met Ala Lys Val Val Asp Gln Gln Asn Ala Gly
            660                 665                 670

Asp Pro Ala Tyr Arg Pro Met Ala Gly Asn Phe Ala Asn Ser Cys Ala
        675                 680                 685

Phe Lys Ala Ala Ser Asp Leu Ile Phe Leu Gly Val Lys Gln Pro Asn
    690                 695                 700

Gly Tyr Thr Glu Pro Leu Leu His Ala Trp Arg Leu Arg Glu Lys Glu
705                 710                 715                 720

Ser His

<210> SEQ ID NO 57
<211> LENGTH: 722
<212> TYPE: PRT
<213> ORGANISM: Escherichia coli 06

<400> SEQUENCE: 57

Ser Gln Thr Ile Thr Gln Gly Arg Leu Arg Ile Asp Ala Asn Phe Lys
1               5                   10                  15

Arg Phe Val Asp Glu Glu Val Leu Pro Gly Val Glu Leu Asp Ala Ala

-continued

```
            20                  25                  30

Ala Phe Trp His Asn Val Asp Glu Ile Val His Asp Leu Ala Pro Glu
        35                  40                  45

Asn Arg Gln Leu Leu Ala Glu Arg Asp Arg Ile Gln Ala Ala Leu Asp
    50                  55                  60

Glu Trp His Arg Ser Asn Pro Gly Pro Val Lys Asp Lys Ala Ala Tyr
65                  70                  75                  80

Lys Ser Phe Leu Arg Glu Leu Gly Tyr Leu Val Pro Gln Pro Asp His
                85                  90                  95

Val Thr Val Glu Thr Thr Gly Ile Asp Ser Glu Ile Thr Ser Gln Ala
            100                 105                 110

Gly Pro Gln Leu Val Val Pro Ala Met Asn Ala Arg Tyr Ala Leu Asn
        115                 120                 125

Ala Ala Asn Ala Arg Trp Gly Ser Leu Tyr Asp Ala Leu Tyr Gly Ser
    130                 135                 140

Asp Ile Ile Pro Gln Glu Gly Ala Met Val Ser Gly Tyr Asp Pro Gln
145                 150                 155                 160

Arg Gly Glu Gln Val Ile Ala Trp Val Arg Arg Phe Leu Asp Glu Ser
                165                 170                 175

Leu Pro Leu Glu Asn Gly Ser Tyr Gln Asp Val Val Ala Phe Lys Val
            180                 185                 190

Val Asp Lys Gln Leu Arg Ile Gln Leu Lys Asn Gly Lys Glu Thr Thr
        195                 200                 205

Leu Arg Thr Pro Ala Gln Phe Val Gly Tyr Arg Gly Asp Thr Ala Ala
    210                 215                 220

Pro Thr Cys Ile Leu Leu Lys Asn Asn Gly Leu His Ile Glu Leu Gln
225                 230                 235                 240

Ile Asp Ala Asn Gly Arg Ile Gly Lys Asp Asp Ser Ala His Ile Asn
                245                 250                 255

Asp Val Ile Val Glu Ala Ala Ile Ser Thr Ile Leu Asp Cys Glu Asp
            260                 265                 270

Ser Val Ala Ala Val Asp Ala Glu Asp Lys Ile Leu Leu Tyr Arg Asn
        275                 280                 285

Leu Leu Gly Leu Met Gln Gly Thr Leu Gln Glu Lys Met Glu Lys Asn
    290                 295                 300

Gly Arg Gln Ile Val Arg Lys Leu Asn Asp Asp Arg Gln Tyr Thr Ala
305                 310                 315                 320

Ala Asp Gly Ser Glu Ile Ser Leu His Gly Arg Ser Leu Leu Phe Ile
                325                 330                 335

Arg Asn Val Gly His Leu Met Thr Ile Pro Val Ile Trp Asp Ser Glu
            340                 345                 350

Gly Asn Glu Ile Pro Glu Gly Ile Leu Asp Gly Val Met Thr Gly Ala
        355                 360                 365

Ile Ala Leu Tyr Asp Leu Lys Val Gln Lys Asn Ser Arg Thr Gly Ser
    370                 375                 380

Val Tyr Ile Val Lys Pro Lys Met His Gly Pro Gln Glu Val Ala Phe
385                 390                 395                 400

Ala Asn Lys Leu Phe Ser Arg Val Glu Thr Met Leu Gly Met Ala Pro
                405                 410                 415

Asn Thr Leu Lys Met Gly Ile Met Asp Glu Glu Arg Arg Thr Ser Leu
            420                 425                 430

Asn Leu Arg Ser Cys Ile Ala Gln Ala Arg Asn Arg Val Ala Phe Ile
        435                 440                 445
```

```
Asn Thr Gly Phe Leu Asp Arg Thr Gly Asp Glu Met His Ser Val Met
    450                 455                 460

Glu Ala Gly Pro Met Leu Arg Lys Asn Gln Met Lys Ser Thr Pro Trp
465                 470                 475                 480

Ile Lys Ala Tyr Glu Arg Asn Asn Val Leu Ser Gly Leu Phe Cys Gly
                485                 490                 495

Leu Arg Gly Lys Ala Gln Ile Gly Lys Gly Met Trp Ala Met Pro Asp
            500                 505                 510

Leu Met Ala Asp Met Tyr Ser Gln Lys Gly Asp Gln Leu Arg Ala Gly
        515                 520                 525

Ala Asn Thr Ala Trp Val Pro Ser Pro Thr Ala Ala Thr Leu His Ala
    530                 535                 540

Leu His Tyr His Gln Thr Asn Val Gln Ser Val Gln Ala Asn Ile Ala
545                 550                 555                 560

Gln Thr Glu Phe Asn Ala Glu Phe Glu Pro Leu Leu Asp Asp Leu Leu
                565                 570                 575

Thr Ile Pro Val Ala Glu Asn Ala Asn Trp Ser Val Glu Glu Ile Gln
            580                 585                 590

Gln Glu Leu Asp Asn Asn Val Gln Gly Ile Leu Gly Tyr Val Val Arg
        595                 600                 605

Trp Val Glu Gln Gly Ile Gly Cys Ser Lys Val Pro Asp Ile His Asn
    610                 615                 620

Val Ala Leu Met Glu Asp Arg Ala Thr Leu Arg Ile Ser Ser Gln His
625                 630                 635                 640

Ile Ala Asn Trp Leu Arg His Gly Ile Leu Thr Lys Glu Gln Val Gln
                645                 650                 655

Ala Ser Leu Glu Asn Met Ala Lys Val Val Asp Gln Gln Asn Ala Gly
            660                 665                 670

Asp Pro Ala Tyr Arg Pro Met Ala Gly Asn Phe Ala Asn Ser Cys Ala
        675                 680                 685

Phe Lys Ala Ala Ser Asp Leu Ile Phe Leu Gly Val Lys Gln Pro Asn
    690                 695                 700

Gly Tyr Thr Glu Pro Leu Leu His Ala Trp Arg Leu Arg Glu Lys Glu
705                 710                 715                 720

Ser His


<210> SEQ ID NO 58
<211> LENGTH: 2172
<212> TYPE: DNA
<213> ORGANISM: Escherichia coli pathogenicity island V, strain 536

<400> SEQUENCE: 58

atgagtcaaa ccataaccca gggccgttta cgcattaacg ccaattttaa acgttttgtg     60

gatgaagaag ttttaccggg aacagggttg gacactgcgg cgttctggcg caattttgat    120

gagatcgttc acgatctggc accagaaaat cgtcagttgc tggcagaacg cgatcgcatt    180

caggcggcgc ttgatgagtg gcatcgcagc aatccggggc cggttaaaga taaagcggcc    240

tataaatctt tcctgcgtga actgggctac ctggtgccac aaccggagcg cgtgacggtg    300

gaaaccacgg gcattgacag cgaaatcacc agccaggcgg ggccacagct ggtggttccg    360

gcaatgaacg cccgctacgc gctgaacgcg gcgaacgctc gctggggctc actgtacgat    420

gcgttatacg gcagcgacat catcccgcag gaaggggcga tggtcagcgg ctacgatccg    480

caacgcggtg agcaggttat cgcctgggtt cggcgtttcc tcgatgaatc actaccgctg    540

gaaaacggca gctatcagga tgtggtggcg tttaaggtgg tcgataaaca attacgcatc    600
```

-continued

```
cagttgaaaa atggtaaaga aaccacgtta cgtaccccgg cgcagtttgt cggttaccgt    660
ggcgatgccg ctgcgccgac ctgcattttg ctgaaaaata acggtctgca tattgaactg    720
caaattgatg ccaacgggcg gattggcaaa gacgatccga cgcatatcaa cgatgttatc    780
gtcgaagcgg ccatcagtac cattctcgac tgcgaagatt cggtcgcggc ggttgatgcg    840
gaagataaaa tcctgctgta tcgcaacctg ctgggcctga tgcaggggac tctgcaagag    900
aaaatggaaa aaaacggtcg gcaaatcgtg cgtaaactga atgacgatcg tcattacacc    960
gccgccgatg gctctgaaat ttctctgcac ggacgctcgc tgctgtttat ccgcaacgtg   1020
ggtcatttga tgaccattcc tgtgatttgg gacagcgaag gcaatgaaat cccggaaggc   1080
attcttgatg gcgtcatgac tggcgcgatt gccctctatg atttaaaagt gcagaaaaac   1140
tcgcgcactg gcagcgtcta tattgtgaaa ccgaaaatgc acggtccgca ggaagtggcg   1200
ttcgccaaca aactgtttac ccgcattgag acaatgctcg gtatggcacc gaataccctg   1260
aaaatgggca ttatggatga agaacgtcgg acctcgctga acttgcgtag ctgtatcgct   1320
caggcgcgca accgcgtggc gttcatcaat accggtttcc tcgaccgtac cggcgatgaa   1380
atgcattcgg tgatggaagc tggcccgatg ctgcgtaaaa atcagatgaa atcgacgcct   1440
tggatcaaag cctacgagcg taataacgtg ctttccggtc tgttctgtgg gctgcgcggt   1500
aaagcgcaaa ttggtaaagg catgtgggca atgccggacc tgatggcaga catgtacagc   1560
cagaagggcg accaactgcg tgccggggcg aacacggcct gggttccgtc accaaccgct   1620
gctacgctcc atgcgctgca ctaccatcaa accaacgtac agagcgtgca agccaacatt   1680
gcccagagcg agttcaatgc tgaatttgaa ccgctgctgg acgatctgct gactattccg   1740
gtggctgaaa acgctaactg gtcggcacaa gagatccaac aagagctgga taacaacgta   1800
caggggattc tgggttacgt ggtgcgctgg gtggagcagg ggattggttg ttcaaaagtg   1860
ccggatattc acaatgtggc gctgatggaa gaccgtgcaa cgttgcgtat ctccagccag   1920
catatcgcca actggttacg ccacggtatt ctgaccaaag aacaggtgca ggcgtcgctg   1980
gagaatatgg cgaaagtggt tgatcagcaa aacgctggcg atccggctta tcgtccgatg   2040
gcggggaatt tcgctaactc gtgtgctttt aaagctgcca gcgatttaat cttcctcggc   2100
gtgaaacagc caaacggcta tactgaaccg ttattacacg cctggcgttt acgcgaaaaa   2160
gaaagtcatt aa                                                       2172
```

<210> SEQ ID NO 59
<211> LENGTH: 2172
<212> TYPE: DNA
<213> ORGANISM: *Shigella flexneri*

<400> SEQUENCE: 59

```
atgagtcaaa ccataaccca gggccgttta cgcattgacg ccaattttaa acgttttgtg     60
gatggagaag ttttgccggg cgtggaactg gacgctgctg cattctggca caatgttgat    120
gagatcgttc acgatctggc accagaaaat cgtcagttgc tggcagaacg cgatcgcatt    180
caggcggcgc ttgatgagtg gcatcgcagc aatccggggc cggtaaaaga taaagcggcc    240
tataaatctt tccttcgtga actgggctac ctggtgccgc aaccggagcg cgtgacggtg    300
gaaaccacgg gcattgacag cgaaatcacc agtcaggcgg ggccacagct ggtggttccg    360
gcaatgaacg cccgctacgc gctgaacgcg gcgaacgctc gctggggctc actgtacgat    420
gcgttatacg gcagcgacat catcccgcag gaaggggcga tggtcagtgg ctacgatccg    480
cagcgcggtg agcaggttat cgcctgggtt cgacgtttcc tcgatgaatc actaccgctg    540
```

gaaaacggca gctatcagga tgtggtggcg tttaaggtgg tcgataaaca attacgcatc 600
cagttgaaaa atggtaaaga aaccacgtta cgtactccag cacagtttgt cggttaccgt 660
ggcgatgccg ctgcgccgac ctgcattttg ctgaaaaata acggcctgca tattgaactg 720
caaattgatg ccaacgggcg gattggcaaa gacgatccgg cgcacatcaa cgatgttatc 780
gtcgaagctg ctatcagtac cattctcgac tgcgaagatt cggtcgcggc ggttgatgcg 840
gaagataaaa tcctgctgta ccgcaatctg ctgggcctga tgcaggggac tctgcaagag 900
aaaatggaga aaaacggtcg gcaaatcgta cgtaaactga atgacgatcg tcagtacacc 960
gccgccgatg gctctgaaat ttctctgcac ggacgctcgt tgctgtttat ccgcaacgtg 1020
ggtcatttga tgaccattcc tgtgatttgg gacagcgaag gcaatgaaat cccggaaggt 1080
attcttgatg gcgtcatgac tggcgcgatt gccctctatg atttaaaagt gcagaaaaac 1140
tcgcgcactg gcagcgtcta tattgtgaaa ccgaaaatgc acggtccgca ggaagtggcg 1200
ttcgccaaca aactgtttac ccgcattgag acaatgctcg gtatggcacc gaataccctg 1260
aaaatgggca ttatggatga agaacgccgg acctcgctga acttgcgtag ctgtatcgct 1320
caggcgcgca accgcgtggc gttcatcaat accggtttcc tcgaccgtac cggcgatgaa 1380
atgcattcgg tgatggaagc tggcccgatg ctgcgtaaaa accagatgaa atcgacgccg 1440
tggatcaaag cctacgaacg taataacgtg ctttccggtc tgttctgtgg gctgcgcggt 1500
aaagcgcaaa tcggtaaagg catgtgggca atgccggacc tgatggcaga catgtacagc 1560
cagaagggcg accaactgcg tgccggggca aacacagcct gggttccgtc accaaccgct 1620
gctacgctcc atgcgctgca ctaccaccat accaacgtac agagcgtgca agccaacatt 1680
gcccagaccg agttcagtgc tgaatttgaa ccgctgctgg acgatctgct gactattccg 1740
gtggctgaaa acgctaactg gtcggcgcaa gagatccaac aagagctgga taacaacgtg 1800
caggggattc tggggtacgt ggtgcgttgg gtggagcagg ggattggttg ttcaaaagtg 1860
ccggatattc acaacgtggc gctgatggaa gaccgcgcaa cgctgcgtat ctccagccag 1920
catatcgcca actggttacg tcacggtatt ctgaccaaag aacaggtgca ggcgtcgctg 1980
gagaatatgg cgaaagtggt tgatcagcaa aatgctggcg atccggctta tcgtccgatg 2040
gcggggaatt tcgctaactc gtgtgctttt aaagctgcca gcgatttaat cttcctcggc 2100
gtgaaacagc caaacggtta taccgaaccg ttattacacg cctggcgttt acgcgaaaaa 2160
gaaagtcatt aa 2172

<210> SEQ ID NO 60
<211> LENGTH: 2172
<212> TYPE: DNA
<213> ORGANISM: Escherichia coli CFT073

<400> SEQUENCE: 60
atgagtcaaa ccataaccca gggccgttta cgcattgacg ccaattttaa acgttttgtg 60
gatgaagaag ttttacctgg cgtggaactg gatgctgccg cgttttggca caatgttgat 120
gagatcgttc acgatctggc gccagagaat cgtcagttgc tggcagagcg cgatcgcatt 180
caggcggcgc ttgatgagtg gcatcgcagc aatccggggc cggtaaaaga taaagcggcc 240
tataaatctt tcctgcgtga actgggctac ctggtgccac agcctgacca cgttacggtg 300
gaaaccacgg gcatcgacag cgaaatcacc agtcaggcgg ggccacagct ggtggttccg 360
gcgatgaacg cccgctacgc gttgaacgcg gcgaacgctc gctggggctc actgtacgat 420
gcgttatacg gcagcgacat catcccgcag gaaggggcga tggtcagcgg ctacgatccg 480

-continued

```
cagcgtggtg agcaggttat cgcctgggtt cggcgtttcc tcgatgaatc actaccgctg    540
gaaaatggca gctatcagga tgtggtggcg tttaaggtgg tcgataaaca attacgcatc    600
cagttgaaaa atggtaaaga aaccacgtta cgtactccag cacagtttgt cggttaccgt    660
ggcgatactg ctgcgccgac ctgcattttg ctgaaaaata acggcctgca tattgagcta    720
caaatcgatg ccaacgggcg gattggcaaa gacgattcgg cgcacatcaa cgatgttatc    780
gtcgaagcgg ccatcagtac cattctcgac tgcgaagatt cggttgcggc ggttgatgcg    840
gaagataaaa tcctgctgta ccgcaacctg ctgggcctga tgcaggggac tctgcaagag    900
aaaatggaga agaacggtcg gcaaatcgtg cgtaaactga atgacgatcg tcagtacact    960
gccgccgatg gatctgaaat ttctctgcac ggacgctcgt tgctgtttat ccgcaacgtg   1020
ggtcatttga tgaccattcc tgtgatttgg gacagcgaag gcaatgaaat cccggaaggc   1080
attcttgatg gcgtcatgac tggcgcgatt gccctctatg atttaaaagt gcagaaaaac   1140
tcgcgcactg gcagcgtcta tattgtgaaa ccgaaaatgc acggtccgca ggaagtggcg   1200
ttcgccaaca aactgttttc ccgcgttgag acaatgctcg gtatggcacc gaataccctg   1260
aaaatgggca ttatggatga agaacgccgg acctcgctga acttgcgtag ctgtatcgct   1320
caggcgcgca accgcgtggc gttcatcaat accggtttcc tcgaccgtac cggcgatgaa   1380
atgcattcgg tgatggaagc gggcccgatg ctgcgtaaaa accagatgaa atcgacgccg   1440
tggatcaaag cctacgaacg taataacgtg ctttccggtc tgttctgtgg gctacgtgga   1500
aaagcgcaaa tcggtaaagg catgtgggca atgccggacc tgatggcaga catgtacagc   1560
cagaagggcg accaattgcg tgccggggca aacacggcct gggttccgtc gccaactgcc   1620
gctacgctcc atgcgctgca ctaccaccaa accaacgtac agagcgtgca agccaacatt   1680
gcccagaccg agttcaatgc tgaatttgaa ccgctgctgg acgatctgct gactattccg   1740
gttgctgaaa acgctaactg gtcggtggaa gagatccaac aagagctgga taacaacgtg   1800
caggggattc tggggtacgt ggtgcgttgg gtggagcagg ggattggttg ttcaaaagtg   1860
ccggatattc ataacgtggc gctgatggaa gaccgcgcaa cgctgcgtat ctccagccag   1920
catatcgcca actggttacg tcacggtatt ctgaccaaag aacaggtgca ggcgtcgctg   1980
gagaatatgg cgaaagtggt tgatcagcaa aacgctggcg atccggctta tcgtccgatg   2040
gcgggggaatt tcgctaactc gtgtgctttt aaagctgcca gcgatttaat cttcctcggc   2100
gtgaaacagc caaacggcta taccgaaccg ttattacacg cctggcgttt acgcgaaaaa   2160
gaaagtcatt aa                                                       2172
```

ALTERED GLYOXYLATE SHUNT FOR IMPROVED PRODUCTION OF ASPARTATE-DERIVED AMINO ACIDS AND CHEMICALS

CLAIM TO PRIORITY

This application claims priority to U.S. Provisional Patent Application No. 60/692,341, having a filing date of Jun. 20, 2005. That application is incorporated by reference as if fully rewritten herein.

BACKGROUND

The following includes information that may be useful in understanding the present inventions. It is not an admission that any of the information provided herein is prior art, or material, to the presently described or claimed inventions, or that any publication or document that is specifically or implicitly referenced is prior art.

The present invention relates to, but is not limited to, the fields of microbiology and microbial genetics. The invention relates, for example, to novel bacterial strains, novel nucleotide sequences, novel amino acid sequences, and processes for employing these bacterial strains, novel nucleotide sequences, and/or novel amino acid sequences for fermentative production of amino acids including, but not limited to, L-threonine, L-lysine, L-homoserine, and L-isoleucine. Preferably, L-threonine is produced. The invention also relates to the production of animal feed additives. The invention also relates to fermentation and synthesis of fine chemicals including but not limited to those amino acids listed above.

In *Escherichia coli*, the amino acids L-threonine, L-isoleucine, L-homoserine, L-lysine and L-methionine derive all or part of their carbon atoms from aspartate (aspartic acid) via a common biosynthetic pathway (G. N. Cohen, "The Common Pathway to Lysine, Methionine and Threonine," pp. 147-171 in Amino Acids: Biosynthesis and Genetic Regulation, K. M. Herrmann and R. L. Somerville, eds., Addison-Wesley Publishing Co., Inc., Reading, Mass. (1983)):

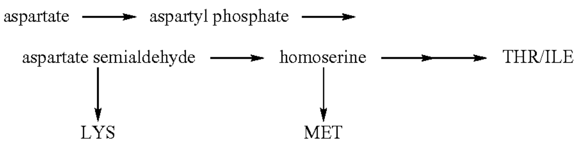

Aspartate is, in turn, derived from oxaloacetate (OAA). As reported in U.S. Pat. No. 6,455,284, to Gokarn, et al., aerobic fermentation can be used to produce oxaloacetate-derived amino acids. Unfortunately, process yields may be limited by stringent metabolic regulation of carbon flow. In general, carbon flux toward OAA is said to remain constant regardless of perturbations to the metabolic system. J. Vallino, et al., *Biotechnol. Bioeng.,* 41: 633, 646 (1993). Overcoming this metabolic regulation would be advantageous in increasing production of OAA-derived amino acids and other products.

In aerobic bacterial metabolism, carbon atoms of glucose may be fully oxidized to carbon dioxide in the tricarboxylic acid cycle (TCA), also known as the citric acid or Krebs cycle. The TCA cycle begins when OAA combines with acetyl-CoA to form citrate. An example of the aerobic metabolism pathway in the bacterium *Escherichia coli* is shown in FIG. 1. In addition to its role as a primary molecule in the TCA cycle, OAA may be used as a precursor for synthesis of amino acids, including L-asparagine, L-aspartate, L-methionine, L-threonine, L-isoleucine, L-homoserine, and L-lysine.

Given the importance of OAA to the TCA cycle, OAA that is used for biosynthesis of amino acids should be replaced to allow further progress of the TCA cycle. Many organisms have therefore developed "anaplerotic pathways" that regenerate intermediates for use in the TCA cycle. In some organisms, for instance in some plants and microorganisms, TCA cycle intermediates may be formed from acetyl-CoA via an anaplerotic pathway known as the "glyoxylate shunt," also known as the "glyoxylate bypass" or "glyoxylate cycle." The glyoxylate shunt in *E. coli* is shown in FIG. 2.

The glyoxylate shunt allows organisms growing on certain substrates (for instance, acetate, fatty acids, or some long-chain alkanes) to replenish their OAA. Such a mechanism is useful because such substrates do not provide 3-carbon intermediates that can be carboxylated to form OAA needed in the TCA cycle. The branch point of carbon flux between the TCA cycle and the glyoxylate shunt is said to be isocitrate (K. Walsh et al., *J. Biol. Chem.* 259:15, 9646-9654 (1984)).

In the glyoxylate shunt, isocitrate from the TCA cycle is cleaved into glyoxylate and succinate by the enzyme isocitrate lyase. The enzyme malate synthase is then used to combine glyoxylate with acetyl-CoA to form malate. Both succinate and malate may be used to generate OAA through the TCA cycle. In general, expression of genes encoding the glyoxylate bypass enzymes is said to be rigidly controlled, such that these genes may be repressed when certain 3-carbon compounds are available for use in the TCA cycle.

The following reactions may be observed:

aceA, isocitrate lyase: isocitrate <--> glyoxylate+succinate aceB, malate synthase A: acetyl-CoA+H2O+glycoxylate <--> malate+CoA glcB, malate synthase G: acetyl-CoA+H2O+glycoxylate <--> malate+CoA In *E. coli*, genes encoding glyoxylate shunt enzymes are located in the aceBAK operon. They are said to be controlled by a number of transcriptional regulators including, for instance, IclR (A. Sunnarborg et al., *J. Bact.,* 172: 2642-2649 (1990)), FadR (S. Maloy et al., *J. Bact.* 148: 83-90 (1981)), FruR (A. Chia et al., *J. Bact.,* 171: 2424-2434 (1989)), and ArcAB (S. Iuchi et al., *J. Bact.,* 171: 868-873 (1989)).

The aceBAK operon has been reported to be expressed from a $\sigma^{70}$-type promoter that is upstream of aceB (E. Resnik et al., *J. Bact.* 178:9, 2715-2717 (1996)). A nucleotide sequence for the aceBAK operon of the *E. coli* strain K-12 is set forth in SEQ ID NO:1. Keseler, I. M., et al., *Nuc. Acids Res.,* 33: D334-357 (2005). The operon is said to be regulated by a repressor protein expressed from iclR and activated by growth on acetate or fatty acids (E. Resnik et al., supra.). The aceA gene (SEQ ID NO:2) (Keseler, I. M., et al., supra) is reported to encode isocitrate lyase (SEQ ID NO:3) (Keseler, I. M., et al., supra), and the aceB gene (SEQ ID NO:4) (Keseler, I. M., et al., supra) is reported to produce malate synthase A (SEQ ID NO:5) (Keseler, I. M., et al., supra). The final gene in the glcDFGB operon (SEQ ID NO:6) (Keseler, I. M., et al., supra), glcB (SEQ ID NO:7) (Keseler, I. M., et al., supra), is reported to encode malate synthase G (SEQ ID NO:8) (Keseler, I. M., et al., supra), which may replace malate synthase A in the glyoxylate shunt when malate synthase A is absent. (L. N. Omston, et al., *J. Bact.,* 98:2, 1098-1108 (1969); W. Farmer, et al., *App. & Env. Microbiol.,* 63:8, 3205-3210 (1997); M. Oh, et al., *J. Biol. Chem.,* 277:15, 13175-13183 (2002).)

Many features of wild-type strains of *E. coli* have been reported. For instance, the genome of *E. coli* strain K-12 is reported in F. R. Blattner, et al., *Science,* 1997 Sep. 5; 277 (5331): 1453-74. Some authors have reported attempts to divert carbon flow toward OAA, since it was postulated that increasing flow of carbon toward OAA would increase production of biochemicals that may be synthesized with OAA as a precursor. Efforts have included either knockout of genes that act as aceBAK repressors or enhancement of genes that inhibit aceBAK (to avoid carbon flow into the glyoxylate shunt). For instance, U.S. Pat. No. 6,630,332, to Rieping et al., reports increased threonine production in Enterobacteriaceae through over-expression of the mqo gene, which produces the enzyme malate:quinone oxidoreductase.

European Patent Application No. EP 1 408 123 A1, to Park, et al., reports production of L-threonine using a microorganism in which the fadR gene has been knocked-out. U.S. Patent Application Publication No. 2003/0059903A1, to Rieping, et al., and International Publication WO 02/081722, to Rieping, et al., report a process for the production of L-threonine including fermentation of Enterobacteriaceae in which the aceA gene or nucleotide sequences encoding for the aceA gene are attenuated or switched off.

International Patent Publication No. WO 03/038106A2, to Rieping, et al., reports a process for production of L-threonine using bacteria modified to enhance activity levels of the fadR gene product and/or the iclR gene product, both of which are transcriptional repressors of the aceBAK operon. International Patent Publication No. WO 03/008616, to Hermann, reports a process for the preparation of L-threonine including fermentation of bacteria of the Enterobacteriaceae family that have been modified so that the expression of the aceK gene product is attenuated.

Methods and techniques for the growth of bacterial cells, the introduction of isolated DNA molecules into host cells, and the isolation, cloning and sequencing of isolated nucleic acid molecules, etc., may generally be known to those of skill in the art. These methods and techniques are described in many standard laboratory manuals, such as Davis, et al., Basic Methods In Molecular Biology (1986),. Miller, J. H., *Experiments in Molecular Genetics*, Cold Spring Harbor Laboratory Press, Cold Spring Harbor, N.Y. (1972); Miller, J. H., *A Short Course in Bacterial Genetics*, Cold Spring Harbor Laboratory Press, Cold Spring Harbor, N.Y. (1992); Singer M. and Berg, P., *Genes & Genomes*, University Science Books, Mill Valley, Calif. (1991); Sambrook, J., et al., *Molecular Cloning: A Laboratory Manual,* 2d ed., Cold Spring Harbor Laboratory Press, Cold Spring Harbor, N.Y. (1989); Kaufman, P. B. et al., *Handbook of Molecular and Cellular Methods in Biology and Medicine*, CRC Press, Boca Raton, Fla. (1995); Methods in Plant Molecular Biology and Biotechnology, Glick, B. R. and Thompson, J. E. eds., CRC Press, Boca Raton, Fla. (1993); Smith-Keary, P. F. *Molecular Genetics of Escherichia coli*, The Guilford Press, New York, N.Y. (1989); Schleif, R. F. and Wensink, P. C. *Practical Methods in Molecular Biology*, Springer-Verlag (1981); Singer, M. and Berg, P. *Genes & Genomes*, University Science Books, Mill Valley, Calif. (1991); Kaufman, P. B. et al., *Handbook of Molecular and Cellular Methods in Biology and Medicine*, CRC Press, Boca Raton, Fla. (1995); *Plasmids: A Practical Approach,* 2nd Edition, Hardy, K. D., ed., Oxford University Press, New York, N.Y. (1993); *Vectors: Essential Data*, Gacesa, P., and Ramji, D. P., eds., John Wiley & Sons Pub., New York, N.Y. (1994); *PCR primer: A Laboratory Manual*, Dieffenbach, C. W. and Dveksler, G. S. eds. Cold Spring Harbor Laboratory Press, New York, N.Y. (1995); *PCR Protocols: A Guide to Methods and Applications*, Innis, M. A. et al., eds. Academic Press, San Diego, Calif. (1990); *Guide to Electroporation and Electrofusions*, Chang, D., et al., eds., Academic Press, San Diego, Calif. (1992); *Promiscuous Plasmids of Gram-Negative Bacteria*, Thomas, C. M., ed., Academic Press, London (1989); *The Biology of plasmids*, Summers, D. K., Blackwell Science, Cambridge, Mass. (1996); *Understanding DNA and Gene Cloning: A Guide for the Curious*, Drlica, K., ed., John Wiley and Sons Pub., New York, N.Y. (1997); *Vectors: A Survey of Molecular Cloning Vectors and Their Uses*, Rodriguez, R. L., et al., eds., Butterworth, Boston, Mass. (1988); *Bacterial Conjugation*, Clewell, D. B., ed., Plenum Press, New York, N.Y. (1993); Del Solar, G., et al., Replication and control of circular bacterial plasmids, *Microbiol. Mol. Biol. Rev.* 62:434-464 (1998); Meijer, W. J., et al., Rolling-circle plasmids from *Bacillus subtilis*: complete nucleotide sequences and analyses of genes of pTA1015, pTA1040, pTA1050 and pTA1060, and comparisons with related plasmids from gram-positive bacteria, *FEMS Microbiol. Rev.* 21:337-368 (1998); Khan, S. A., Rolling-circle replication of bacterial plasmids, *Microbiol. Mol. Biol. Rev.* 61:442-455 (1997); Baker, R. L., Protein expression using ubiquitin fusion and cleavage, *Curr. Opin. Biotechnol.* 7:541-546 (1996); Makrides, S. C., Strategies for achieving high-level expression of genes in *Escherichia coli, Microbiol. Rev.* 60:512-538 (1996); Nicholl, D. S. T., *Introduction to Genetic Engineering* (2d ed.) 2002; Alonso, J. C., et al., Site-specific recombination in gram-positive theta-replicating plasmids, *FEMS Microbiol. Lett.* 142:1-10 (1996); Miroux, B., et al., Over-production of protein in *Escherichia coli*: mutant hosts that allow synthesis of some membrane protein and globular protein at high levels, *J. Mol. Biol.* 260:289-298 (1996); Kurland, C. G., and Dong, H., Bacterial growth inhibited by over-production of protein, *Mol. Microbiol.* 21:1-4 (1996); Saki, H., and Komano, T., DNA replication of IncQ broad-host-range plasmids in gram-negative bacteria, *Biosci. Biotechnol. Biochem.* 60:377-382 (1996); Deb, J. K., and Nath, N., Plasmids of *Corynebacteria, FEMS Microbiol. Lett.* 175:11-20 (1999); Smith, G. P., Filamentous phages as cloning vectors, *Biotechnol.* 10:61-83 (1988); Espinosa, M., et al., Plasmid rolling circle replication and its control, *FEMS Microbiol. Lett.* 130:111-120 (1995); Lanka, E., and Wilkins, B. M., DNA processing reaction in bacterial conjugation, *Ann. Rev. Biochem.* 64:141-169 (1995); Dreiseikelmann, B., Translocation of DNA across bacterial membranes, *Microbiol. Rev.* 58:293-316 (1994); Nordstrom, K., and Wagner, E. G., Kinetic aspects of control of plasmid replication by antisense RNA, *Trends Biochem. Sci.* 19:294-300 (1994); Frost, L. S., et al., Analysis of the sequence gene products of the transfer region of the F sex factor, *Microbiol. Rev.* 58:162-210 (1994); Drury, L., Transformation of bacteria by electroporation, *Methods Mol. Biol.* 58:249-256 (1996); Dower, W. J., Electroporation of bacteria: a general approach to genetic transformation, *Genet. Eng.* 12:275-295 (1990); Na, S., et al., The factors affecting transformation efficiency of coryneform bacteria by electroporation, *Chin. J. Biotechnol.* 11:193-198 (1995); Pansegrau, W., Covalent association of the traI gene product of plasmid RP4 with the 5'-terminal nucleotide at the relaxation nick site, *J. Biol. Chem.* 265:10637-10644 (1990); Bailey, J. E., Host-vector interactions in *Escherichia coli, Adv. Biochem. Eng. Biotechnol.* 48:29-52 (1993); Funkhouser, J. D. and Smith, W. D., Monovalent Cation Effects on Lysine-sensitive Aspartokinase Catalytic Activity and Allosteric Regulation. *J. Biol. Chem.* 249:7580-7583 (1974); Chassagnole, C., et al., Control of threonine-synthesis pathway in *Escherichia coli*: a theoretical and experimental approach. *Biochem. J.* 356:433-444 (2001); Rais, B., et al., *Biochem. J.* 356:425-432 (2001);

*Escherichia coli* and *Salmonella* cellular and molecular biology, Neidhardt, et al, eds., American Society of Microbiology Press, Washington, D.C. (1996); de Boer, H. A., et al., The tac promoter: a functional hybrid derived from the trp and lac promoters. *Proc. Natl. Acad. Sci.* 80:21-25(1983); Hawley, D. K. and McClure, W. R., Compilation and analysis of *Escherichia coli* promoter DNA sequences. *Nucleic Acids Res.* 11:2237-2255 (1983); Khlebnikov A. and Keasling, J. D., Effect of lacY expression on homogeneity of induction from the Ptac and Ptrc promoters by natural and synthetic inducers. *Biotechnol. Prog.* 18:672-674 (2002); Mulligan, M. E., et al., Characterization in vitro of the effect of spacer length on the activity of *Escherichia coli* RNA polymerase at the tac promoter. *J. Biol. Chem.* 260:3529-3538 (1985); Chung, T., et al., Glyoxylate Bypass Operon of *Escherichia coli* Cloning and Determination of the Functional Map. *J. Bact.* 170:386-392 (1987); Jurgen Brosius, et al., Spacing of the −10 and −35 regions in the tac promoter. *J. Biol. Chem.* 260:3539-3541 (1985); Jensen, P. R., and Hammer, K., Artificial promoter for metabolic optimization. Biotechnol. Bioeng. 58:191-195 (1998); Patek, M. et al., Promoter from *Corynebacterium glutamicium*: cloning, molecular analysis and search for a consensus motif. *Microbiol.* 142:1297-1309 (1996); Shine, J. and Dalgarno, L., Determinant of cistron specificity in bacterial ribosome. *Science* 254:34-38 (1975); Shine J., and Dalgarno, L., Terminal-sequence analysis of bacterial ribosomal RNA. Correlation between the 3'-terminal-polypyrimidine sequence of 16-S RNA and translational specificity of the ribosome. *Eur. J. Biochem.* 57:221-230 (1975); Stormo, G. D., et al. Characterization of translational initiation sites in *E. coli. Nucleic Acids Res.* 10:2971-2996 (1982); de Boer, H. A., et al., A hybrid promoter and portable Shine-Dalgrano regions in *Escherichia coli. Biochem. Soc. Symp.* 48:233-244 (1983); Meinicke, P., et al., Oligo kernels for datamining on biological sequences: a case study on prokaryotic translation initiation sites. *BMC Bioinformatics* 5:169 (2004); Barrick, D., et al., Quantitative analysis of ribosome binding sites in *E. coli. Nucleic Acids Res.* 22:1287-1295 (1994); de Boer, H. A., et al., The tac promoter: a functional hybrid derived from the trp and lac promoters. *Proc. Natl. Acad. Sci. USA.* 80:21-25 (1983); Lithwick, G. and Margalit, H., Hierarchy of sequence-dependent features associated with prokaryotic translation. *Genome Res.* 13:2665-2673 (2003); Maloy, S. R., et al., Elevated levels of glyoxylate shunt enzymes in *Escherichia coli* strains constitutive for fatty acid degradation. *J. Bact.* 143:720-725 (1980); Ma, J. et al., Correlation between Shine-Dalgarno sequence and gene features such as predicted expression levels and operon structures. *J. Bact.* 184:5733-5745 (2002); Datsenko, K. A. and B. L. Wanner, One step inactivation of chromosomal genes in *Escherichia coli* K-12 using PCR products. *PNAS* 97:6640-6645 (2000); Ornston, L. N. and M. K. Omston, Regulation of glyoxylate metabolism in *Escherichia coli* K-12. *J. Bact.* 98:1098-1108 (1969); Alexeyev, M. F., et al. Improved antibiotic-resistance gene cassettes and omega elements for *Escherichia coli* vector construction and in vitro deletion/insertion mutagenesis. *Gene* 160:63-67 (1995); Cremer, J., et al., Regulation of enzymes of lysine Biosynthesis in *Corynebacterium glutamicum. J. Gen. Micro* 134:3221-3229 (1988); Blattner, et al., The Complete genome sequence of *Escherichia coli* K-12. *Science* 277:1453-1474 (1997).

Each of the foregoing references, and those in the description that follows, are incorporated herein by reference to the extent necessary to aid one of ordinary skill in the art to understand or practice the further teachings provided by the present disclosure.

There remains a need in the art for microorganism strains that are culturable and produce increased amounts of amino acids such as L-threonine, L-methionine, L-lysine, L-homoserine, and L-isoleucine.

BRIEF SUMMARY

The inventions described and claimed herein have many attributes and encompass many embodiments including, but not limited to, those set forth in this Summary. The inventions described and claimed herein are not limited to or by the features or embodiments identified in this Summary, which is included for purposes of illustration only and not restriction.

One aspect of the invention is to provide bacteria that efficiently produce an amino acid or amino acids (e.g. L-threonine, L-lysine, L-methionine, L-homoserine, and/or L-isoleucine) in large amounts and/or high yields. In general, bacteria of the invention do not have any unusual amino acid nutritional requirements, though one could of course design the bacteria such that unusual nutritional requirements (including, for example, the requirement that an amino acid or amino acids be supplied, or the requirement that the bacteria be grown on a particular medium) could exist. Bacteria of the invention may be from the family Enterobacteriaceae, including bacteria of the genus *Escherichia*, including strains of *Escherichia coli*. Bacteria of the invention may also be from the family Corynebacteriaceae, including bacteria of the genus *Corynebacterium* or *Brevibacterium*, including strains of *Corynebacterium glutamicum, Brevibacterium flavum*, and *Brevibacterium lactofermentum*. The distinction between *Corynebacterium* and *Brevibacterium* is slight, and some investigators assert that these bacteria are actually of the same genus. The accuracy of that distinction is not determinative of any aspect of the present invention, which may be practiced with any strain of bacterium that can be cultured to produce amino acids.

In one aspect the invention includes a strain of bacteria, wherein at least one chromosome of the strain contains at least one glcB gene, and/or aceA gene, and/or aceB gene operably associated with at least one non-native promoter, and wherein the strain over-produces L-threonine, L-methionine, L-homoserine, L-isoleucine and/or L-lysine. The strain may over-produce L-threonine when compared to L-threonine production by a wild-type strain of *E. coli*, for example the *E. coli* strain K-12, and/or when compared to a parent strain.

In a further aspect of the invention, a strain of *E. coli* further comprises a non-native ribosome binding site operably associated with said aceB, aceA and/or glcB gene(s) and said non-native promoter. A non-native ribosome binding site may be selected from, for example, but is not limited to, a lac ribosome binding site, a thrA ribosome binding site, a folA ribosome binding site, an araC ribosome binding site, an araB ribosome binding site, a galE ribosome binding site, an ompA ribosome binding site, a trpE ribosome binding site, a lamB ribosome binding site, an MS2 coat ribosome binding site, and a Qβ coat ribosome binding site.

In one aspect of the invention, the non-native ribosome binding site used in the invention is selected from a strain of *E. coli*. For instance, the non-native ribosome binding site may be selected from *E. coli* strain s4370-69-2. References to ribosome binding sites may include but not be limited to consensus sequences, sequences found in nature, and mutated sequences.

A non-native promoter and/or a non-native ribosome binding site may be introduced, for example, by recombination or by mutagenesis of a native aceBAK or glcB promoter or binding site.

In a yet further aspect of the invention, the previously discussed non-native promoter may be selected from at least one of the group consisting of, for example, a tac promoter, a trc promoter, a lac promoter, a lpp promoter, a trp promoter, a lambda-$P_L$ promoter, a lambda-$P_R$ promoter, a lacUV5 promoter, an araBAD promoter, and a lpp-lac promoter. References to promoters may include but not be limited to consensus sequences and mutated sequences. Those skilled in the art may recognize, with the benefit of this disclosure and with the benefit of Brosius, et al., supra., and Mulligan, et al., supra, that similar results may be obtained using the trc promoter in examples that teach use of the tac promoter.

In one aspect, the invention includes a process for production of an L-amino acid product by fermentation comprising growing in a fermentation medium a bacterium that produces the L-amino acid and that contains a recombinant nucleic acid construct operably configured to overexpress at least one gene selected from the group consisting of a gene in an aceBAK operon and a glcB gene in the bacterium; enriching the L-amino acid in at least one of the fermentation medium and in the bacterium; and isolating the L-amino acid from at least one of the fermentation medium and the bacterium to produce an L-amino acid product. In a further aspect of the invention, the genus of the aforementioned bacterium is selected from the group consisting of *Escherichia, Corynebacterium*, and *Brevibacterium*. The bacterium may be, for example, *E coli.*

In a yet still further aspect of the invention, the recombinant nucleic acid comprises a non-native promoter sequence upstream of at least one gene in the aceBAK operon and/or the glcB gene, wherein the non-native promoter is operably associated with the at least one gene in the aceBAK operon and/or the glcB gene. The promoter may be selected from a tac promoter, a trc promoter, a lac promoter, a lpp promoter, a trp promoter, a lambda $P_L$ promoter and a lambda $P_R$ promoter, or other promoters that will be recognized by those skilled in the art with the benefit of this disclosure.

The over-expressed gene may be selected from aceB, aceA, and glcB. The non-native promoter may replace a native promoter in the operon, wherein the native promoter is deleted, interrupted, or partially deleted and partially interrupted. The non-native promoter may be inserted in addition to a native promoter in the operon.

In yet another aspect of the invention, a process for production of an L-amino acid product is provided as above, wherein at least one of the aceBAK gene product and glcB gene product are the only gene product(s) over-expressed in the microorganism.

In another aspect of the invention, the L-amino acid is selected from the group consisting of L-threonine, L-isoleucine, L-homoserine, L-lysine and L-methionine. In a further aspect, the L-amino acid is L-threonine.

In a further aspect, the invention includes a bacterium in which at least one of the genes in the aceBAK operon and the glcB gene is over-expressed. The genus of the microorganism may be selected from the group consisting of *Escherichia, Corynebacterium*, and *Brevibacterium*. The bacterium may be a strain of *E. coli*. Those skilled in the art will, with the benefit of this disclosure, recognize that teachings herein applicable to isocitrate lyase and malate synthase G and the genes encoding them in *E. coli* may be applied to isocitrate lyase and malate synthase G in *Corynebacterium*. The gene encoding malate synthase G in *Corynebacterium glutamicum* strain ATTC 13032 (glcB) is shown in SEQ ID NO: 26. The gene encoding isocitrate lyase in *Corynebacterium glutamicum* strain ATTC 13032 (aceA) is shown in SEQ ID NO: 27.

In a further aspect of the invention, the bacterium is a strain of *Escherichia coli, Brevibacterium lactofermentum, Brevibacterium flavum*, or *Corynebacterium glutamicum.*

In another aspect of the invention, the bacterium includes at least one gene in the aceBAK operon and/or a glcB gene that is regulated by a non-native promoter. In another aspect, a non-native promoter in a bacterium of the invention is selected from a tac promoter, a trc promoter, a lac promoter, a lpp promoter, a trp promoter, a lambda $P_L$ promoter and a lambda $P_R$ promoter. In a yet still further aspect of the invention, the non-native promoter is a tac promoter (Ptac).

A further aspect of the invention includes a bacterium in which a native promoter in an aceBAK operon is replaced, interrupted, or partially replaced and partially interrupted by a non-native promoter. In another aspect of the invention, a bacterium of the invention includes a non-native promoter inserted in an aceBAK operon without replacing or interrupting a native promoter in an aceBAK operon. In a further aspect of the invention, in a bacterium of the invention a native promoter in the glcDFGB operon has been replaced or interrupted by a non-native promoter in operable association with the glcB gene. In a further aspect of the invention, a bacterium of the invention is provided wherein a non-native promoter is inserted in a glcDFGB operon in operable association with the glcB gene without replacing or interrupting a native promoter in that glcDFGB operon.

A further aspect of the invention provides the bacterial strains deposited on May 11, 2005, and given the deposit numbers NRRLB-30844, NRRLB-30845, NRRLB-30846, NRRLB-30847, NRRLB-30848, NRRLB-30849, NRRLB-30850, and NRRLB-30851. Embodiments also provide bacterial strains that are derivatives of those deposited microorganisms. For example, those skilled in the art will recognize that various modifications may be performed on the deposited strains, including further modification of the metabolic flux, as well as alterations to the nutritional requirements, without diminishing the overexpression of the aceBAK operon or glcB gene.

In a still further aspect, the invention includes a recombinant nucleic acid that comprises a non-native promoter operably configured to overexpress a gene that encodes at least one of an *E. coli* aceA protein, aceB protein, and glcB protein in a bacterium, and wherein said gene includes at least one of:

a) DNA that encodes a protein selected from the group consisting of SEQ ID NOS.: 3, 5, 8 b) a nucleic acid according to at least one of SEQ ID NO:9, SEQ ID NO: 19, SEQ ID NO: 20, SEQ ID NO: 21, SEQ ID NO: 22, SEQ ID NO: 23, SEQ ID NO: 24, and SEQ ID NO: 25, c) a nucleic acid that is degenerate only with respect to the genetic code to the nucleic acid according to b), d) a nucleic acid that contains a silent mutation of the nucleic acid according to a) or b), e) a nucleic acid that is at least 80%, preferably at least 90%, and more preferably at least 95% identical to the nucleic acid of b), f) a nucleic acid that hybridizes, under stringent conditions, with the DNA according to b).

In a further aspect, the invention provides a vector containing at least one polynucleotide as described in a), b), c), d), or e) of the preceding paragraph.

BRIEF DESCRIPTION OF THE FIGURES

FIG. 4 shows the 5'-3' sequence of primers used in the construction of strains listed in this document. Underlined residues provide sequence homology to either the aceB allele or to the glcB allele and allow insertion into the chromosome via homologous recombination. Bold residues encode the tac promoter.

FIG. 5 shows the tac promoter and seven different Ptac-gene fusions, including a sequence of the tac promoter (Ptac) (SEQ ID NO: 9) and the sequences of promoter regions of seven different Ptac insertion constructs with the start codon (ATG) boxed. Ptac-aceBAK (SEQ ID NO: 19) is shown as found in strain s4397-184-1 and strain s4538-006-1. Ptac(2)-aceB (SEQ ID NO: 20) is shown as found in strain s4480-140-5. Ptac(3)-aceBAK (SEQ ID NO: 21) is shown as found in strain s4480-148-1. Ptac(4)-aceBAK (SEQ ID NO: 22) is shown as found in strain s4480-199-1. Ptac(5)-aceBAK (SEQ ID NO: 23) is shown as found in strain s4538-003-1. Ptac\lac-aceBAK (SEQ ID NO: 24) is shown as found in strain s4480-199-4. Ptac-glcB (SEQ ID NO: 25) is shown as found in strain s4397-109-2 and in strain s4538-006-1.

Figure 1:
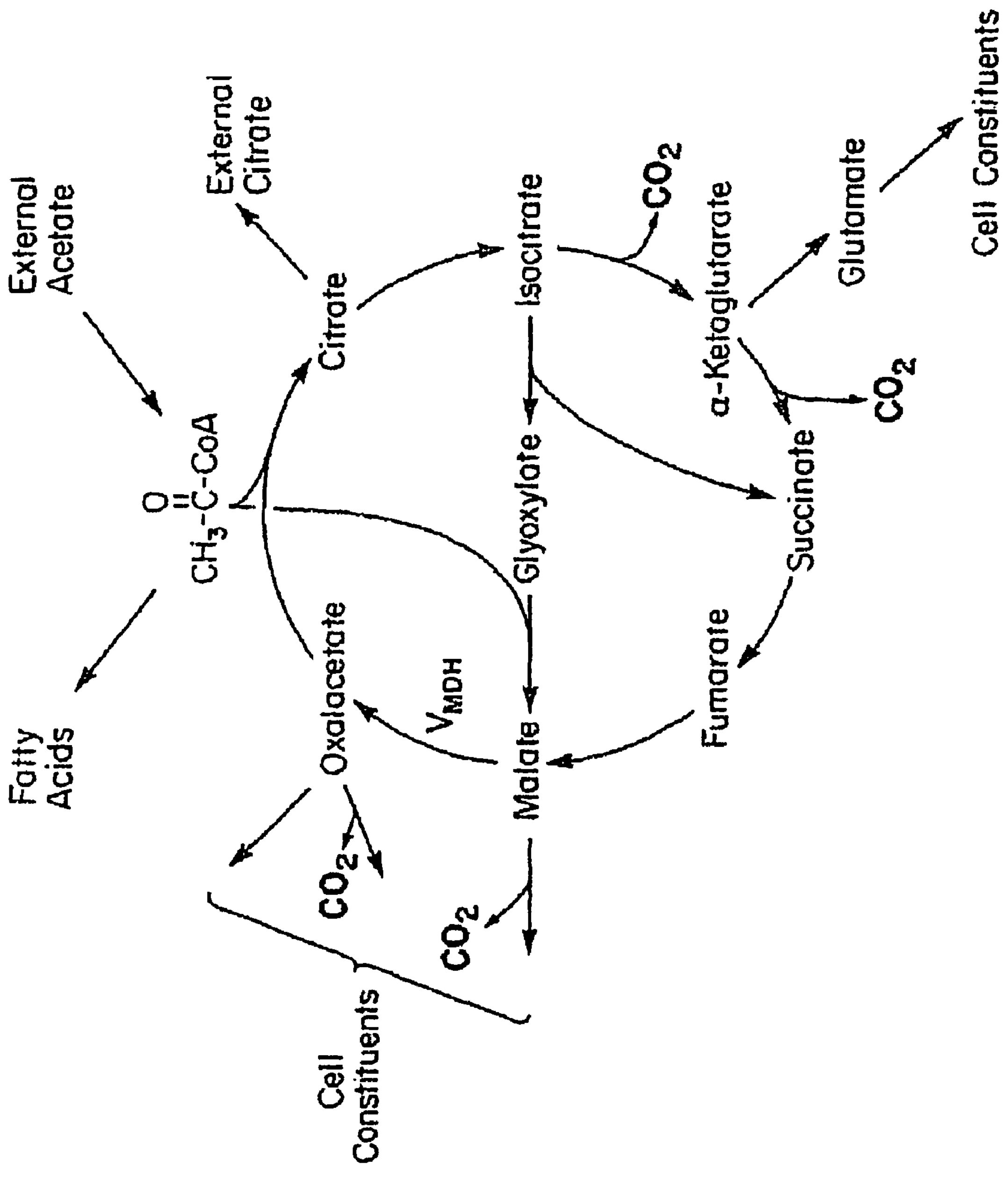
FIG. 1 depicts the tricarboxylic acid cycle of *E. coli*. Figure from L. N. Omston, et al., *J. Bact.,* 98:2, 1098-1108 (1969).
Figure 2:
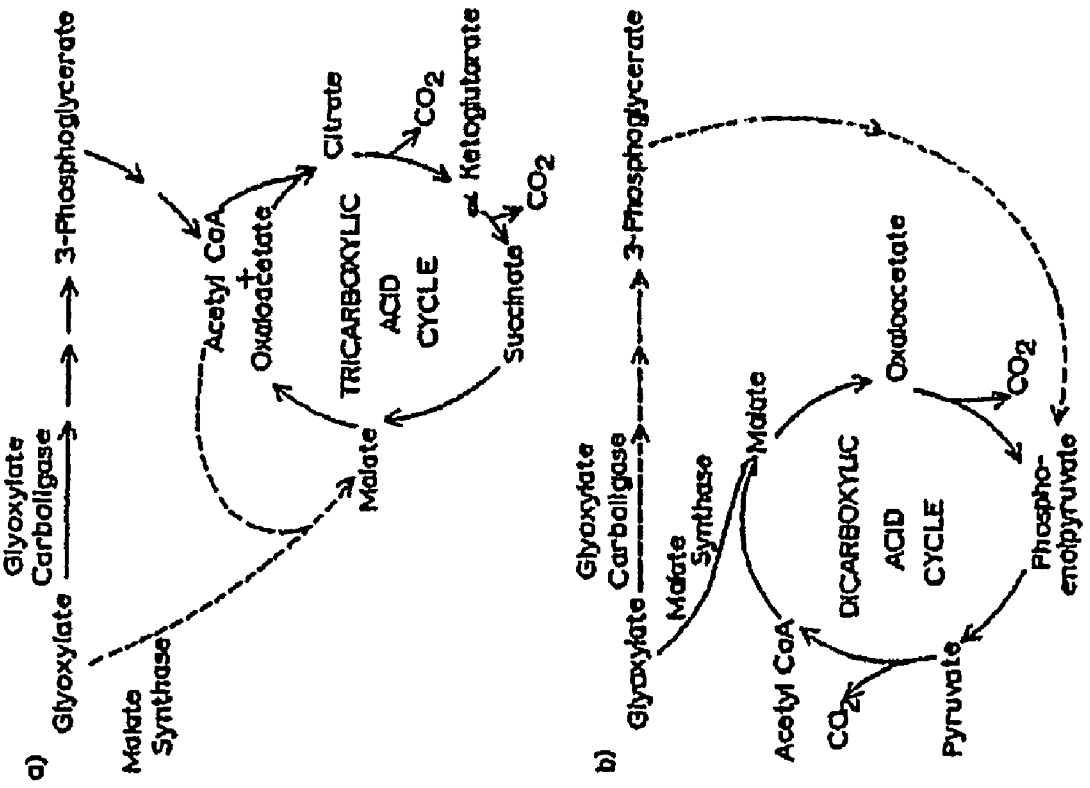
FIG. 2 depicts the glyoxylate shunt in *E. coli*. Figure modified from K. Walsh et al., *J. Biol. Chem.* 259:15, 9646-9654 (1984).

Table 1 shows strain numbers and relevant genotypes of strains presented in this document. Table 1 also presents primers and templates used in the PCR amplification of DNA used to construct strains listed in this document.

Table 2 lists the malate synthase (MS) and isocitrate lyase (ICL) specific activities of various strains carrying tac promoter fusions.

Table 3, Table 4 and Table 5 list results of shake flasks experiments measuring threonine titers and yields of tac promoter fusion strains.

DETAILED DESCRIPTION

As discussed below, the invention provides microbial strains possessing improved properties for production of aspartate-derived amino acids and chemicals. Methods of making such strains are provided. These methods include altering expression of the aceBAK operon, the aceA gene, the aceB gene, the glcB gene, or combinations thereof. Alteration of expression may be accomplished through increased transcription, and/or relief from native transcriptional control. Replacement of native promoters for these genes is also contemplated; for instance, their native promoters may be replaced by the tac promoter (Ptac). Gene constructs providing novel features of the invention are also provided, including vectors, where such vectors may be, but are not limited to, a plasmid, a cosmid, a virus, a phage, a transposon, or a minichromosome.

I. Definitions

Certain terms used herein are used by those of ordinary skill in this art and have an ordinary meaning commonly understodd by such persons. The fullest scope of such ordinary meanings are intended to be embraced herein. However, to provide a clear and consistent understanding of the specification and claims, including the scope to be given to terms therein, the following definitions are provided, for cases where a meaning is asserted that may conflict with the definitions provided herein, in which case the provided definitions control. Note that the term "a" or "an" entity refers to one or more of that entity; for example, "a polynucleotide" is understood to represent one or more polynucleotides. As such, the terms "a," "an," "one or more," and "at least one" can be used interchangeably herein.

Chromosomal Integration. As used herein, the term "chromosomal integration" refers to insertion of an exogenous DNA fragment into the chromosome of a host organism.

Constitutive. As used herein, the term "constitutive" refers to a promoter that is expressed and not known to be subject to regulation that completely causes cessation of expression; that is, it is always "on."

Endogenous. As used herein, the term "endogenous" refers to a DNA sequence in an organism that is a naturally occurring within that organism.

aceA gene. As used herein, the term "aceA gene" refers to a nucleic acid sequence encoding a protein that has isocitrate lyase activity. Isocitrate lyase catalyzes the reversible cleavage of isocitrate to glyoxylate and succinate in the glyoxylate cycle. One example of an aceA gene encodes the protein according to SEQ ID NO: 3. Other examples of isocitrate lyase gene sequences from various bacterial strains include those that encode the proteins according to SEQ ID NOs: 28 through 35. Typical examples of aceA genes include the nucleic acid sequences set forth in SEQ ID NO: 2 and SEQ ID NO: 27. Other examples of aceA genes from various bacterial strains include those according to SEQ ID NOs: 36 through 41.

aceB gene. As used herein, the term "aceB gene" refers to a nucleic acid sequence encoding a protein that has malate synthase A activity. This activity catalyzes the reaction of acetyl-CoA with glyoxylate and water to form S-malate and CoA. Examples of aceB genes from various bacterial strains include those that encode the proteins according to SEQ ID NOs: 42 through 48. Typical examples of aceB genes include the nucleic acid sequences set forth in SEQ ID NO: 4 and SEQ ID NO: 26. Other typical examples of aceB genes from various bacterial strains include those according to SEQ ID NOs: 49 through 53.

glcB gene. As used herein, the term "glcB gene" refers to a nucleic acid sequence encoding a protein that has malate synthase G activity. This activity also catalyzes the reaction of acetyl-CoA with glyoxylate and water to form S-malate and CoA. One example of a glcB gene encodes the protein according to SEQ ID NO:8. Protein sequences that have malate synthase G activity may be distinguished from those having malate synthase A activity by having greater amino acid sequence identity to SEQ ID NO: 8 than SEQ ID NO: 42. Typical examples of glcB genes from various bacterial strains include those that encode the proteins according to SEQ ID NO: 7. Other typical examples of glcB genes from variou bacterial strains inclue those according to SEQ ID NOs: 58 through 60.

Heterologous. As used herein, the term "heterologous" refers to structures from different sources or from different locations within the same source.

Inducer. As used herein, the term "inducer" refers to a molecule that acts to stimulate transcription from an inducible promoter. The presence of an inducer (usually, but not always, an external molecule) stimulates transcription.

Isolated Polynucleotide. As used herein, the term "isolated polynucleotide" means a polynucleotide, DNA or RNA, that has been removed from its native environment. For example, recombinant DNA molecules contained in a vector are considered isolated. Further examples of isolated DNA molecules include recombinant DNA molecules maintained in heterologous host cells or purified (partially or substantially) DNA molecules in solution. A nucleic acid molecule contained in a clone that is a member of a mixed clone library and that has not been isolated from other clones of the library or a chromosome isolated or removed from a cell or a cell lysate, is not "isolated." Isolated RNA molecules include in vivo or in vitro RNA transcripts of DNA molecules included in the invention. Isolated DNA also includes DNA that is produced by PCR amplification.

Recombinant nucleic acid. As used herein, the term "recombinant nucleic acid" means a polynucleotide sequence that has been manipulated to fuse together nucleic acids from herterologous sources.

Native promoter. As used herein, the term "native promoter" refers to a promoter that is an endogenous promoter operably associated with a gene in a parent strain.

Non-native promoter. As used herein, the term "non-native promoter" refers to a promoter that is either an endogenous promoter that is operably associated with a different gene than that with which it is operably associated in the microorganism as it is found in nature. A non-native promoter may also be a heterologous promoter.

A non-native promoter may also be a promoter that has had its sequence changed, deleted, replaced, and/or mutated with reference to a parent strain. Such change, deletion, replacement, and/or mutation may come about through any mechanism. Some possible mechanisms include but are not limited to chemical mutagenesis, ultraviolet mutagenesis, recombination, or other means as will be recognized by those skilled in the art. A non-native promoter may be created by one or more changes, deletions, replacements, or mutations. A non-native promoter may be created by multiple and/or successive mutations, changes, deletions, and/or replacements to a series of parental strains.

Operably associated. As used herein, the term "operably associated," "operably linked," and "operably configured" are used interchangeably and refer to an association of nucleic acid elements in a functional relationship. A nucleic acid sequence is "operably associated" with another nucleic acid sequence when it is placed into a functional relationship with another nucleic acid sequence. For instance, a promoter is operably associated with a polypeptide coding region if it affects the transcription of the polypeptide coding region. Operably associated nucleic acids are typically close together or contiguous and, where necessary, optimal, or useful, join two polypeptide coding regions contiguously and under common transcriptional control, such as in an operon.

Operon. As used herein, the term "operon" refers to a contiguous portion of a nucleic acid sequence that encodes a mRNA in which two or more open reading frames encoding polypeptides are transcribed as a multi-cistronic messenger RNA, and controlled by a cis-acting promoter and possibly other cis-acting regulatory sequences operational for molecular control of transcription.

Promoter. As used herein, the term "promoter" denotes a portion of a DNA sequence that provides for binding of RNA polymerase and initiation of transcription and thus refers to a DNA sequence capable of promoting expression of a coding sequence or other functional RNA in a cell. Promoter sequences are commonly, but not always, found in the 5' non-coding regions of genes, upstream of one or more open reading frames encoding polypeptides. Sequence elements within promoters that function in the initiation of transcription are often characterized by consensus nucleotide sequences. A promoter sequence may include both proximal and more distal upstream elements. Examples of conserved proximal elements in bacterial promoters include the −10 region and the −35 region, located 10 and 35 bases, respectively, upstream of the point of transcriptional initiation. A promoter may be, for example, constitutive, inducible, or environmentally responsive.

A promoter may be derived in its entirety from a native gene or may be a hybrid promoter. Hybrid promoters are composed of different elements derived from different promoters found in nature, and/or may comprise synthetic DNA segments.

Over-produce. As used herein, the term "over-produce" refers to the production of a compound by a cell in an amount greater than the amount produced by a reference strain. A reference strain may be, for example, a parent strain used to produce a strain of the invention. A reference strain may also be a wild-type strain.

Overexpress. As used herein the term "overexpress" means a gene product (RNA and/or protein) is overproduced in a progeny organism that has been manipulated by mutation, crossing, or recombinant DNA techniques relative to a wild type strain, or parent organisms not so manipulated.

Strain. As used herein, the term "strain" refers to bacteria of a particular species that have identical or substantially identical phenotypic and genotypic characteristics. Unless indicated to the contrary, the terms "strain" and "cell" are used interchangeably herein.

Suppressor and Repressor. As used herein, the terms "suppressor" and "repressor" refer to different types of molecules that act to block or reduce transcription from a derepressable promoter. A supressor is a small molecule that binds to a receptor protein of some type, which binding leads to a suppression of gene expression. A repressor is a protein that binds to a cis-acting transcriptional regulatory element of a promoter, which binding causes a suppression of transciption from the promoter. Suppressors and repressors are often produced within a host cell. Suppressors may be added to a medium in which a host cell is being grown or will be grown.

Synthetic promoter. As used herein, the term "synthetic promoter" means a nucleotide sequence having promoter activity and that is not known to be found in nature.

Yield. As used herein, the term "yield" refers to the amount of a product produced in relation to the amount of a raw material consumed. With respect to amino acids produced by a microorganism, yield refers to the amount of amino acid produced with respect to the amount of raw material consumed by the process. For example, when 100 grams of dextrose is consumed by a microorganism that produces 25 grams of L-isoleucine, the yield of L-isoleucine, with respect to the dextrose, is 25%.

Cosmid. As used herein, the term "cosmid" refers to a hybrid vector comprised of plasmid sequences and the cohesive ends of bacteriophage lambda.

Exogenous. As used herein, the term "exogenous" refers to a DNA sequence in an organism that is not naturally occurring within that organism.

Extrachromosomal element. As used herein, the term "extrachromosomal element" refers to elements not associated with a chromosome. Extrachromosomal elements of the invention include, for example, but are not limited to, vectors. A vector may be, for example, but is not limited to a plasmid, cosmid, virus, phage transposon or minichromosome.

Homologous. As used herein, the term "homologous" refers to structures from the same source, or having the same evolutionary structure or function.

Homologous Recombination. As used herein, the term "homologous recombination" refers to the exchange of homologous or nearly homologous sequences between two DNA molecules.

Parent Strain. As used herein, the tem "parent strain" refers to a strain of microorganism that is mutated, electroporated, or otherwise changed to provide a strain or host cell of the invention, or a strain that precedes a strain that has been mutated, electroporated, or otherwise changed to provide a strain or host cell of the invention.

Plasmid. As used herein, the term "plasmid" refers to a circular extrachromosomal element that may be used as a vector for cloning.

Endogenous Promoter. As used herein, the term "endogenous promoter" refers to a promoter sequence that is a naturally occurring promoter sequence within the wild-type of a selected host microorganism.

Heterologous Promoter. As used herein, the term "heterologous promoter" refers to a promoter sequence that is a non-naturally occurring promoter sequence in a selected host microorganism. A non-naturally occurring promoter sequence may be from any prokaryotic or eukaryotic organism.

Regulation. As used herein, the term "regulation" refers to the rising and falling levels of some gene products in response to molecular signals. These gene products may be, for example, but are not limited to proteins and mRNA. Regulation may be "positive regulation," (or "induction") in which gene products increase under particular circumstances. Regulation may be "negative regulation," (or "repression") in which gene products decrease under particular circumstances.

Ribosome binding site (RBS). As used herein, the term "ribosome binding site" refers to a region of an mRNA molecule that binds a ribosome to initiate translation.

Vector. As used herein, the term "vector" refers to a DNA molecule capable of replication in a host organism.

Unless otherwise indicated, all nucleotide sequences newly described herein were determined using an automated DNA sequencer (such as the Model 373 from Applied Biosystems, Inc.). Therefore, as is known in the art, for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule.

II. Strains and Nucleotides

Aspects of the invention include both methods of producing cells that over-produce an amino acid or amino acids as well as cells produced by those methods, descendants of those cells, and cells with similar characteristics. Although the invention is discussed herein in the context of the production of L-threonine, it is to be understood that methods, strains, and constructs of the invention may be used to produce other amino acids or chemicals derived from aspartate, including but not limited to L-methionine, L-isoleucine, L-homoserine, and L-lysine Bacteria and methods of the invention may be made with or with a "knock-out" of an existing promoter or gene. A "knock out" physically displaces a promoter or gene by insertion or deletion so that the promoter or gene is non-functional. When a non-native promoter is operably associated with the aceBAK operon or glcB gene, the native promoter may be interrupted or deleted (either in whole or in part). Alternatively, the non-native promoter may be placed either upstream or downstream of the native promoter for the gene with which the non-native promoter is operably associated without knocking out the functional acticity of the native promoter. In such cases, however, the non-native promoter will also function to promote transcription in a manner that is independent of the native promoter.

A number of promoters are suitable for the invention. They include, for example, but are not limited to, the promoters tac, trc, lac, lpp, trp, lambda $P_L$, lambda $P_R$, lacUV5, araBAD, lpp-lac, phoA, recA, proU, cst-1, tetA, cadA, nar, cspA, T7, T7lac, T3lac, T-lac, T4 gene 32, nprMlac, VHb, and Protein A. An exemplary nucleotide sequence for a tac promoter (SEQ ID NO: 9) (*Proc. Natl. Acad. Sci.* 80:21-25., de Boer et al.) is set forth in FIG. 5. Sequences for other promoters are known to those skilled in the art, and their use in the invention will be evident with the benefit of this disclosure.

A chromosome or chromosomes of the strains of the invention may include more than one aceBAK operon and/or glcDFGB operon or glcB gene, and each operon or gene may independently have either a non-native or native promoter operably associated with that operon or gene. If there is more than one aceBAK operon, glcDFGB operon and/or glcB gene in a chromosome, they may include non-native promoters that are the same or different.

In addition to including a promoter that is not a native aceBAK operon, glcDFGB operon and/or glcB gene promoter operably associated with at least one aceBAK operon, glcDFGB operon and/or glcB gene, a strain of the invention may include a ribosome binding site operably associated with aceBAK operon, glcDFGB operon and/or glcB gene and a non-native promoter, where the ribosome binding site is either a native aceBAK operon, glcDFGB operon and/or glcB gene ribosome binding site or a non-native ribosome binding site. Non-native ribosome binding sites for use in the invention include a ribosome binding sites from lac, thrA, folA, araC, araB, galE, ompA, trypE, lamB, MS2 coat and QB coat.

It should be understood that throughout this disclosure, nucleotide sequences and/or promoters disclosed in this invention should be construed to include both the consensus sequences for those sequences and/or promoters, and, in some aspects of the invention, nucleotide sequences that are at least 90%, 91%, 92%, 93%, 94%, 95%, 96%, 97%, 98%, 99%, or 100% identical to a disclosed sequence.

As a practical matter, whether any particular nucleotide sequence is at least 90%, 91%, 92%, 93%, 94%, 95%, 96%, 97%, 98%, 99%, or 100% identical to a nucleotide sequence or complementary nucleotide sequence can be determined conventionally using sequence analysis computer programs such as OMIGA® Version 2.0 for Windows, available from Oxford Molecular, Ltd. (Oxford, U.K.). OMIGA® uses the CLUSTAL W alignment algorithm using the slow full dynamic programming alignment method with default parameters of an open gap penalty of 10 and an extend gap penalty of 5.0, to find the best alignment between two nucleotide sequences. When using CLUSTAL W or another sequence alignment program to determine whether a particular sequence is, for instance, 95% identical to a reference sequence, the parameters may be set such that the percentage of identity is calculated over the full length of the reference nucleotide sequence such that gaps, mismatches, or insertions of up to 5% of the total number of nucleotides in the reference sequence are allowed. Other sequence analysis methods and programs as known in the art may be used in the invention.

Experiments described in this disclosure used the GCG® Wisconsin Package® (Wisconsin Package Version 10.3, or 11.1, Accelrys Inc., San Diego, Calif. Portions of SeqLAb are based on the "Genetic Data Environment (GDE)", originally developed in the Department of Microbiology, University of Illinois, Urbana-Champaign, Ill., USA, and licensed to GCG), a sequencing program available from Accelrys®. Elements of the Wisconsin Package® that were used include GAP, SSEARCH, FASTA, and BLAST.

Bacterial strains s4397-184-1, s4480-140-5, s4480-148-1, s4480-199-1, s4538-003-1, s4480-199-4, s4397-109-2, and s4538-006-1, deposited on May 11, 2005, at the National Center for Agricultural Utilization Research in Peoria, Ill. and given, respectively, the deposit numbers NRRLB-30844, NRRLB-30845, NRRLB-30846, NRRLB-30847, NRRLB-30848, NRRLB-30849, NRRLB-30850, and NRRLB-30851 demonstrate various aspects of the invention. For instance, in s4397-184-1 the tac promoter has been operably associated with the aceBAK operon in *E. coli*. This strain is capable of increased malate synthase A activity and increased threonine titer when compared to the malate synthase activity and threonine titer in wild-type *E. coli* when tested in a shake flask. Results with these strains are set forth more fully in Example 4 and Example 5, below.

In a still further aspect, the invention includes a nucleic acid that includes a non-native promoter operably associated with at least one of an aceA gene, an aceB gene, and a glcB gene, wherein the nucleic acid encodes, respectively, at least one of isocitrate lyase, malate synthase A, or malate synthase G. Non limiting examples of the polypeptides corresponding to the aceA gene include the protein according to SEQ ID NO:3 and SEQ ID NOs: 28 through 35. Typical examples of aceA genes include the nucleic acid sequences set forth in SEQ ID NO:2 and SEQ ID NO: 27. Other examples of aceA genes from various bacterial strains include those according to SEQ ID NOs: 36 through 41. Non-limiting examples of the polypeptides corresponding to the aceB gene include the protein according to SEQ ID NOs: 42 through 48. Non-limiting examples of the polypeptides corresponding to the glcB gene include the proteins according to SEQ ID NO: 8 and SEQ ID NOs: 54 through 57. NON-limiting examples of the foregoing polynucleotides are the nucleic acids according to SEQ ID NO: 9, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NOs: 36 through 41, SEQ ID NOs: 45 through 53, and SEQ ID NOs: 58 through 60.

The polynucleotide may also be DNA according to one of the preceding polynucleotide sequences that is degenerate thereto with respect to the genetic code or DNA containing silent mutations of the foregoing sequences. Such silent mutations are discussed in Bowie, J. U., et al., "Deciphering the Message in Protein Sequences: Tolerance to Amino Acid Substitutions," Science 247:1306-1310 (1990). The polynucleotides may also be DNA that is at least 80%, preferably at least 90%, and more preferably at least 95% identical to the DNA, DNA with degenerate alterations, or DNA with silent alterations as discussed above, or a polynucleotide that hybridizes under stringent hybridization conditions to any DNA discussed above. The invention may also include a vector that provides any of the polynucleotides of this paragraph.

III. Dna Constructs

In another aspect, the invention includes DNA constructs (e.g. vectors) that comprise at least a portion of an *E. coli* aceBAK operon and/or glcDFGB operon, for instance the glcB gene, aceA gene, and/or aceB gene, operably associated with at least one promoter that is not a native promoter. DNA constructs of the invention may further include a ribosome binding site that is not the native *E. coli* gene ribosome binding site for the included gene, for instance the lac ribosome binding site. Of course, DNA constructs of the invention may include other regulatory elements or additional DNA elements known to those in the art.

DNA constructs of the invention may be a vector or vectors. Vectors of the invention may comprise at least one regulatory element. For example, a regulatory element may be a promoter, operator, activator, repressor, and/or enhancer. Vectors may also comprise an initiation sequence or sequences and/or a ribosome binding site or ribosome binding sites. Vectors may further comprise a selectable marker. Regulatory elements may be located on chromosomes of host cells and/or within other vectors.

In one aspect of the invention, a DNA construct is provided comprising an aceA gene, aceB gene, or glcB gene operably associated with at least one promoter heterologous to *Escherichia coli*. In a further aspect of the invention, a DNA construct further comprises at least one ribosome binding site operably associated with an aceA gene, aceB gene, or glcB gene and a promoter that is not the native *E. coli* aceA, aceB, or glcB promoter, wherein said at least one ribosome binding site is not the native *E. coli* ribosome binding site for those genes.

Vectors of the invention may be, but are not limited to, a plasmid, a cosmid, a virus, a phage, a transposon, or a minichromosome. In a further aspect of the invention, a promoter operably associated with an aceA gene, aceB gene, or glcB gene in a DNA construct may be, for example, but is not limited to, tac, trc, lac, lpp, trp, lambda $P_L$, lambda $P_R$, lacUV5, araBAD, lpp-lac, phoA, recA, proU, cst-1, tetA, cadA, nar, cspA, T7, T7lac, T3lac, T-lac, T4 gene 32, nprM-lac, VHb, and Protein A.

In a further aspect of the invention, a host cell is provided that includes a DNA construct of the invention. A host cell may be a microorganism, including, for example, an *E. coli* cell, and may include further modifications or inclusions as may be desired by those skilled in the art. The host cell may produce L-threonine. In one aspect, the host cell produces L-threonine in higher yield than a parent cell that does not bear at least one DNA construct of the invention.

IV. Culture Media and Processes for Amino Acid Production

The invention is also directed to use of the above-described and below-claimed strains and host cells in fermentation processes for production of amino acids in general. Such amino acids may include, for example, amino acids of the aspartate family. Amino acids of the aspartate family may include, for example, L-threonine, L-methionine, L-isoleucine, L-homoserine and L-lysine. Amino acids may be obtained, for example, by culturing strains or host cells of the invention in a synthetic or natural medium containing at least one carbon source, at least one nitrogen source, and, as appropriate, inorganic salts, growth factors, and the like.

Examples of suitable carbon sources include but are not limited to carbohydrates, such as dextrose, fructose, starch, sucrose, starch hydrolysate, cellulose hydrolysate and molasses; organic acids, such as acetic acid, propionic acid, formic acid, malic acid, citric acid, and fumaric acid; and alcohols, such as glycerol and ethanol.

Examples of suitable nitrogen sources include but are not limited to ammonia, including ammonia gas and aqueous ammonia; ammonium salts of inorganic or organic acids, such as ammonium chloride, ammomium phosphate, ammonium sulfate, and ammonium acetate; and other nitrogen-containing substances, including meat extract, peptone, corn steep liquor, casein hydrolysate, soybean cake hydrolysate and yeast extract.

Culture media suitable for use with the invention includes but is not limited to the following media:

1. Minimal Medium. Davis minimal media (per 1 liter 7.0 g dipotassium phosphate, 2.0 g monopotassium phospate, 0.5 g/l sodium citrate, 0.1 magnesium sulfate, 1.0 g ammonium sulfate, pH 7.0 supplemented with a carbon source (typically dextrose) to 0.1% (w/v) and supplemented as needed with a source of amino acids (typically 0.1% casamino acids (w/v) or 0.15% yeast extract (w/v)).

2. LB (10 g/l tryptone, 5 g/l yeast extract 10 g/l NaCl)

3. BTY2 (1.0 g/l K2HPO4, 10.0 g/l (NH4)2SO4, 40.8 g/l Bis-Tris, 15 g/l yeast extract (Difco), 32.5 g/l dextrose, and 1.2 g/l MgSO4-7H2O pH 7.0)

3. BTC3 (1.0 g/l K2HPO4, 10.0 g/l (NH4)2SO4, 40.8 g/l Bis-Tris, 20 ml/l 50% solids corn steep liquor (Sigma), 25.0 g/l dextrose, and 1.2 g/l MgSO4-7H2O pH 7.0 supplemented as needed with amino acids source (typically 1.0% casamino acids or 1.5% yeast extract (w/v)).

Amino acids may be commercially produced using strains of the invention in, for example, batch type or fed-batch type fermentation processes. In batch type fermentations, nutrients are added at the beginning of the fermentation. In fed-batch or extended fed-batch type fermentations one or more nutrients are supplied (1) continuously to the culture, (2) from the beginning of the fermentation or after the culture has reached a certain age, and/or (3) when the nutrient(s) that are fed are exhausted from the culture medium.

A variation of the extended batch of fed-batch type fermentation is the repeated fed-batch or fill-and-draw fermentation, where part of the contents of the fermentor may be removed at a particular time (e.g., when the fermentor is full) while feeding of a nutrient is continued. In this way, a fermentation can be extended for a longer time as compared to when such methods are not used.

Another type of fermentation, continuous fermentation or chemostat culture, uses continuous feeding of a complete medium while culture fluid is continuously or semi-continuously withdrawn in such a way that the volume of the broth in the fermentor remains approximately constant. A continuous fermentation can in theory be maintained for an infinite period of time.

In a batch fermentation, the cultured organism grows until either one of the essential nutrients in the medium becomes exhausted or fermentation conditions become unfavorable (e.g., the pH decreases to a value inhibitory for microbial growth). In fed-batch fermentations measures are normally taken to maintain favorable growth conditions (e.g., by using pH control) and exhaustion of one or more essential nutrients is prevented by feeding these nutrient(s) to the culture. Cultured microorganism will normally continue to grow at a rate determined by the rate of nutrient feed.

In some instances a single nutrient, very often a carbon source, will become limiting for growth. The same principle applies during continuous fermentation, in which one nutrient in the medium feed may be limiting and all of the other nutrients are in excess. After the microorganisms have stopped growing, the limiting nutrient will generally be present in the culture fluid in an extremely low concentration.

While different types of nutrient limitation can be employed, carbon source limitation is used most often. Other examples of limiting nutrients include the nitrogen, sulfur, phosphorous, trace metal, and oxygen sources. Vitamins and amino acids may also be limiting nutrients, particularly where a microorganism being cultured is auxotrophic for a limiting amino acid or vitamin.

After cultivation, amino acids (e.g., L-threonine, L-methionine, L-homoserine, L-lysine or L-isoleucine) that have accumulated in the culture broth may be partially or fully separated from the broth according to one or more of a variety of methods. For example, ion-exchange resins reportedly may be used to purify L-threonine according to methods described in U.S. Pat. No. 5,342,766. This method involves first removing the microorganisms from the culture broth by centrifugation and then adjusting the pH of the broth to about 2 using hydrochloric acid. The acidified solution is subsequently passed through a strongly acidic cation exchange resin and the adsorbent eluted using dilute aqueous ammonia. The ammonia is removed by evaporation under vacuum, and the resulting solution is condensed. Addition of alcohol and subsequent cooling provides crystals of L-threonine. Another method for the purification of L-isoleucine from culture media is reported in U.S. Pat. No. 5,474,918.

VI. Examples

The examples below are only representative of some aspects of the invention. It will be understood by those skilled in the art that the inventions as set forth in the specification can be practiced with a variety of microorganisms and promoters. These examples and the strains used therein should not be interpreted as limiting the invention in any way not explicitly stated in the claims.

Example 1

Example 1 describes the production of strains that overproduce malate synthase and isocitrate lyase by insertion of a tac promoter in positions upstream of aceB in a manner that causes an increased expression of the genes of the aceBAK operon.

Figure 3:
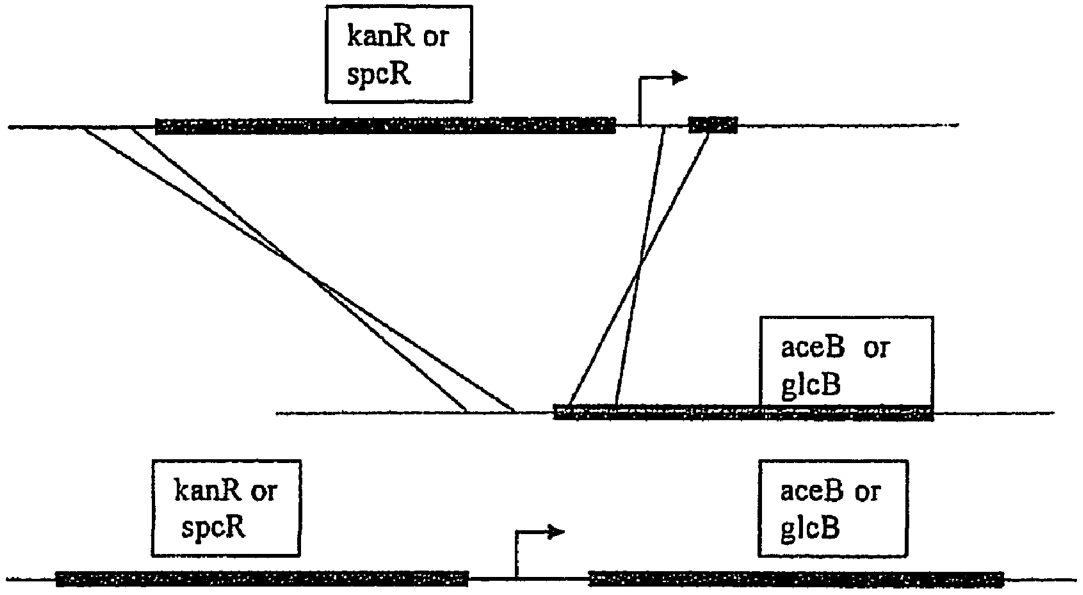
FIG. 3 depicts the integration of PCR products bearing antibiotic markers and tac promoters into the chromosome. Homologous recombination is used to exchange promoters used to express the aceBAK and glcB genes. spcR=spectinomycin resistance cartridge, kanR=kanamycin resistance cartridge. Rightward facing arrows show approximate position of heterologous promoter (Ptac). A linear PCR product (top line) containing spcR or kanR and a tac promoter are crossed into the chromosome (middle line) to yield a strain with a heterologous promoter driving aceBAK or glcB expression with an antibiotic resistance gene immediately upstream of the heterologous promoter (bottom line).

A tac promoter (de Boer, et al, 1983 and FIG. 5) was inserted upstream of the wild-type aceB gene by transformation of strain s4370-69-2 with linear DNA encoding the kanamycin resistance gene from plasmid pKD4 (Datsenko and Wanner, 2000) (FIG. 3). Strain s4370-69-2, a parent strain, lacks antibiotic resistance markers. It was deposited on May 11, 2005 at the National Center for Agricultural Utilization Research in Peoria, Ill. and given the deposit number NRRLB-30843. Plasmid pKD4 was used as template in the polymerase chain reaction (PCR) using primers aceBUS-kan4 (SEQ ID NO: 10) and a promoter construct specific primer (tacaceB-kan3 (SEQ ID NO: 11), tac(2)aceB-kan3 (SEQ ID NO: 12) or tac(3)aceB-kan3 (SEQ ID NO: 13) All primer sequences are listed in FIG. 4. Alternatively chromosomal DNA of strain s4397-184-1 (Ptac-aceBAK)(Table 1) was used as template using primers aceBUS-kan4 (SEQ ID NO: 10) and a promoter construct specific primer (tac(4)aceB (SEQ ID NO: 14), tac(5)aceB (SEQ ID NO: 15) or aceB-tac\acrev (SEQ ID NO: 16)). These PCR products contained the kanamycin resistance gene flanked by sequence homologous to that of the aceB allele of strain MG1655 (Blattner et al, 1997) and with the tac promoter substituted for the aceBAK promoter (Chung et al., 1988). PCR was performed using Advantage HF™ PCR kits (Clontech) following the manufacturer's directions. 50 ul reactions included 5 ul of 10×HF PCR reaction buffer (Clontech proprietary formula), 5 ul 10×HF dNTP mix (Clontech proprietary formula), 1 ul 50× Advantage-HF polymerase mix (which is composed of 50% glycerol, 40 mM Tris-HCL (pH 7.5), 50 mM KCl, 25 mM $(NH_4)_2SO4$, 1 mM EDTA, 5 mM 2-mercaptoethanol, 0.25% Thesit, 1.1 ug/ul TaqStart antibody, a Clontech proprietary amount of KlenTaq-1 DNA polymerase, and a proprietary amount of Deep Vent™ DNA polymerase), 0.5 ul of each primer (100 pmol/ul) and 1 ul of template DNA (1-50 pg/ul). Cycling was performed in an Applied Biosystems 9700 thermocycler as follows: pretreatment at 94° C. for 4 min then 25 cycles of 10 sec at 94° C., 30 sec at 55° C. and 90 sec at 68° C.

TABLE 1

| Strain | Promoter Construct | Primers | Template |
|---|---|---|---|
| s4397-184-1 | Ptac-aceBAK (SEQ ID NO: 19) | aceBUS-kan4 (SEQ ID NO: 10) & tacaceB-kan3 (SEQ ID NO: 11) | pKD4 |
| s4480-140-5 | Ptac(2)-aceBAK (SEQ ID NO: 20) | aceBUS-kan4 (SEQ ID NO: 10) & tac(2)aceB-kan3 (SEQ ID NO: 12) | pKD4 |
| s4480-148-1 | Ptac(3)-aceBAK (SEQ ID NO: 21) | aceBUS-kan4 (SEQ ID NO: 10) & tac(3)aceB-kan3 (SEQ ID NO: 13) | pKD4 |
| s4480-199-1 | Ptac(4)-aceBAK (SEQ ID NO: 22) | aceBUS-kan4 (SEQ ID NO: 10) & tac(4)aceB (SEQ ID NO: 14) | s4397-184-1 |
| s4538-003-1 | Ptac(5)-aceBAK (SEQ ID NO: 23) | aceBUS-kan4 (SEQ ID NO: 10) & tac(5)aceB (SEQ ID NO: 15) | s4397-184-1 |
| s4480-199-4 | Ptac\lac-aceBAK (SEQ ID NO: 24) | aceBUS-kan4 (SEQ ID NO: 10) & aceB-tac\lacrev (SEQ ID NO: 16) | s4397-184-1 |
| s4397-109-2 | Ptac-glcB (SEQ ID NO: 25) | glcBUS-spc2 (SEQ ID NO: 18) & tac-glcB-spc1 (SEQ ID NO: 17) | pBSL175 |
| s4538-006-1 | Ptac-glcB (SEQ ID NO: 25) Ptac-aceBAK (SEQ ID NO: 19) | aceBUS-kan4 (SEQ ID NO: 10) & tacaceB-kan3 (SEQ ID NO: 11) | pKD4 |
| s4370-69-2 | parent strain | | |

Table 1. Construction of eight different overexpression strains. Listed are the primers and templates used to introduce each promoter gene fusion along with the strain designations of the resultant strains.

The PCR products were then used to transform strain s4370-69-2 carrying plasmid pKD46 following protocols previously described (Datsenko and Wanner, 2000) with the following modifications: 50 ml LB (Difco) cultures, in 250 ml baffled shake flasks, of strain s4370-69-2 carrying plasmid pKD46 growing at 30° C. on an orbital shaker were grown to an $OD_{600}$ of 0.4. 0.5 ml of 20% (w/v) arabinose was then added and the cultures were allowed to grow another 2.0 hours at which time the cells were made electrocompetent following the protocol of Datsenko and Wanner (2000). Electroporation was performed by suspending 1.0-3.0 ug of precipitated PCR product in 45 □l of electrocompetent cells and transferring the mixture to a 0.1 cm electroporation cuvette. The cuvette was then pulsed in a Bio-Rad Gene Pulser® II at 1.8 kV, 25 □F, and 200Ω. The cells were then grown out in 1 ml 2YT (Difco) for 4 hours at 37° C. and the entire 1 ml was plated onto LB agar (Difco) with 50 □g/ml kanamycin and incubated at 37° C. for a period of 1-2 days. Resultant kanamycin resistant strains were cured of plasmid pKD46 as described in Datsenko and Wanner (2000) yielding strains s4397-184-1 (Ptac-aceBAK), s4480-140-5 (Ptac(2)-aceBAK), s4480-148-1 (Ptac(3)-aceBAK), s4480-199-1 (Ptac(4)-aceBAK), s4538-003-1 (Ptac(5)-aceBAK), and s4480-199-4 (Ptac\lac-aceBAK)(Table 1).

Example 2

The following example describes the production of a strain that over-produces malate synthase by the introduction of a tac promoter upstream of glcB of *Escherichia coli* positioned in a manner that causes an increased expression of the glcB gene product.

A tac promoter (de Boer, et al, 1983 and FIG. 5) was inserted upstream of the glcB gene, driving GlcB expression, by transformation of strain s4370-69-2 with linear DNA encoding the spectinomycin resistance gene from plasmid pBSL175 (Alexeyev et al, 1995) (FIG. 3). Plasmid pBSL175 was used as template in PCR using primers glcBUS-spc2 (SEQ ID NO: 18) and tac-glcB-spc1 (SEQ ID NO: 17) (all primer sequences are listed in FIG. 4). This PCR product contained the spectinomycin resistance gene flanked by sequence homologous to that of the glcB allele from MG1655 (Blattner et al, 1997) and with the tac promoter substituted for the DNA immediately upstream of the glcB gene. The PCR was performed using Advantage HF™ PCR kits (Clontech) following the manufacturer's directions. 50 ul reactions included 5 ul of 10× HF PCR reaction buffer (Clontech proprietary formula), 5 ul 10×HF dNTP mix (Clontech proprietary formula), 1 ul 50× Advantage-HF polymerase mix (which is composed of 50% glycerol, 40 mM Tris-HCL (pH 7.5), 50 mM KCl, 25 mM $(NH_4)_2SO4$, 1 mM EDTA, 5 mM 2-mercaptoethanol, 0.25% Thesit, 1.1 ug/ul TaqStart antibody, a proprietary amount of KlenTaq-1 DNA polymerase, and a proprietary amount of Deep Vent™ DNA polymerase), 0.5 ul of each primer (100 pmol/ul) and 1 ul of template DNA (1-50 pg/ul) Cycling was performed in an Applied Biosystems 9700 thermocycler as follows: pretreatment at 94° C. for 4 min then 25 cycles of 10 sec at 94° C., 30 sec at 55° C. and 90 sec at 68° C.

The PCR products were then used to transform strain s4370-69-2 carrying plasmid pKD46 following protocols previously described (Datsenko and Wanner, 2000) with the following modifications: 50 ml LB (Difco) cultures (in 250 ml baffled shake flasks) of strain s4370-69-2 carrying plasmid pKD46 growing at 30° C. on an orbital shaker were grown to an $OD_{600}$ of 0.4. Then 0.5 ml of 20% (w/v) arabinose was added and the cultures were allowed to grow another 2.0 hours at which time the cells were made electrocompetent following the procedure of Datsenko and Wanner (2000). Electroporation was performed by suspending 1.0-3.0 ug of precipitated PCR product in 45 □l of electrocompetent cells and transferring the mixture to a 0.1 cm electroporation cuvette. The cuvette was then pulsed in a Bio-Rad Gene Pulser® II at 1.8 kV, 25 □F, and 200Ω. The cells were then grown out in 1 ml 2YT (Difco) for 4 hours at 37° C. and the entire 1 ml was plated onto LB agar (Difco) with 10 □g/ml spectinomycin and incubated at 37° C. for a period of 2-3 days. The resultant spectinomycin resistant strain was cured of plasmid pKD46 as described in Datsenko and Wanner (2000), yielding strain s4397-109-2.

Example 3

The following example describes the production of a strain that over-produces malate synthase and isocitrate lyase by the introduction of tac promoters upstream of glcB and upstream of the aceBAK operon of *Escherichia coli* positioned in a manner to cause the constitutive over-expression of the glcB and aceBAK gene products.

A tac promoter (de Boer, et al, 1983 and FIG. 5) was inserted upstream of the wild-type aceB gene of strain s4397-109-2 by transformation of strain s4370-69-2 with linear DNA encoding the kanamycin resistance gene from plasmid pKD4 (Datsenko and Wanner)(FIG. 3). Plasmid pKD4 was used as template in PCR using primers aceBUS-kan4 (SEQ ID NO: 10) and tacaceB-kan3 (SEQ ID NO: 11) (all primer sequences are listed in FIG. 4). This PCR product contained the kanamycin resistance gene flanked by sequence homologous to that of the aceB allele of strain MG1655 (Blattner et al., 1997) and with the tac promoter substituted for the aceBAK promoter (Chung et al., 1988). The PCR was performed using Advantage HF™ PCR kits (Clontech) following the manufacturer's directions. 50 ul reactions included 5 ul of 10×HF PCR reaction buffer (Clontech proprietary formula), 5 ul 10×HF dNTP mix (Clontech proprietary formula), 1 ul 50× Advantage-HF polymerase mix (which is composed of 50% glycerol, 40 mM Tris-HCL (pH 7.5), 50 mM KCl, 25 mM $(NH_4)_2SO4$, 1 mM EDTA, 5 mM 2-mercaptoethanol, 0.25% Thesit, 1.1 ug/ul TaqStart antibody, a Clontech proprietary amount of KlenTaq-1 DNA polymerase, and a Clontech proprietary amount of Deep Vent™ DNA polymerase), 0.5 ul of each primer (100 pmol/ul) and 1 ul of template DNA (1-50 pg/ul) Cycling was performed in an Applied Biosystems 9700 thermocycler as follows: pretreatment at 94° C. for 4 min then 25 cycles of 10 sec at 94° C., 30 sec at 55° C. and 90 sec at 68° C.

The PCR product was then used to transform strain s4397-109-1 carrying plasmid pKD46 following protocols previously described (Datsenko and Wanner, 2000) with the following modifications: 50 ml LB (Difco) cultures (in 250 ml baffled shake flasks) of strain s4397-109-1 carrying plasmid pKD46 growing at 30° C. on an orbital shaker were grown to an $OD_{600}$ of 0.4. 0.5 ml of 20% (w/v) arabinose was then added and the cultures were allowed to grow another 2.0 hours at which time the cells were made electrocompetent following the procedure of Datsenko and Wanner (2000). Electroporation was performed by suspending 1.0-3.0 ug of precipitated PCR product in 45 □l of electrocompetent cells and transferring the mixture to a 0.1 cm electroporation cuvette. The cuvette was then pulsed in a Bio-Rad Gene Pulser® II at 1.8 kV, 25 □F, and 200Ω. The cells were then grown out in 1 ml 2YT (Difco) for 4 hours at 37° C. and the entire 1 ml was plated onto LB agar (Difco) with 50 □g/ml kanamycin and incubated at 37° C. for a period of 1-2 days.

The resultant kanamycin resistant strain was cured of plasmid pKD46 as described in Datsenko and Wanner (2000), yielding strain s4538-006-1.

Example 4

The following example illustrates a utility of placing a tac promoter upstream of and driving expression of glcB and the aceBAK operon for providing constitutive high expression levels of glyoxylate shunt enzymes.

Expression levels of glyoxylate shunt genes were assessed by measurement of enzyme specific activity levels of malate synthase and isocitrate lyase. Cultures for enzyme assays were grown in 50 ml Davis minimal media (Difco) supplemented with 0.1% (w/v) casamino acids (Difco) and either 0.4% (w/v) dextrose or a combination of 0.4% (w/v) glycerol and 0.4% Na-acetate (w/v) in a 250 ml baffled flask on a New Brunswick G53 shaker at 240 rpm at 37° C. Malate synthase levels were measured by following the glyoxylate dependent release of free CoA from acetyl-CoA according to the method of Omston and Omston (1969). Isocitrate lyase levels were measured by following the isocitrate dependent production of glyoxylate according to the method of Maloy et al. (1980). Table 2 shows that the introduction of a tac promoter in front of the aceB gene increases the enzyme levels of both malate synthase and of isocitrate lyase whether grown with dextrose or with glycerol plus acetate relative to wild-type. Table 2 also shows that the introduction of a tac promoter in front of the glcB gene greatly increases the level of malate synthase, but leaves the level of isocitrate lyase unchanged.

TABLE 2

| | | Malate Synthase Activity (nmol/min/mg) | | Isocitrate Lyase Activity (nmol/min/mg) | |
|---|---|---|---|---|---|
| Strain | Genotype | Dextrose | Glycerol + Acetate | Dextrose | Glycerol + Acetate |
| s4370-69-2 | Parent strain | 4.7 | 62.4 | 3.1 | 6.3 |
| s4397-184-1 | Ptac-aceBAK | 47.2 | 91.1 | 143.1 | 222.7 |
| s4480-140-5 | Ptac(2)-aceBAK | 149.9 | 172.5 | 168.7 | 234.4 |
| s4480-148-1 | Ptac(3)-aceBAK | 247.9 | 155.3 | 225.1 | 314.3 |
| s4480-199-1 | Ptac(4)-aceBAK | 124.7 | 159.9 | 157.2 | 318.1 |
| s4538-003-1 | Ptac(5)-aceBAK | 139.0 | 148.1 | 203.3 | 250.0 |
| s4480-199-4 | Ptac\lac-aceBAK | 145.3 | 174.0 | 105.3 | 302.1 |
| s4397-109-2 | Ptac-glcB | 932.1 | 1730.7 | 1.4 | 3.3 |
| s4538-006-1 | Ptac-glcB Ptac-aceBAK | 1981.0 | 2115.1 | 63.5 | 212.3 |

Table 2. Malate synthase and isocitrate lyase specific activities of seven over-expression strains along with the parent strain (s4370-69-2). Each strain/media combination was assayed a minimum of six times and averages are shown. The strains were grown in Davis minimal media (Difco) with 0.1% casamino acids (Difco). The carbon source was either 0.4% dextrose or 0.4% glycerol+0.4% sodium acetate.

Example 5

The following example illustrates the usefulness of over-expressing enzymes of the glyoxylate shunt for increasing threonine yields and titers in threonine production strains.

Performance of the over-expression strains was tested in shake flasks using media BTC3 (1.0 g/l K2HPO4, 10.0 g/l (NH4)2SO4, 40.8 g/l Bis-Tris, 20 ml/l 50% solids corn steep liquor (Sigma), 25.0 g/l dextrose, and 1.2 g/l MgSO4-7H2O pH 7.0). Actively growing LB (Difco) cultures were used to inoculate media BTY2 (1.0 g/l K2HPO4, 10.0 g/l (NH4)2SO4, 40.8 g/l Bis-Tris, 15 g/l yeast extract (Difco), 32.5 g/l dextrose, and 1.2 g/l MgSO4-7H2O pH 7.0) (0.1 ml into 20 ml BTY2). After 18 hrs, 0.25 ml of BTY2 was passed into 20 ml of BTC3. After a further 24 hours, BTC3 cultures were harvested and the threonine and dextrose concentrations were determined. All cultures were grown in 250 ml baffled flasks, on a New Brunswick G53 shaker set at 240 rpm at 37° C. Results are shown in Tables 3, 4, and 5.

Table 3, 4, and 5. Threonine production of mutant strains in shake flasks. Cultures were grown in media BTC3 and threonine and dextrose concentrations were determined. Representative experiments shown are the averages of six flasks for each strain. Where different tables show the same strain, results are separated by week.

TABLE 3

| Strain | Relevant genotype | Titer (g/l) | Yield (g threonine/g dextrose) |
|---|---|---|---|
| s4370-69-2 | Parent | 7.2 | 0.274 |
| s4397-184-1 | Ptac-aceB | 7.9 | 0.299 |
| s4538-199-1 | Ptac(4)-aceB | 7.8 | 0.298 |
| s4538-003-1 | Ptac(5)-aceB | 7.6 | 0.289 |
| s4480-199-4 | Ptac\lac-aceB | 7.8 | 0.297 |
| s4538-006-1 | Ptac-glcB Ptac-aceB | 7.7 | 0.293 |

TABLE 4

| Strain | Relevant genotype | Threonine Titer (g/l) | Yield (g/g) |
|---|---|---|---|
| s4370-69-2 | Parent | 8.1 | 0.296 |
| s4397-184-1 | Ptac-aceB | 8.4 | 0.306 |
| s4480-140-5 | Ptac(2)-aceB | 8.0 | 0.294 |
| s4480-148-1 | Ptac(3)-aceB | 8.1 | 0.297 |

TABLE 5

| Strain | Relevant genotype | Titer (g/l) | Yield (g/g) |
|---|---|---|---|
| S4370-69-2 | Parent | 8.3 | 0.307 |
| S4397-109-2 | Ptac-glcB | 8.0 | 0.298 |

Example 6

Example 6 includes the production of a strain that overproduces malate synthase G by the introduction of a plasmid including a lac promoter operably associated with a native glcB promoter of *Escherichia coli*. Example 6 is a prophetic example. The experiments and procedures in Example 6 have not been performed and are meant to be illustrative only.

A pUC-based plasmid is constructed that contains the glcB gene from *E. coli* strain s4370-69-2 operably associated with the lac promoter of the pUC-based plasmid. Construction of the plasmid is performed by methods known to those skilled in the art and with the benefit of this disclosure. The lac::glcB plasmid is introduced into the s4370-69-2 parent strain by electroporation, generating a strain in which glcB is overexpressed by operation of the lac promoter. Inclusion of the plasmid is demonstrated by restriction mapping and Southern blot analysis.

The strain produced in this example is cultured in a suitable medium to demonstrate expression levels of glcB. Such a medium may be, but is not limited to, Davis minimal media supplemented with casamino acids and either dextrose or a combination of glycerol and sodium acetate. Levels of malate synthase G are increased over similar experiments with the parent strain, as demonstrated by a specific activity that is as little as two to as much as seventy-five times greater than the specific activity in the parent strain.

Increased levels of malate synthase G lead to increased production of L-threonine in the modified strain when compared to L-threonine production in the parent strain, as is shown by culture of the modified strain in growth media such as BTC3, described above. L-threonine yield of a culture of the modified plasmid-containing strain is increased by as much as 10% over that of the parent strain.

Patents, patent applications, publications, scientific articles, books, web sites, and other documents and materials referenced or mentioned herein are indicative of the levels of skill of those skilled in the art to which the inventions pertain. Each such referenced document and material is hereby incorporated by reference to the same extent as if it had been incorporated by reference in its entirety individually or set forth or reprinted herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, and the claims referred to above including but not limited to any original claims.

The inventions have been described broadly and generically herein. Each of the narrower species and subgeneric groupings falling within the generic disclosure also form part of these inventions. This includes the generic description of each invention which hereby include, including any claims thereto, a proviso or negative limitation removing or optionally allowing the removal of any subject matter from the genus, regardless of whether or not the excised materials or options were specifically recited or identified in haec verba herein, and all such variations form a part of the original written description of the inventions. In addition, where features or aspects of an invention are described in terms of a Markush group, the invention shall be understood thereby to be described in terms of each and every, and any, individual member or subgroup of members of the Markush group.

The inventions illustratively described and claimed herein can suitably be practiced in the absence of any element or elements, limitation or limitations, not specifically disclosed herein or described herein as essential. Thus, for example, the terms "comprising," "including," "containing," "for example," etc., shall be read expansively and without limitation. In claiming their inventions, the inventors reserve the right to substitute any transitional phrase with any other transitional phrase, and the inventions shall be understood to include such substituted transitions and form part of the original written description of the inventions. Thus, for example, the term "comprising" may be replaced with either of the transitional phrases "consisting essentially of" or "consisting of."

As used herein and in the appended claims, the singular forms "a," "an," and "the" include plural reference unless the context clearly dictates otherwise.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement was specifically and without qualification or reservation expressly adopted by Applicants in a responsive writing specifically relating to the application that led to this patent prior to its issuance.

The terms and expressions employed herein have been used as terms of description and not of limitation, and there is no intention in the use of such terms and expressions, or any portions thereof, to exclude any equivalents now know or later developed, whether or not such equivalents are set forth or shown or described herein or whether or not such equivalents are viewed as predictable, but it is recognized that various modifications are within the scope of the invention claimed, whether or not those claims issued with or without alteration or amendment for any reason. Thus, it shall be understood that, although the present invention has been specifically disclosed by preferred embodiments and optional features, modifications and variations of the inventions embodied therein or herein disclosed can be resorted to by those skilled in the art, and such modifications and variations are considered to be within the scope of the inventions disclosed and claimed herein.

Specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. Where examples are given, the description shall be construed to include but not to be limited to only those examples. It will be readily apparent to one skilled in the art that varying substitutions and modifications may be made to the invention disclosed herein without departing from the scope and spirit of the invention, and from the description of the inventions, including those illustratively set forth herein, it is manifest that various modifications and equivalents can be used to implement the concepts of the present invention without departing from its scope. A person of ordinary skill in the art will recognize that changes can be made in form and detail without departing from the spirit and the scope of the invention. The described embodiments are to be considered in all respects as illustrative and not restrictive. Thus, for example, additional embodiments are within the scope of the invention and within the following claims.

We claim:

1. A bacterium comprising a first recombinant nucleic acid integrated into its genome, said first recombinant nucleic acid having an isocitrate lyase coding sequence of an *E. coli* aceBAK operon operably associated with a first non-native promoter that provides a means for the bacterium to overexpress the isocitrate lyase coding sequence and wherein the bacterium simultaneously overexpresses at least one of a malate synthase G coding sequence from a glcB gene and a malate synthase A coding sequence from the aceB operon, wherein when the glcB gene is over expressed the glcB gene is expressed from a second recombinant nucleic acid integrated into the genome and said glcB gene is operably associated with a second non-native promoter that provides means for overexpression of the malate synthase G coding sequence of the glcB gene simultaneously with overexpression of the isocitrate lyase coding sequence from the aceBAK operon.

2. The bacterium of claim 1, wherein said first non-native promoter is selected from the group consisting of a tac promoter, a trc promoter, a lac promoter, a trp promoter, a lambda-$P_L$ promoter, a lambda-$P_R$ promoter, a lacUV5 promoter, an araBAD promoter, a lpp promoter, and a lpp-lac promoter.

3. The bacterium of claim 1, wherein a native promoter of said aceBAK operon is displaced by the first non-native promoter.

4. The bacterium of claim 1, wherein the first non-native promoter is inserted in said aceBAK operon without replacing or interrupting a native promoter of said aceBAK operon.

5. The bacterium of claim 1, wherein a native promoter of said glcB gene is displaced by said second non-native promoter.

6. The bacterium of claim 1, wherein the second non-native promoter is operably linked to said glcB gene without displacing a native promoter operably associated with said glcB gene.

7. A bacterial strain selected from the group consisting of those with the deposit numbers NRRLB-30843, NRRLB-30844, NRRLB-30845, NRRLB-30846, NRRLB-30847, NRRLB-30848, NRRLB-30849, NRRLB-30850, NRRLB-30851, and derivatives thereof.

8. The bacterium of claim 1, wherein the isocitrate lyase coding sequences of the aceBAK operon comprises the nucleotide sequence of SEQ ID NO: 2, and wherein said first non-native promoter is a tac promoter having a nucleotide sequence of SEQ ID NO: 9.

9. The bacterium of claim 1, wherein the glcB gene having the coding sequence for malate synthase G has the nucleotide sequence of SEQ ID NO: 7.

10. The bacterium of claim 1, wherein said recombinant nucleic acid having an isocitrate lyase coding sequence of an *E. coli* aceBAK operon operably associated with a first non-native promoter comprises a nucleotide sequence selected from SEQ ID NO: 19; SEQ ID NO: 21, SEQ ID NO: 22, SEQ ID NO: 23, and SEQ ID NO: 24.

11. The bacterium of claim 1, wherein said second non-native promoter and said glcB gene have the nucleotide sequence of SEQ ID NO: 25.

12. The bacterium of claim 1, wherein said bacterium is from a genus selected from the group consisting of *Escherichia, Corynebacterium* and *Brevibacterium.*

13. The bacterium of claim 1, wherein said bacterium produces threonine when grown on the medium containing dextrose in a greater amount than a parent of said bacterium lacking said recombinant nucleic acid.

14. The bacterium of claim 1, where said bacterium is a strain of *Escherichia coli.*

15. The bacterium of claim 1 wherein said malate synthase G from the glcB gene is simultaneously overexpressed with the malate synthase A from the aceB gene of the aceBAK operon.

* * * * *